US012472322B2

(12) United States Patent
Nga et al.

(10) Patent No.: US 12,472,322 B2
(45) Date of Patent: Nov. 18, 2025

(54) SEAL-FORMING STRUCTURE FOR PATIENT INTERFACE INCLUDING TEXTILE SEAL MEMBER

(71) Applicant: RESMED PTY LTD, Bella Vista (AU)

(72) Inventors: Lemmy Nga, Sydney (AU); Ryan Michael Kirkpatrick, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 967 days.

(21) Appl. No.: 17/623,522

(22) PCT Filed: Jun. 24, 2020

(86) PCT No.: PCT/IB2020/055968
§ 371 (c)(1),
(2) Date: Dec. 28, 2021

(87) PCT Pub. No.: WO2020/261139
PCT Pub. Date: Dec. 30, 2020

(65) Prior Publication Data
US 2022/0355055 A1 Nov. 10, 2022

(30) Foreign Application Priority Data
Jun. 28, 2019 (AU) ................................ 2019902284

(51) Int. Cl.
*A61M 16/06* (2006.01)

(52) U.S. Cl.
CPC . *A61M 16/0616* (2014.02); *A61M 2205/0216* (2013.01)

(58) Field of Classification Search
None
See application file for complete search history.

(56) References Cited

U.S. PATENT DOCUMENTS 4,782,832 A 11/1988 Trimble et al.
4,944,310 A 7/1990 Sullivan
(Continued)

FOREIGN PATENT DOCUMENTS

JP 2014-524801 9/2014
JP 2017-531489 10/2017
(Continued)

OTHER PUBLICATIONS

"Respiratory Physiology", by John B. West, Lippincott Williams & Wilkins, 9th edition published 2012 (8 pages).
(Continued)

*Primary Examiner* — Bradley H Philips
(74) *Attorney, Agent, or Firm* — Nixon & Vanderhye P.C.

(57) ABSTRACT

A patient interface may have a frame and a seal-forming structure. The frame may at least partially form a plenum chamber pressurisable to a therapeutic pressure. The seal-forming structure may be constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use. The seal-forming structure may comprise a textile seal member adapted to sealingly engage the patient's face in use.

29 Claims, 39 Drawing Sheets

(56) References Cited

U.S. PATENT DOCUMENTS

| | | | | | |
|---|---|---|---|---|---|
| 5,003,633 | A * | 4/1991 | Itoh | A62B 18/025 2/9 |
| 5,538,000 | A | 7/1996 | Rudolph | |
| 6,532,959 | B1 | 3/2003 | Berthon-Jones | |
| 6,581,594 | B1 * | 6/2003 | Drew | A61M 16/0633 128/207.12 |
| 7,866,944 | B2 | 1/2011 | Kenyon et al. | |
| 8,636,479 | B2 | 1/2014 | Kenyon et al. | |
| 8,638,014 | B2 | 1/2014 | Sears et al. | |
| 8,733,349 | B2 | 5/2014 | Bath et al. | |
| 8,925,548 | B2 | 1/2015 | Pierro | |
| 2008/0047560 | A1 | 2/2008 | Veliss et al. | |
| 2009/0044808 | A1 | 2/2009 | Guney et al. | |
| 2009/0050156 | A1 | 2/2009 | Ng et al. | |
| 2010/0000534 | A1 | 1/2010 | Kooij et al. | |
| 2011/0247628 | A1 | 10/2011 | Ho | |
| 2014/0158136 | A1 * | 6/2014 | Romagnoli | A61M 16/0611 128/206.24 |
| 2014/0326243 | A1 * | 11/2014 | Znamenskiy | A61M 16/0633 128/205.25 |
| 2014/0326246 | A1 * | 11/2014 | Chodkowski | A61M 16/0622 128/206.24 |
| 2015/0144131 | A1 * | 5/2015 | Varga | A61M 16/0833 128/202.22 |
| 2017/0326320 | A1 * | 11/2017 | Baigent | A61M 16/0616 |
| 2018/0256845 | A1 | 9/2018 | Gibson et al. | |
| 2018/0318539 | A1 | 11/2018 | Scheiner et al. | |
| 2019/0070379 | A1 | 3/2019 | Lockhart et al. | |
| 2019/0240436 | A1 | 8/2019 | Romagnoli et al. | |
| 2020/0016358 | A1 * | 1/2020 | Bornholdt | A61M 16/109 |

FOREIGN PATENT DOCUMENTS

| | | | |
|---|---|---|---|
| WO | WO 98/004310 | A1 | 2/1998 |
| WO | WO 98/034665 | A1 | 8/1998 |
| WO | WO 2000/078381 | A1 | 12/2000 |
| WO | WO 2004/073778 | A1 | 9/2004 |
| WO | WO 2005/063328 | A1 | 7/2005 |
| WO | WO 2006/074513 | A1 | 7/2006 |
| WO | WO 2006/130903 | A1 | 12/2006 |
| WO | 2008/011683 | | 1/2008 |
| WO | WO 2009/052560 | A1 | 4/2009 |
| WO | WO 2009/062265 | A1 | 5/2009 |
| WO | WO 2010/135785 | A1 | 12/2010 |
| WO | WO 2012/171072 | A1 | 12/2012 |
| WO | WO 2013/006913 | A1 | 1/2013 |
| WO | WO 2013/020167 | A1 | 2/2013 |
| WO | WO 2013/026091 | A1 | 2/2013 |
| WO | WO 2014/110626 | A1 | 7/2014 |
| WO | WO 2015/151019 | A1 | 10/2015 |
| WO | WO 2016/082001 | A1 | 6/2016 |
| WO | WO 2017/042717 | A1 | 3/2017 |
| WO | WO 2017/049360 | A1 | 3/2017 |
| WO | 2018/160077 | A1 | 9/2018 |
| WO | WO 2019/003094 | A1 | 1/2019 |
| WO | 2019/119058 | | 6/2019 |

OTHER PUBLICATIONS

International Search Report dated Sep. 21, 2020 issued in International Application No. PCT/IB2020/055968 (21 pages).

Written Opinion of the International Searching Authority dated Sep. 21, 2020 issued in International Application No. PCT/IB2020/055968 (7 pages).

International Preliminary Report on Patentability dated Aug. 16, 2021 issued in International Application No. PCT/IB2020/055968 (53 pages).

Office Action dated Jul. 18, 2023 issued in Japanese Application No. 2021-577613 with English translation (5 pages).

Office Action dated Oct. 19, 2022 issued in European Application No. 20832617.3 (6 pages).

Notice of Reasons for Refusal with English translation issued in corresponding JP Application No. 2024-070712, seven pages, dated Feb. 4, 2025.

Extended European Search Report issued in corresponding EP Application No. 24213943.4, seven pages, dated May 20, 2025.

* cited by examiner

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2012 ResMed Limited

Copyright 2015 ResMed Limited

Copyright 2015 ResMed Limited

Copyright 2015 ResMed Limited

Copyright 2015 ResMed Limited

SEAL-FORMING STRUCTURE FOR PATIENT INTERFACE INCLUDING TEXTILE SEAL MEMBER

1 CROSS-REFERENCE TO RELATED APPLICATION

This application is the U.S. national phase of International Application No. PCT/IB2020/055968 filed Jun. 24, 2020 which designated the U.S. and claims priority to Australian Provisional Patent Application No. 201902284, filed Jun. 28, 2019, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads vanes considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 $cmH_2O$ pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 $cmH_2O$)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology comprises a patient interface comprising:

- a frame, wherein the frame at least partially forms a plenum chamber pressurisable to a therapeutic pressure of at least 6 $cmH_2O$ above ambient air pressure;
- a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use,
- wherein the seal-forming structure comprises a compliant portion provided to the frame, a rigidizing element provided within the compliant portion, and a seal member adapted to sealingly engage the patient's face in use, and
- wherein the frame and the seal member are at least partially constructed from a textile material, and the compliant portion is constructed from a resilient material that is different than the textile material.

One form of the present technology comprises a patient interface comprising:

- a frame, wherein the frame partially forms a plenum chamber pressurisable to a therapeutic pressure of at least 6 $cmH_2O$ above ambient air pressure, the frame at least partially formed from a textile;
- a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, wherein the seal-forming structure comprises a textile seal member adapted to sealingly engage the patient's face in use; and a positioning and stabilizing structure configured to provide a force to maintain the seal-forming structure in a therapeutically effective position on the patient's head, the positioning and stabilizing structure at least partially formed from a textile;

wherein the frame comprises a plenum chamber portion, the seal-forming structure is provided to a posterior facing surface of the plenum chamber portion, and the plenum chamber portion extends over the hole of the seal-forming structure, wherein the frame comprises a lateral portion extending beyond the seal-forming structure in a direction away from the hole of the seal-forming structure, and, wherein the lateral portions connects the frame to the positioning and stabilizing structure via a one-piece textile construction.

One form of the present technology comprises a patient interface comprising:

a frame, wherein the frame at least partially forms a plenum chamber pressurisable to a therapeutic pressure of at least 6 $cmH_2O$ above ambient air pressure;

a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, wherein the seal-forming structure comprises:

a compliant portion provided to the frame, one or more rigidizing elements provided in the compliant portion, the one or more rigidizing elements being made of a different material than the compliant portion, and a textile seal member provided to the compliant portion and adapted to sealingly engage the patient's face in use.

One form of the present technology comprises a patient interface comprising:

a frame, wherein the frame at least partially forms a plenum chamber pressurisable to a therapeutic pressure of at least 6 $cmH_2O$ above ambient air pressure;

a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, wherein the seal-forming structure comprises a compliant portion provided to the frame, and a seal member adapted to surround the entrance to the patient's airways and sealingly engage the patient's face in use, and wherein the frame and the seal member are at least partially constructed from a textile material, and the compliant portion is constructed from a resilient material that is different than the textile material.

One form of the present technology comprises a patient interface comprising:

a frame, wherein the frame at least partially forms a plenum chamber pressurisable to a therapeutic pressure of at least 6 $cmH_2O$ above ambient air pressure;

a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, wherein the seal-forming structure comprises:

a compliant portion provided to the frame, wherein the width of the compliant portion is greater than the thickness of the compliant portion, and a textile seal member provided to the compliant portion and adapted to sealingly engage the patient's face in use, the textile seal member having a cantilever configuration with respect to the compliant portion, and the frame extending generally parallel with respect to the textile seal member.

One form of the present technology comprises a patient interface comprising:

a frame, wherein the frame at least partially forms a plenum chamber pressurisable to a therapeutic pressure of at least 6 $cmH_2O$ above ambient air pressure;

a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, wherein the seal-forming structure comprises:

a compliant portion provided to the frame, one or more rigidizing elements provided in the compliant portion, the one or more rigidizing elements being made of a different material than the compliant portion, and a textile seal member provided to the compliant portion and adapted to sealingly engage the patient's face in use, wherein the textile seal member comprises an overhanging portion extending from the compliant portion.

In examples, the overhanging portion of the textile seal member may extend from the compliant portion in a radially inward direction.

One form of the present technology comprises a patient interface comprising:

a frame, wherein the frame at least partially forms a plenum chamber pressurisable to a therapeutic pressure of at least 6 $cmH_2O$ above ambient air pressure, the frame formed at least partially from a textile material;

a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use,

- wherein the seal-forming structure comprises a textile seal member adapted to sealingly engage the patient's face in use,
- wherein the textile seal member comprises at least one seal enhancing feature on a posterior facing surface of the textile seal member, and
- wherein the frame extends generally parallel to the textile seal member along a length of the seal-forming structure.

In examples of the preceding aspects: (a) the frame is flexible; (b) the frame is made of a flexible material; (c) the frame is made entirely of the textile material; (d) the frame comprises a plenum chamber portion, the seal-forming structure is provided to a posterior facing surface of the plenum chamber portion, and the plenum chamber portion extends over a hole of the seal-forming structure through which the flow of air at said therapeutic pressure is delivered to at least an entrance to the patient's nares; (e) the frame comprises lateral portions extending beyond the seal-forming structure in a direction away from the hole of the seal-forming structure; (f) wherein the rigidizing element is exposed to ambient.

In examples of the preceding aspects: (a) the seal-forming structure comprises a textile seal member adapted to sealingly engage the patient's face in use; (b) the textile seal member is adapted to surround the entrance to the patient's airways and sealingly engage the patient's face in use; (c) the width of the textile seal member changes along its length; (d) the textile seal member is air impermeable; the textile seal member is air permeable; (e) the seal-forming structure comprises a compliant portion provided to the frame, and the textile seal member is provided to the compliant portion and adapted to sealingly engage the patient's face in use; (f) the width of the compliant portion is greater than the thickness of the compliant portion; (g) the thickness of the compliant portion varies between different regions of the seal-forming structure; (h) the width of the compliant portion varies between different regions of the seal-forming structure; the compliant portion is made of a foam material; (i) the compliant portion has a structure providing compliant properties; (j) the textile seal member comprises an overhanging portion extending from the compliant portion; (k) the overhanging portion of the textile seal member overhangs the compliant portion in a radially inward direction; (l) the overhanging portion of the textile seal member provides a pressure assisted seal; (m) wherein the one or more rigidizing elements is exposed to ambient; (n) the one or more rigidizing elements limits compression of the compliant portion and maintains a thickness between the frame and the textile seal member.

In examples of the preceding aspects: (a) the textile seal member comprises at least one seal enhancing feature on a posterior facing surface of the textile seal member; (b) the seal enhancing feature increases the tackiness of the textile seal member; (c) the seal enhancing feature comprises a layer of seal enhancing material; (d) the seal enhancing feature comprises seal enhancing material provided in a discontinuous manner; (e) the seal enhancing material is one or more of: a polyurethane, and a silicone; (f) the seal enhancing feature is provided in a select region or regions along the length of the textile seal member; (g) the seal enhancing feature is provided to a greater extent in a select region in comparison with one or more other regions; (h) the seal enhancing feature is provided to a greater extent in regions that in use contact a nasal or nose bridge region or on a nose-ridge region of the patient's face; (i) the seal enhancing feature is provided along the entirety of the length of the textile.

In examples of the preceding aspects: (a) the patient interface comprises a positioning and stabilising structure, wherein the positioning and stabilising structure provides a force to hold the seal-forming structure in a therapeutically effective position on the patient's head; (b) the positioning and stabilising structure is provided to the frame; (c) the positioning and stabilising structure is stitched, bonded or integrally formed with the frame; (d) at least a portion of the positioning and stabilising structure is elastic.

In examples of the preceding aspects: (a) the patient interface comprises at least one conduit configured to deliver the flow of air at the therapeutic pressure for breathing by the patient to the plenum chamber; (b) the conduit is provided to a medial and inferior position on the frame; (c) a first conduit and a second conduit pass along lateral sides of the patient's head between corresponding ones of the patient's eyes and ears; (d) the first conduit and the second conduit form a portion of the positioning and stabilising structure.

In examples of the preceding aspects: (a) the patient interface comprises a vent structure to allow a continuous flow of gases exhaled by the patient from an interior of the plenum chamber to ambient, said vent structure being sized and shaped to maintain the therapeutic pressure in the plenum chamber in use; (b) the vent structure comprises vent holes in flexible material of the frame; (c) the vent structure comprises vent holes in a rigid insert provided to the frame; (d) the vent structure comprises an air permeable portion of the frame; (e) the vent structure is provided in a connection port provided to the frame.

In other examples of the preceding aspects: (a) the seal member contacts the ridge of the patient's nose and the patient's supramenton, in use; (b) the seal member is disposed proximate to the patient's pronasale and configured to be disposed adjacent to the patient's lateral and/or greater alar cartilage, in use; (c) an uppermost point of the seal member is configured to be substantially aligned with the patient's Frankfort Horizontal, in use; and (d) the seal member forms a perimeter, and the patient's nasolabial sulcus are configured to be disposed within the perimeter, in use.

One form of the present technology comprises a patient interface comprising:

- a frame, wherein the frame at least partially forms a plenum chamber pressurisable to a therapeutic pressure of at least 6 $cmH_2O$ above ambient air pressure; and
- a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use.

One form of the present technology comprises a patient interface comprising:

- a frame, wherein the frame partially forms a plenum chamber pressurisable to a therapeutic pressure of at least 6 $cmH_2O$ above ambient air pressure;
- a seal-forming structure constructed and arranged to form a seal with a region of the patient's face surrounding an entrance to the patient's airways; and a positioning and stabilizing structure configured to provide a force to maintain the seal-forming structure in a therapeutically effective position on the patient's head.

One form of the present technology comprises a seal-forming structure comprising:

a compliant portion provided to the frame, one or more rigidizing elements provided in the compliant portion, the one or more rigidizing elements being made of a different material than the compliant portion, and a textile seal member provided to the compliant portion and adapted to sealingly engage the patient's face in use, wherein the textile seal member comprises an overhanging portion extending from the compliant portion.

One form of the present technology comprises a seal-forming structure comprising:

a compliant portion provided to the frame, one or more rigidizing elements provided in the compliant portion, the one or more rigidizing elements being made of a different material than the compliant portion, and a textile seal member provided to the compliant portion and adapted to sealingly engage the patient's face in use.

One form of the present technology comprises a seal-forming structure comprising:

a compliant portion provided to the frame, wherein the width of the compliant portion is greater than the thickness of the compliant portion, and a textile seal member provided to the compliant portion and adapted to sealingly engage the patient's face in use, the textile seal member having a cantilever configuration with respect to the compliant portion, and the frame extending generally parallel with respect to the textile seal member.

One form of the present technology comprises a patient interface comprising:

a frame according to any one of the preceding aspects or examples thereof, wherein the frame at least partially forms a plenum chamber pressurisable to a therapeutic pressure of at least 6 $cmH_2O$ above ambient air pressure, said plenum chamber including a plenum chamber inlet port sized and structured to receive a flow of air at the therapeutic pressure for breathing by a patient, a seal-forming structure according to any one of the preceding aspects or examples thereof, wherein the seal-forming structure is constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

a positioning and stabilising structure according to any one of the preceding aspects or examples thereof, wherein the positioning and stabilising structure provides a force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breath from ambient through their mouth in the absence of a flow of pressurised air through the plenum chamber inlet port, or the patient interface is configured to leave the patient's mouth uncovered.

One form of the present technology comprises a patient interface comprising:

a frame, wherein the frame partially forms a plenum chamber pressurisable to a therapeutic pressure of at least 6 $cmH_2O$ above ambient air pressure, the frame at least partially formed from a textile;

a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use, wherein the seal-forming structure comprises a textile seal member adapted to sealingly engage the patient's face in use;

a positioning and stabilizing structure configured to provide a force to maintain the seal-forming structure in a therapeutically effective position on the patient's head, the positioning and stabilizing structure at least partially formed from a textile, the positioning and stabilizing structure including an upper strap configured to pass between an eye and an ear of the patient; and at least one conduit configured to deliver the flow of air at the therapeutic pressure for breathing by the patient to the plenum chamber;

wherein the frame, seal-forming structure, positioning and stabilizing structure, and at least one conduit are connected together via a one-piece textile construction; and wherein the at least one conduit overlays the upper strap.

In examples of the preceding aspects: (a) the seal-forming structure is configured to form a seal around the patient's nares only, or around the patient's nares and the patient's mouth; (b) the positioning and stabilizing structure forms at least a portion of the at least one conduit; (c) the at least one conduit comprises a first conduit and a second conduit, each passing along lateral sides of the patient's head between corresponding ones of the patient's eyes and ears; (d) the at least one conduit is translationally fixed relative to the positioning and stabilising structure; (e) the at least one conduit includes at least one nasal opening configured to seal around the patient's alar rims; and/or (f) the at least one conduit further includes an oral opening configured to convey pressurized air to the patient's mouth.

In examples of the preceding aspects: (a) a rigidizing portion provided at least partially on an anterior facing surface of the frame, and connected to the frame via the one-piece construction; (b) the rigidizing portion is constructed from a different material than the frame; (c) an upper portion that extends along an upper strap of the positioning and stabilizing structure, and a lower portion that extends along a lower strap of the positioning and stabilizing structure; (d) the upper portion and the lower portion are connected to the positioning and stabilizing structure via the one-piece construction; (e) the upper portion and the lower portion extend further in a lateral direction than the at least one conduit; (f) the upper portion and the lower portion extend to substantially the same distance from the patient's head; and/or (g) the rigidizing portion is constructed from foam.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
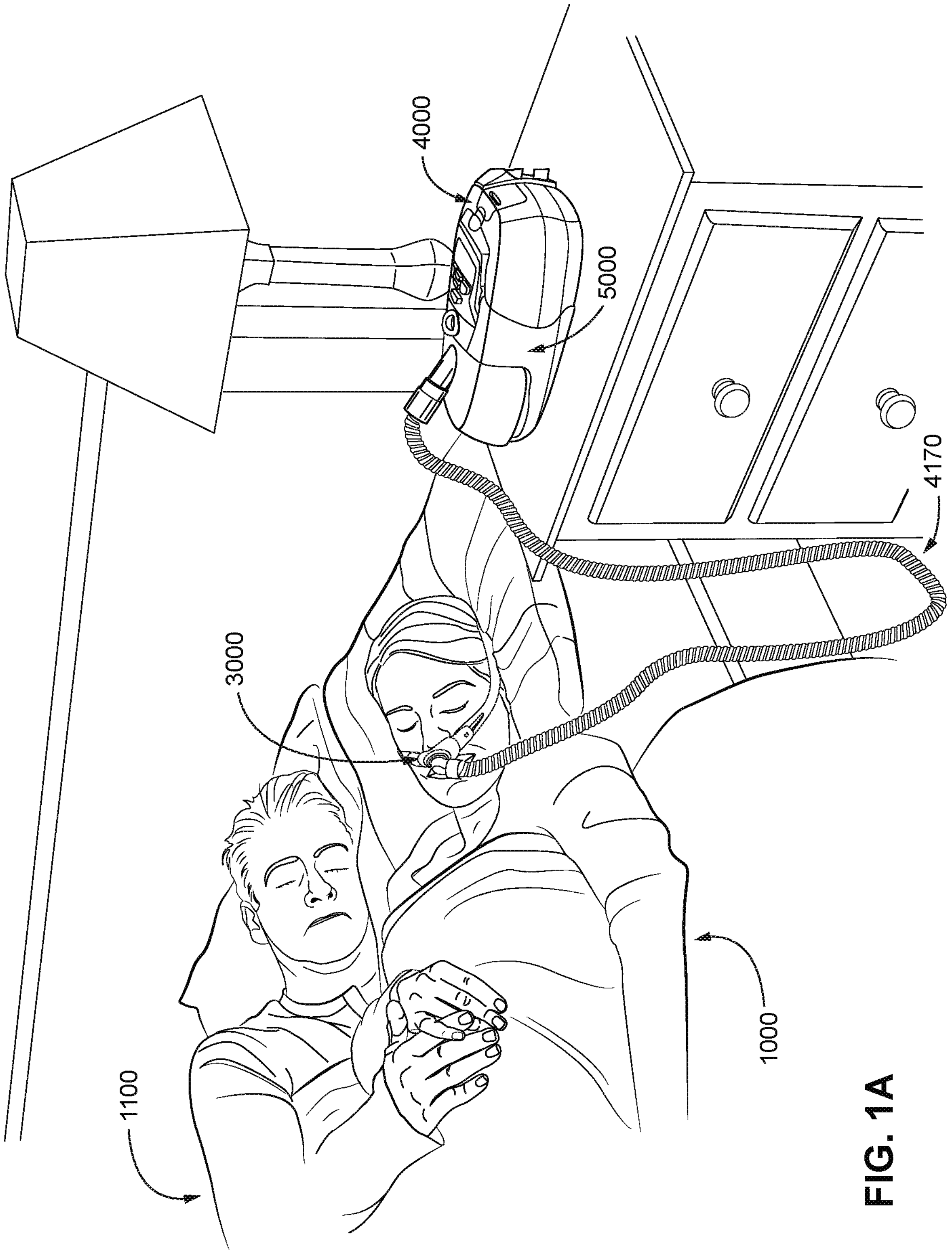
Figure 1B:
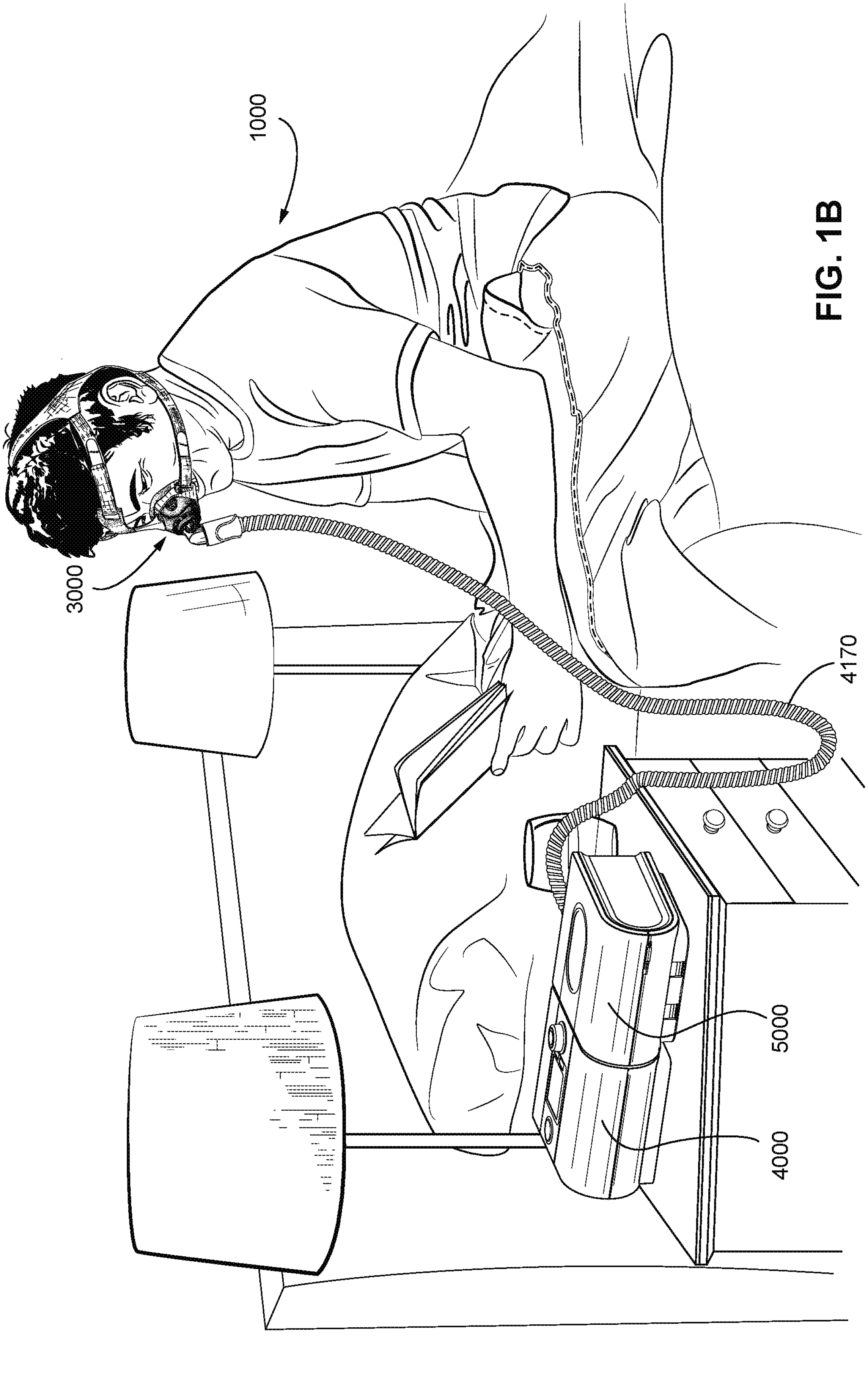
Figure 1C:
Figure 2A:
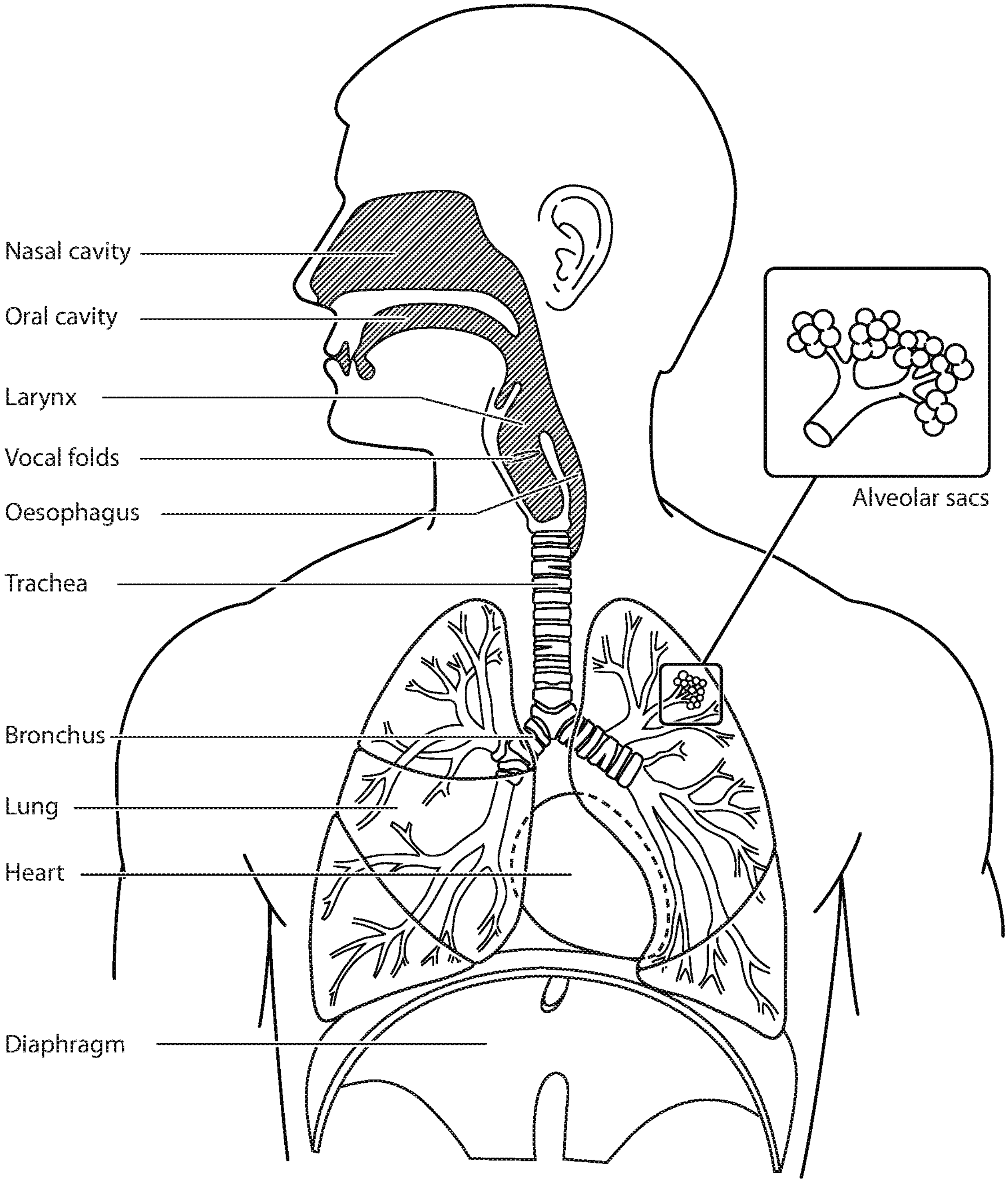
FIG. 2A shows an overview of a human respiratory system including the nasal and oral cavities, the larynx, vocal folds, oesophagus, trachea, bronchus, lung, alveolar sacs, heart and diaphragm.
Figure 2B:
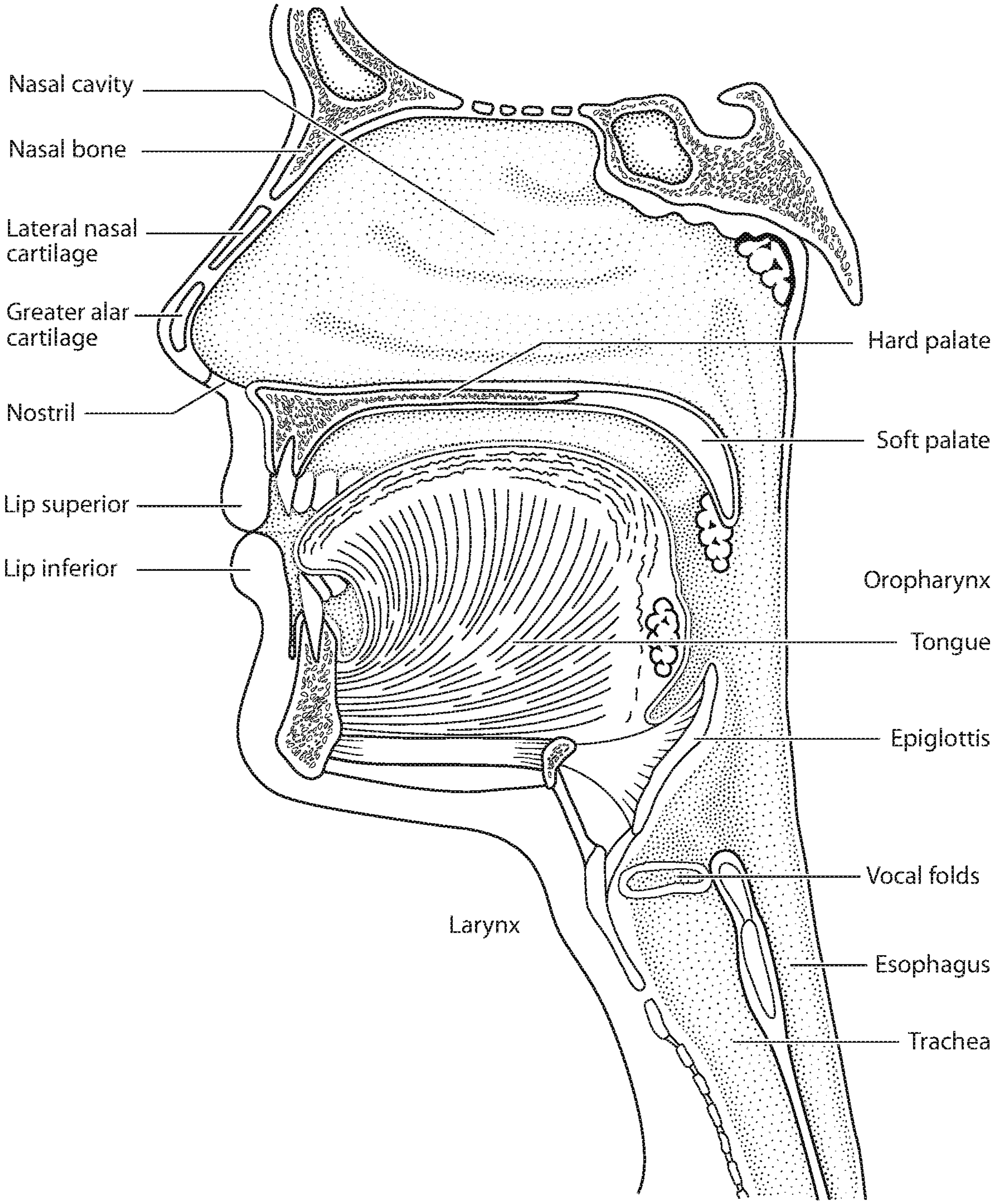
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
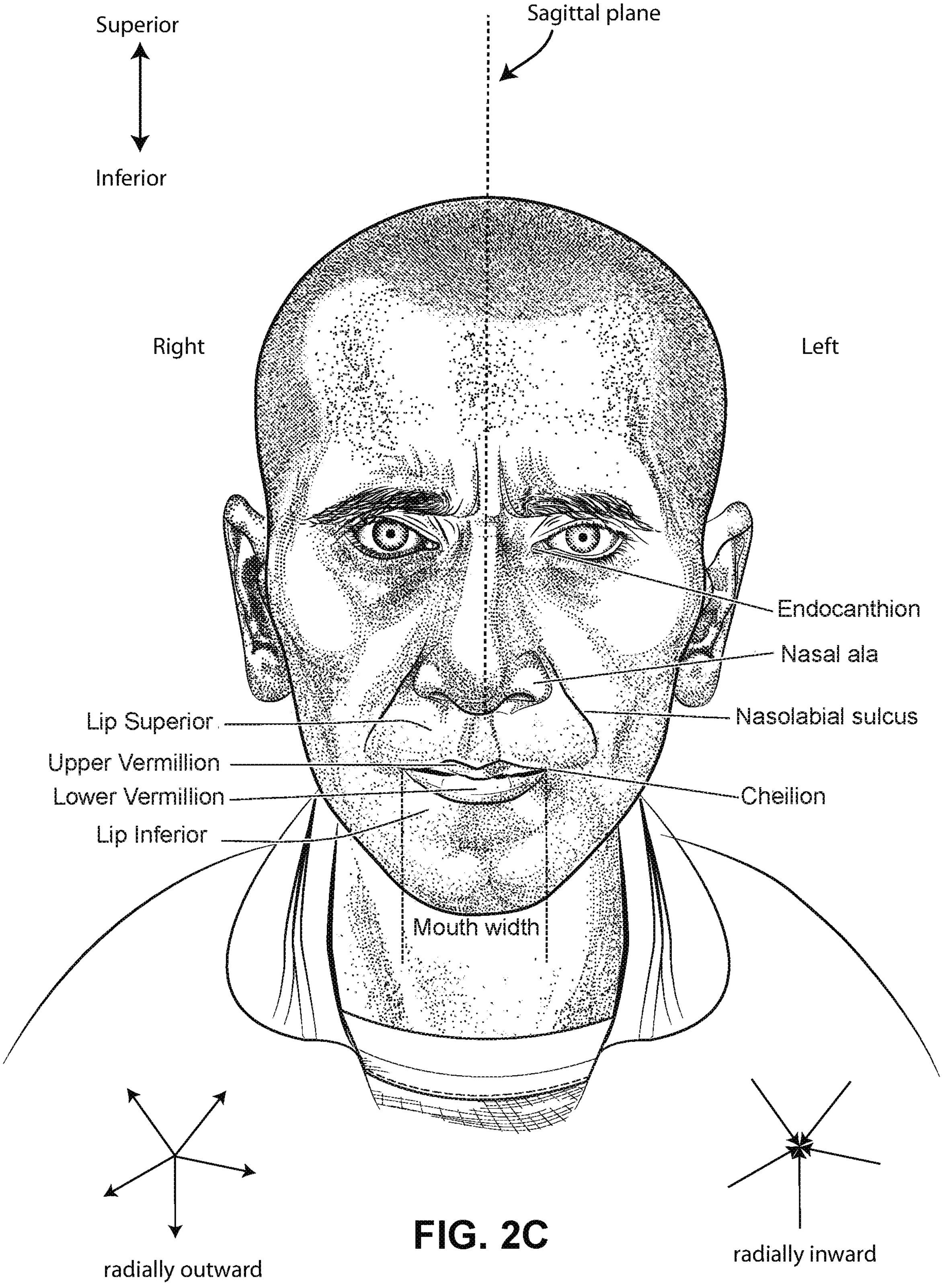
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
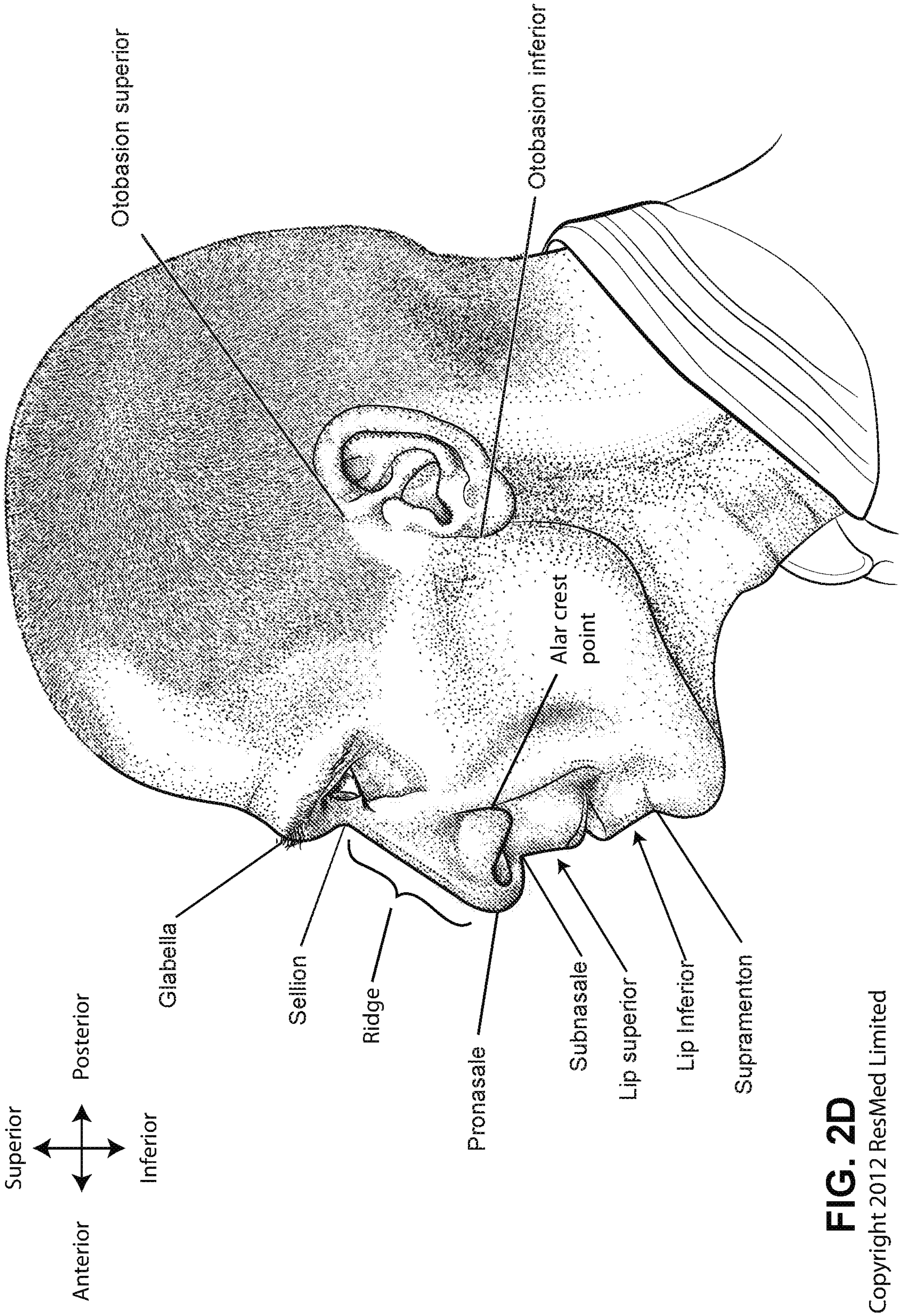
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
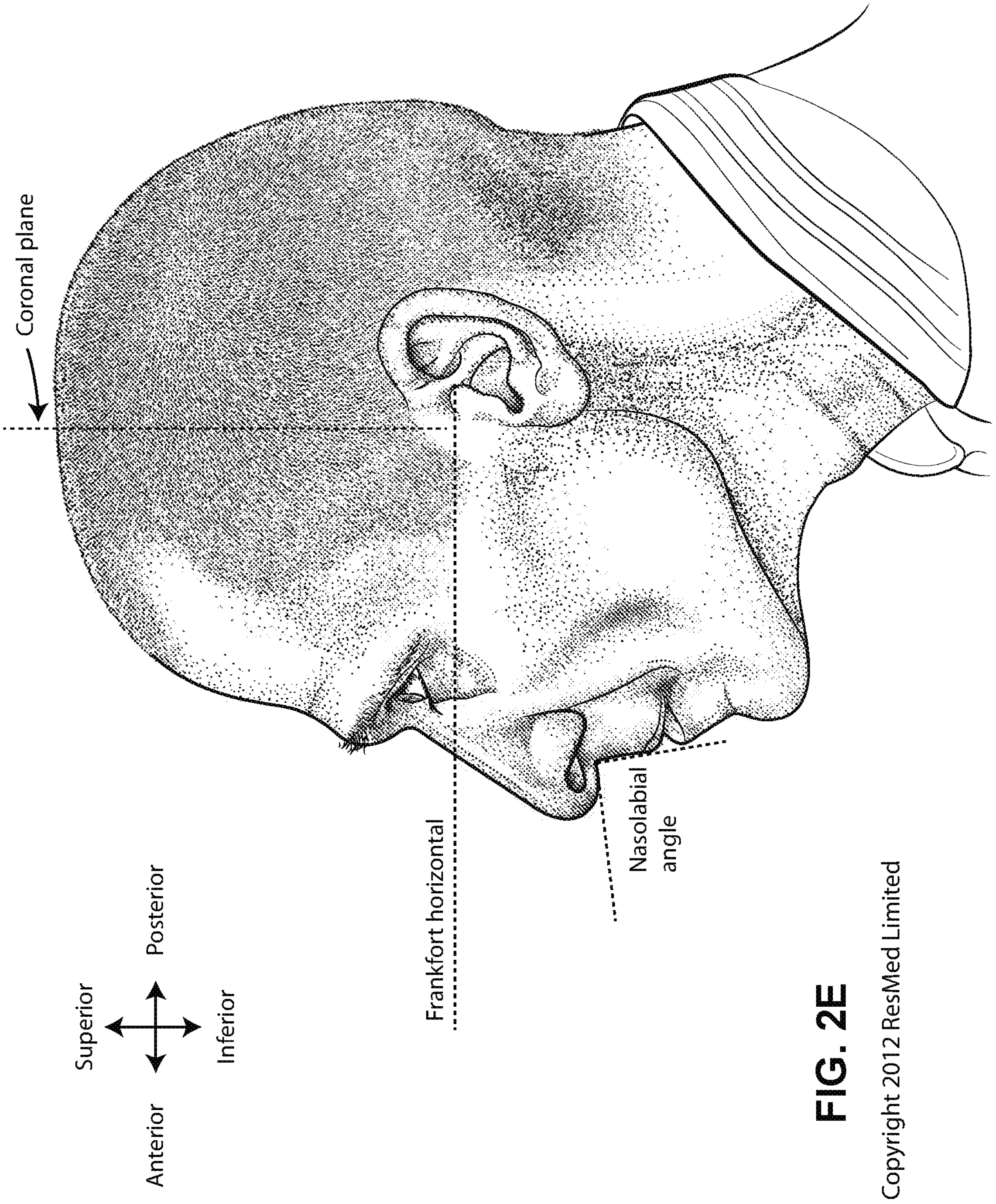

FIG. 2E is a further side view of a head. The approximate locations of the Frankfort horizontal and nasolabial angle are indicated. The coronal plane is also indicated.

Figure 2F:
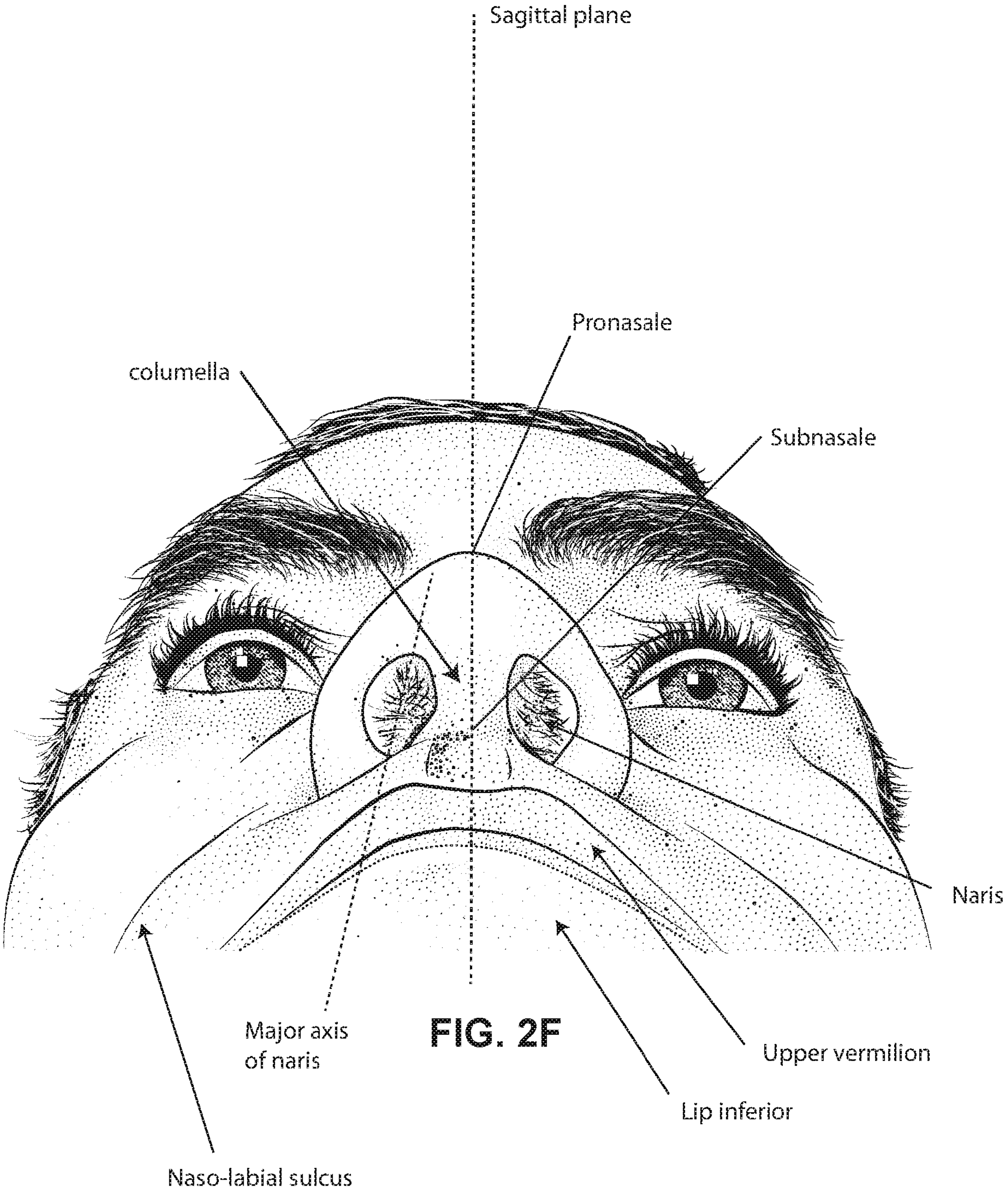

FIG. 2F shows a base view of a nose with several features identified including naso-labial sulcus, lip inferior, upper Vermilion, naris, subnasale, columella, pronasale, the major axis of a naris and the midsagittal plane.

Figure 2G:

FIG. 2G shows a side view of the superficial features of a nose.

Figure 2H:
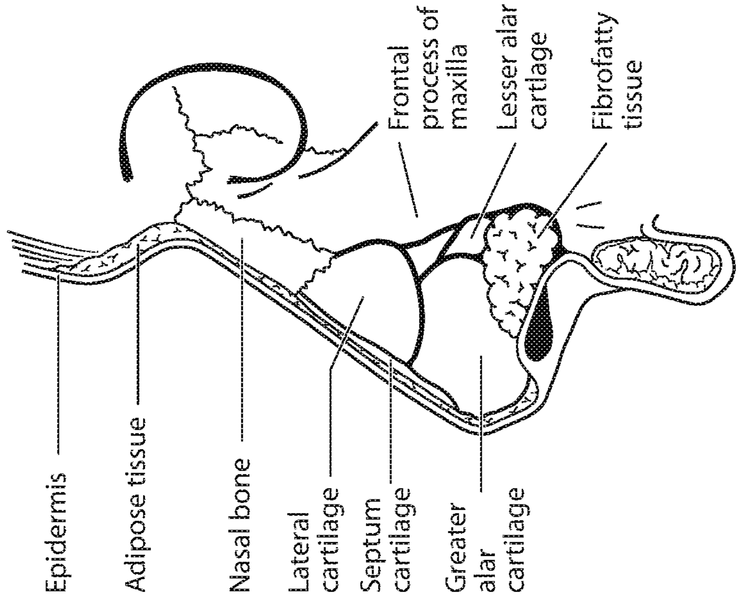

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

Figure 2I:
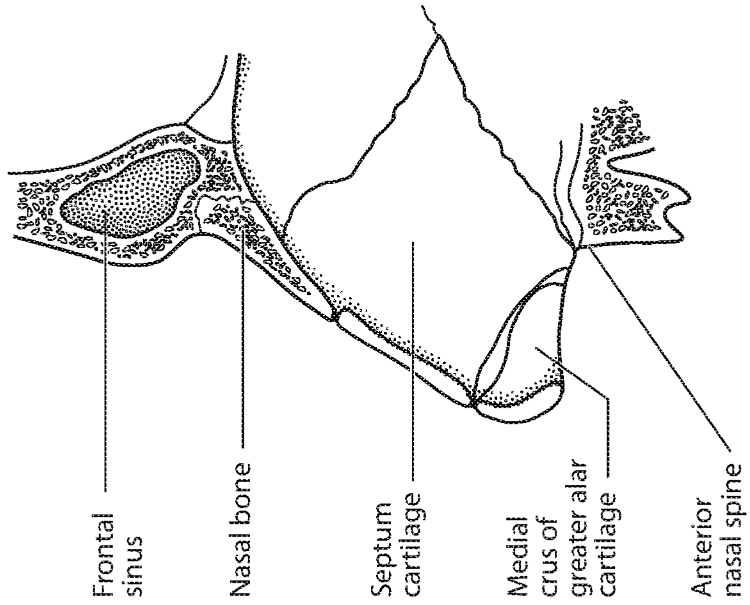

FIG. 2I shows a medial dissection of a nose, approximately several millimeters from the midsagittal plane, amongst other things showing the septum cartilage and medial crus of greater alar cartilage.

Figures 2J, 2K:
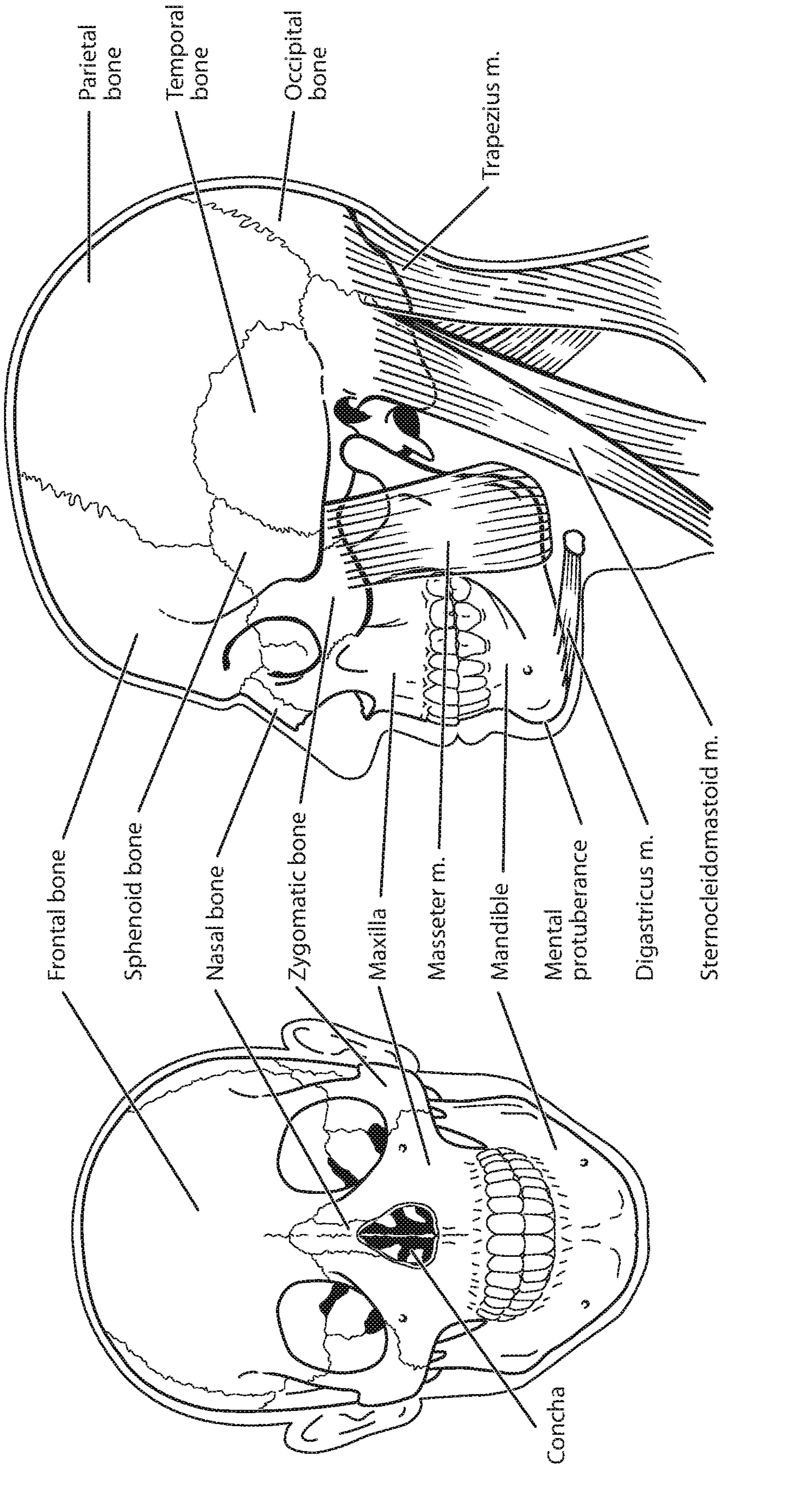

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
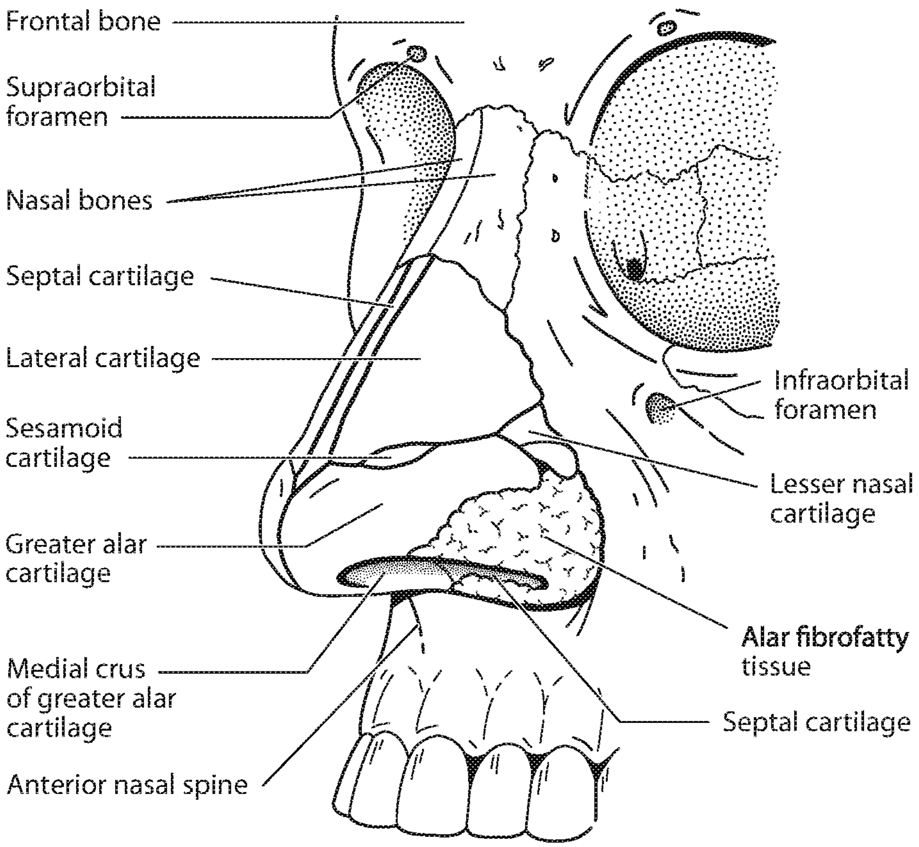

FIG. 2L shows an anterolateral view of a nose.

4.3 Patient Interface

Figure 3A:
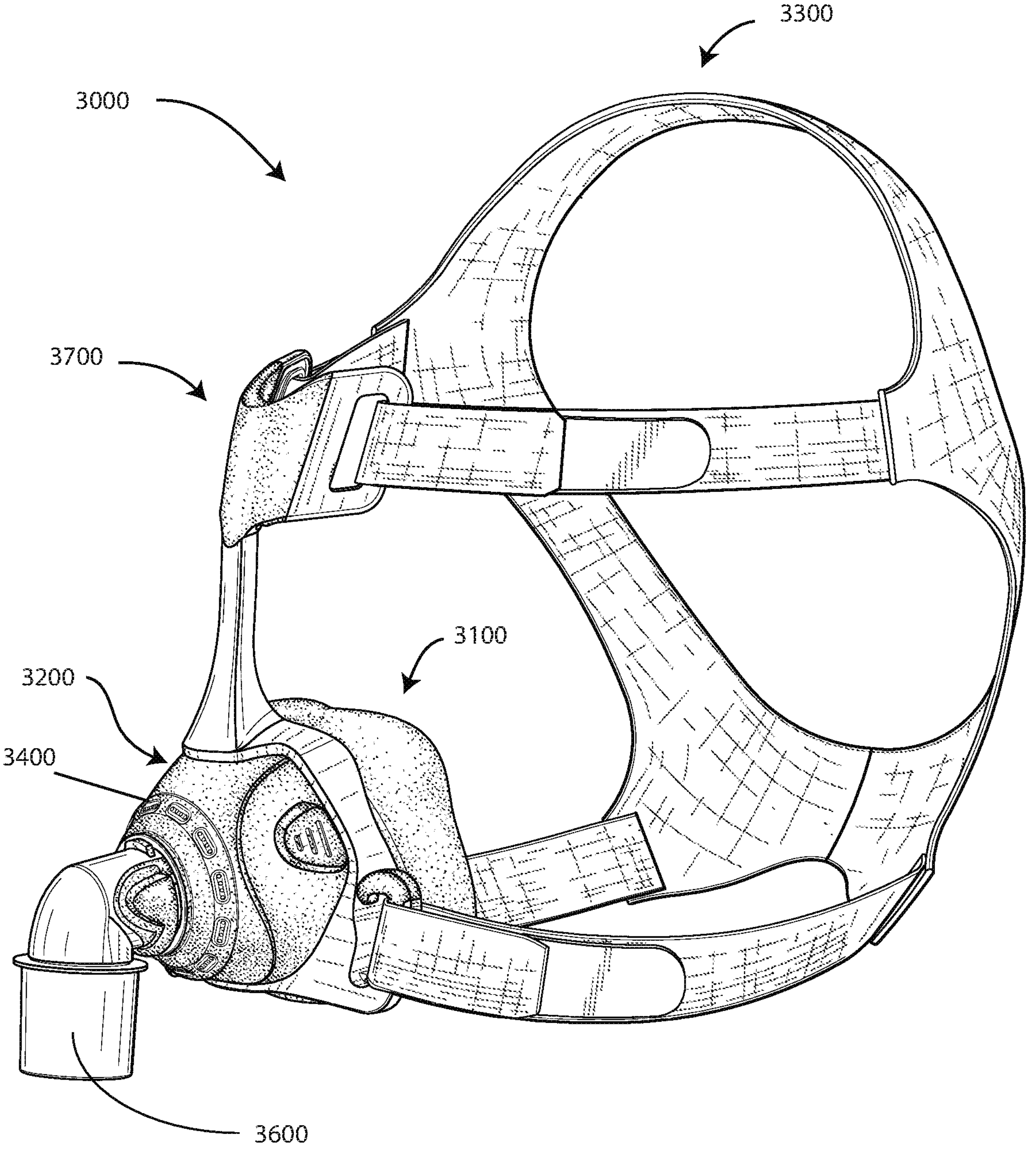

FIG. 3A shows a patient interface in the form of a nasal mask in accordance with one form of the present technology.

Figure 3B:
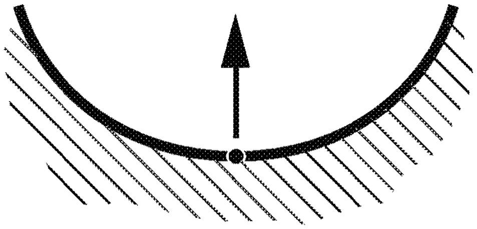

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
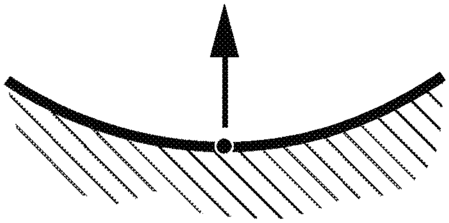

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
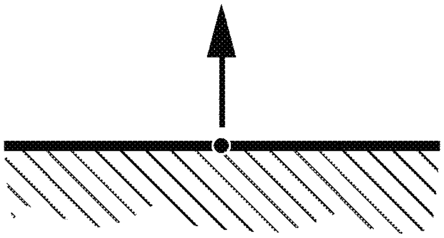

FIG. 3D shows a schematic of a cross-section through a structure at a point. An outward normal at the point is indicated. The curvature at the point has a value of zero.

Figure 3E:
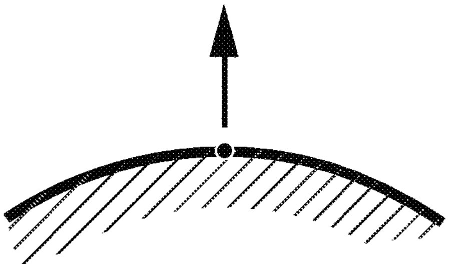

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
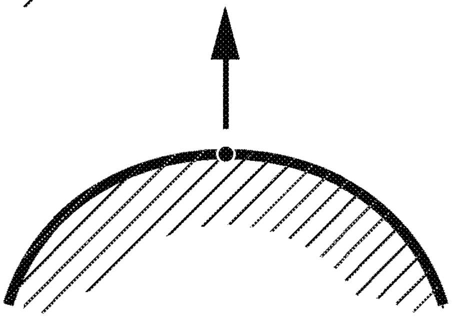

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
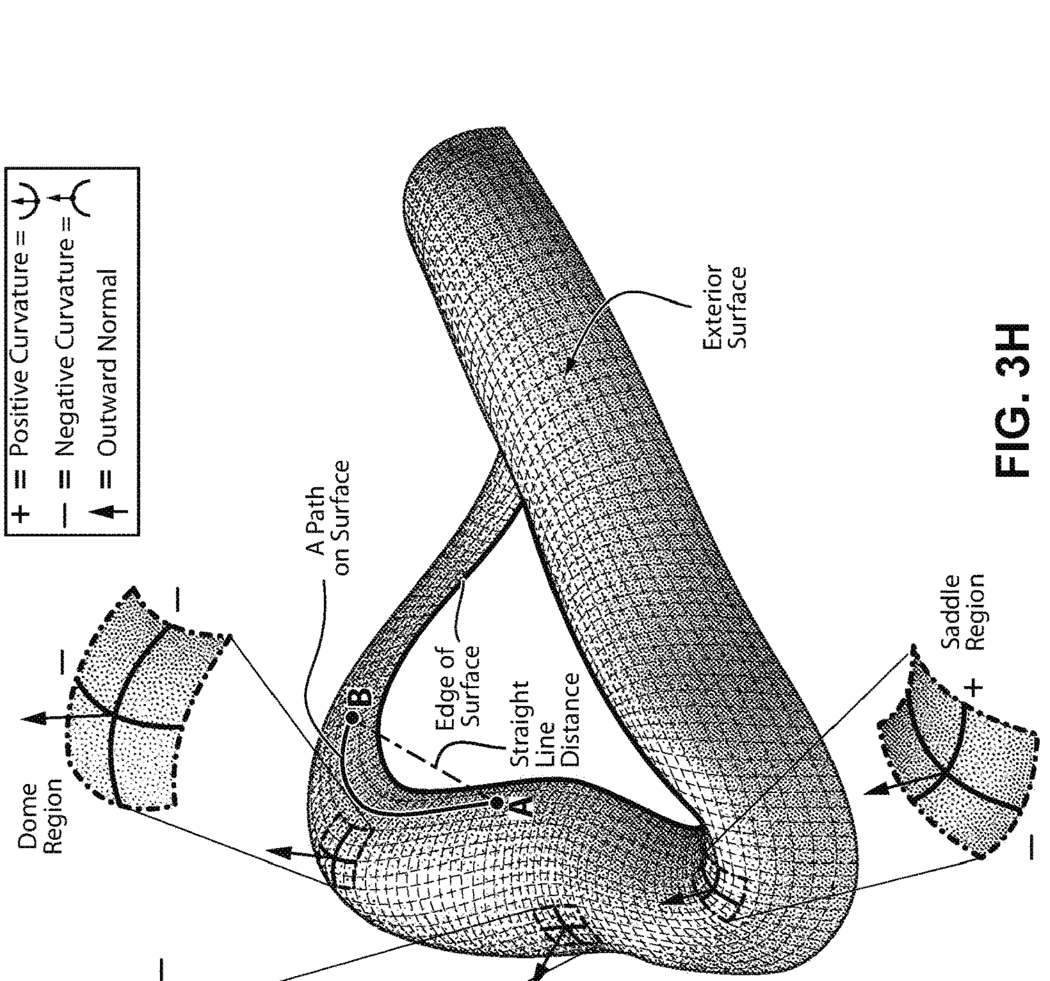
Figure 3G:
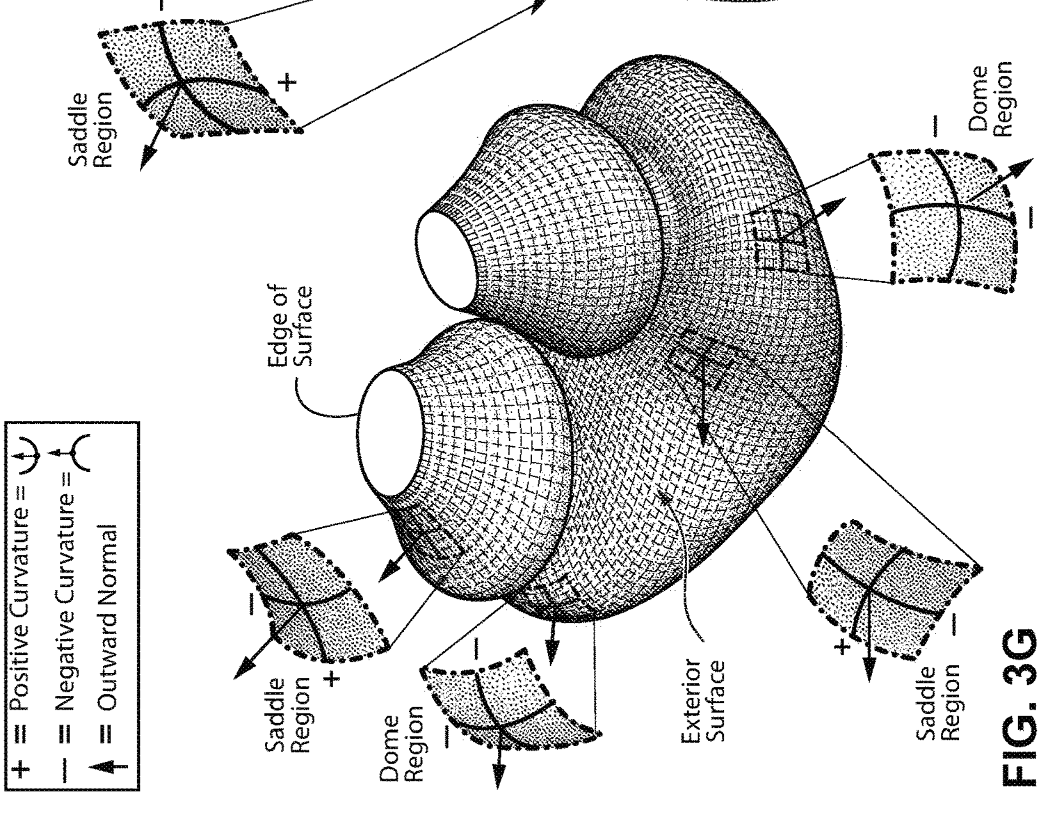

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
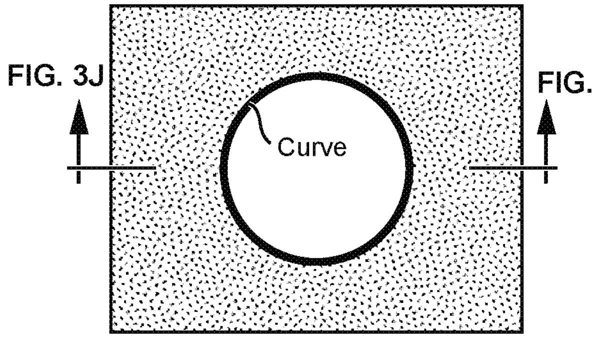

FIG. 3I shows the surface of a structure, with a one dimensional hole in the surface. The illustrated plane curve forms the boundary of a one dimensional hole.

Figure 3K:
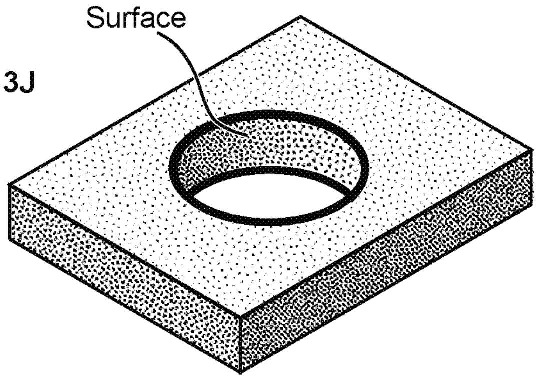
Figure 3J:
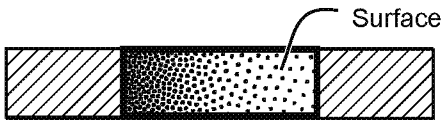

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
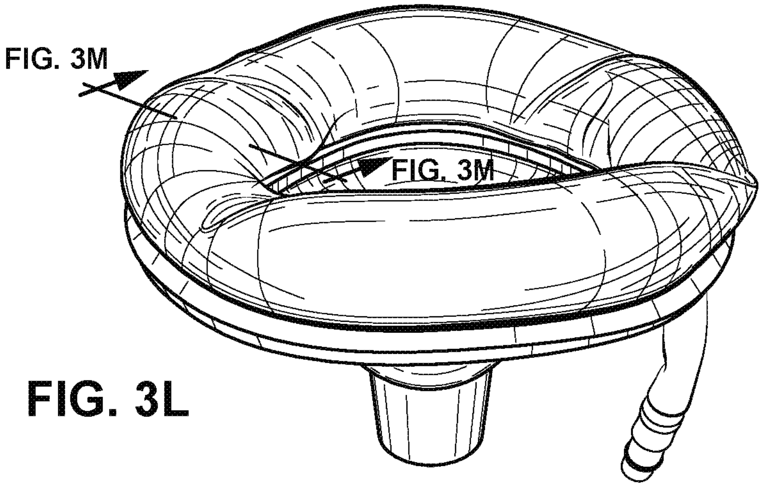

FIG. 3L shows a mask having an inflatable bladder as a cushion.

Figure 3M:
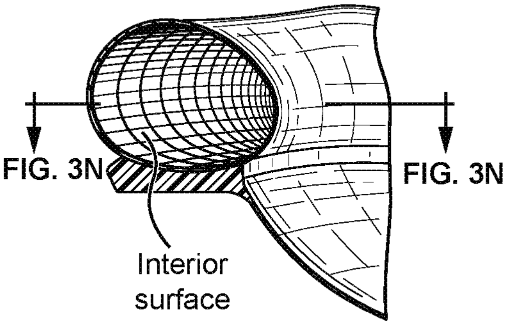

FIG. 3M shows a cross-section through the mask of FIG. 3L, and shows the interior surface of the bladder. The interior surface bounds the two dimensional hole in the mask.

Figure 3N:
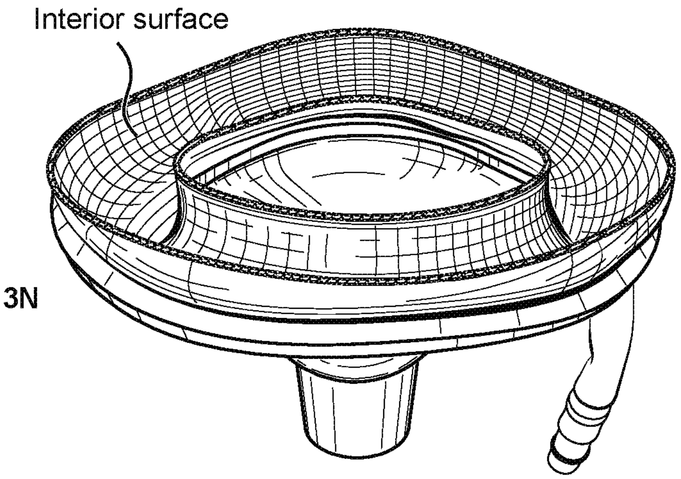

FIG. 3N shows a further cross-section through the mask of FIG. 3L. The interior surface is also indicated.

Figure 3O:
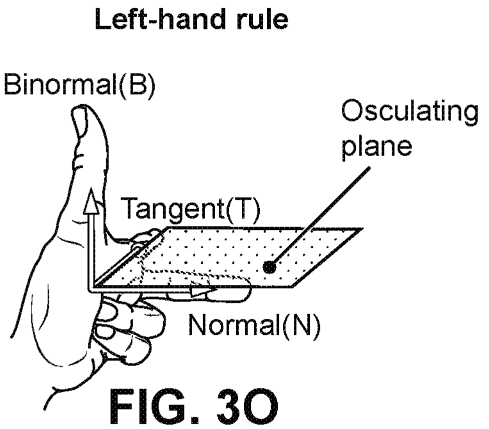

FIG. 3O illustrates a left-hand rule.

Figure 3P:
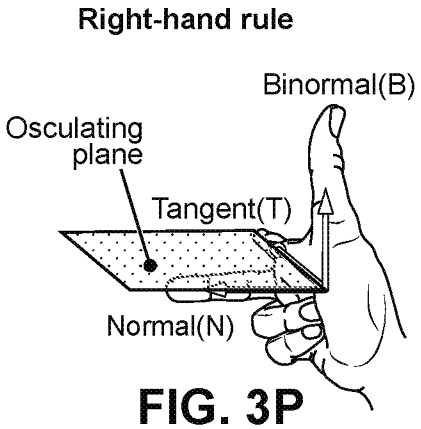

FIG. 3P illustrates a right-hand rule.

Figure 3Q:

FIG. 3Q shows a left ear, including the left ear helix.

Figure 3S:
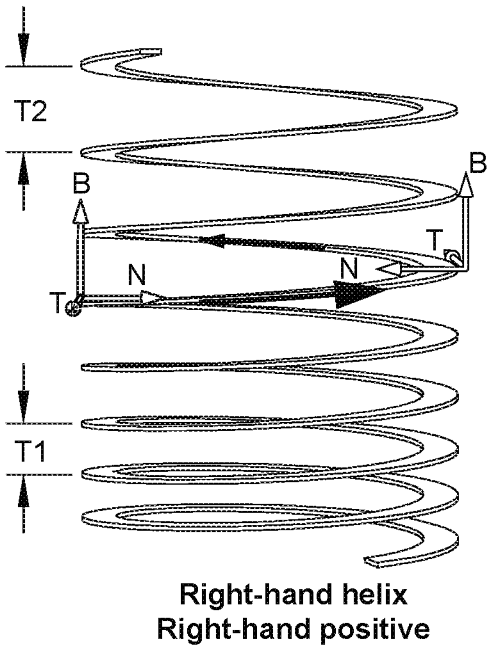
Figure 3R:

FIG. 3R shows a right ear, including the right ear helix.

FIG. 3S shows a right-hand helix.

Figure 3T:
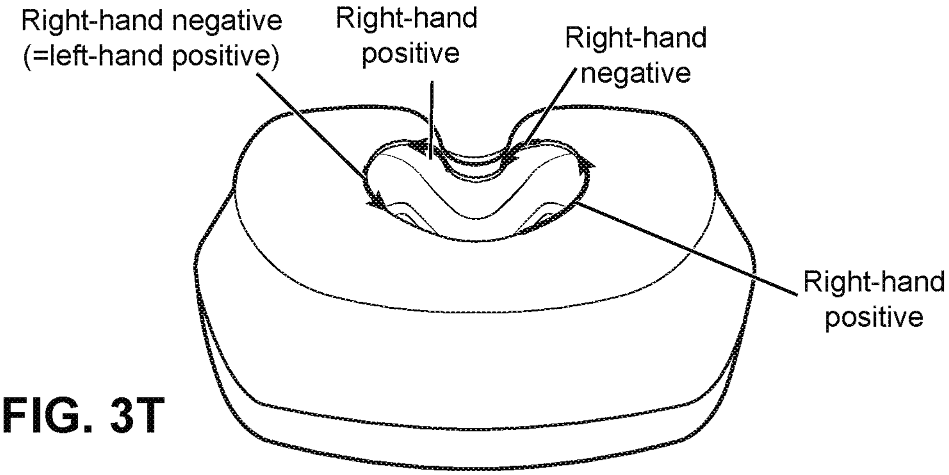

FIG. 3T shows a view of a mask, including the sign of the torsion of the space curve defined by the edge of the sealing membrane in different regions of the mask.

Figure 3U:
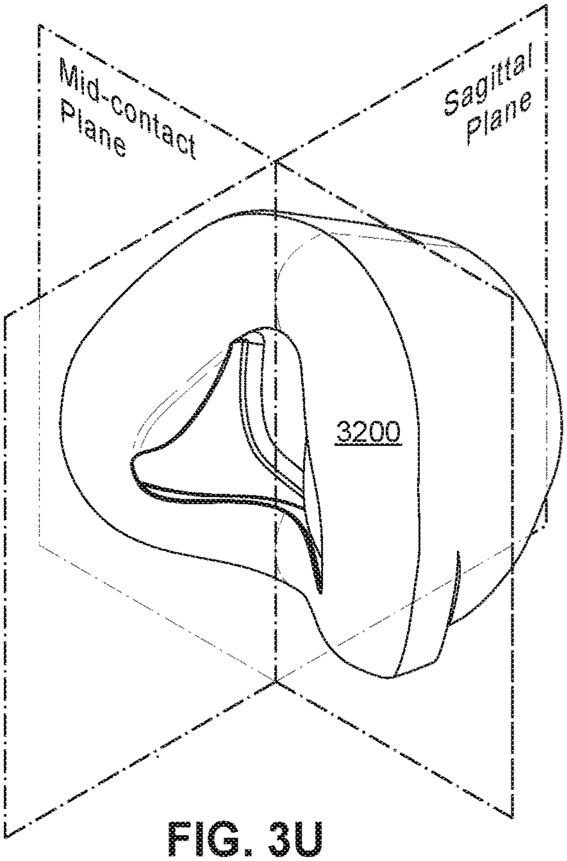

FIG. 3U shows a view of a plenum chamber 3200 showing a sagittal plane and a mid-contact plane.

Figure 3V:
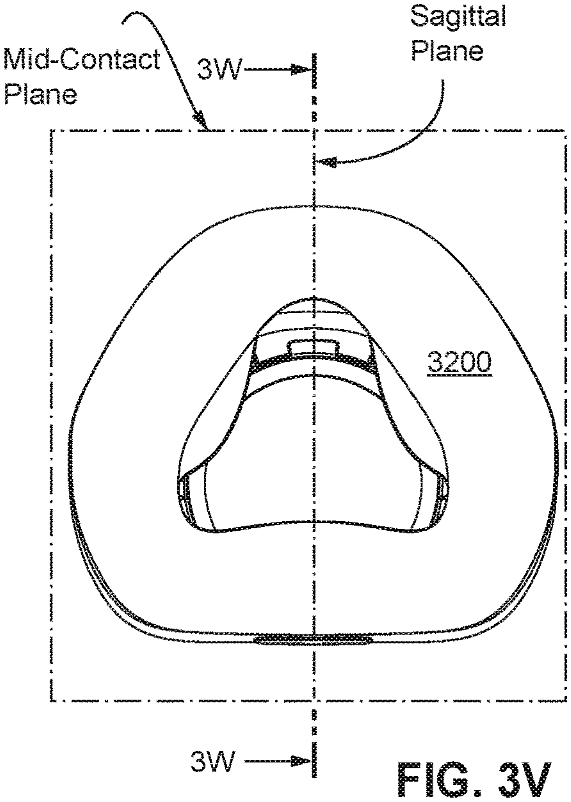

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
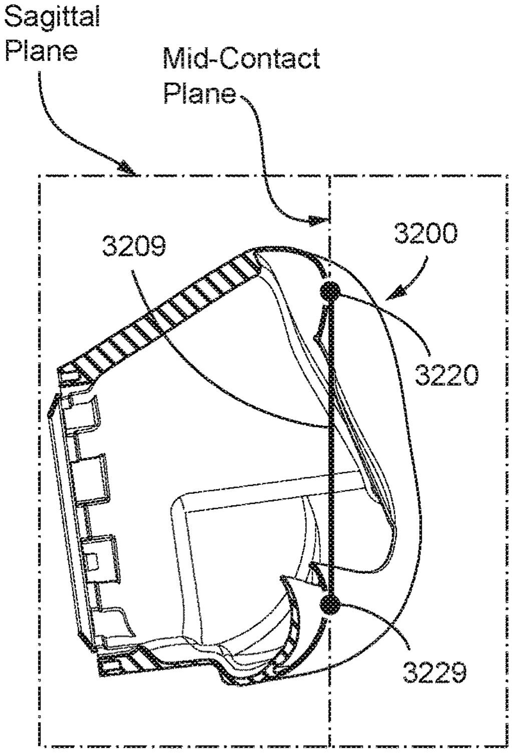

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3229. Depending on the geometry of the cushion in this region, the mid-contact plane may be a tangent at both the superior and inferior points.

Figure 3X:
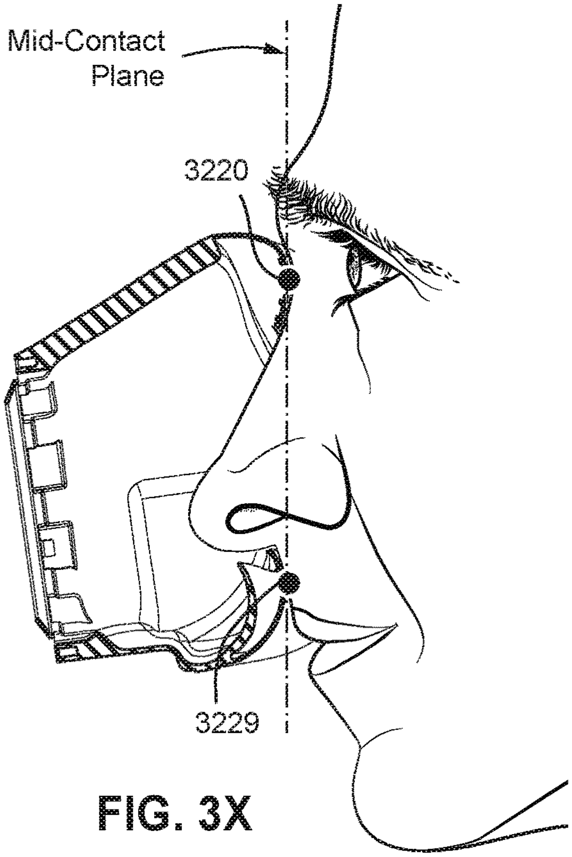

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3229 sits on the lip superior.

4.4 RPT Device

Figure 4A:
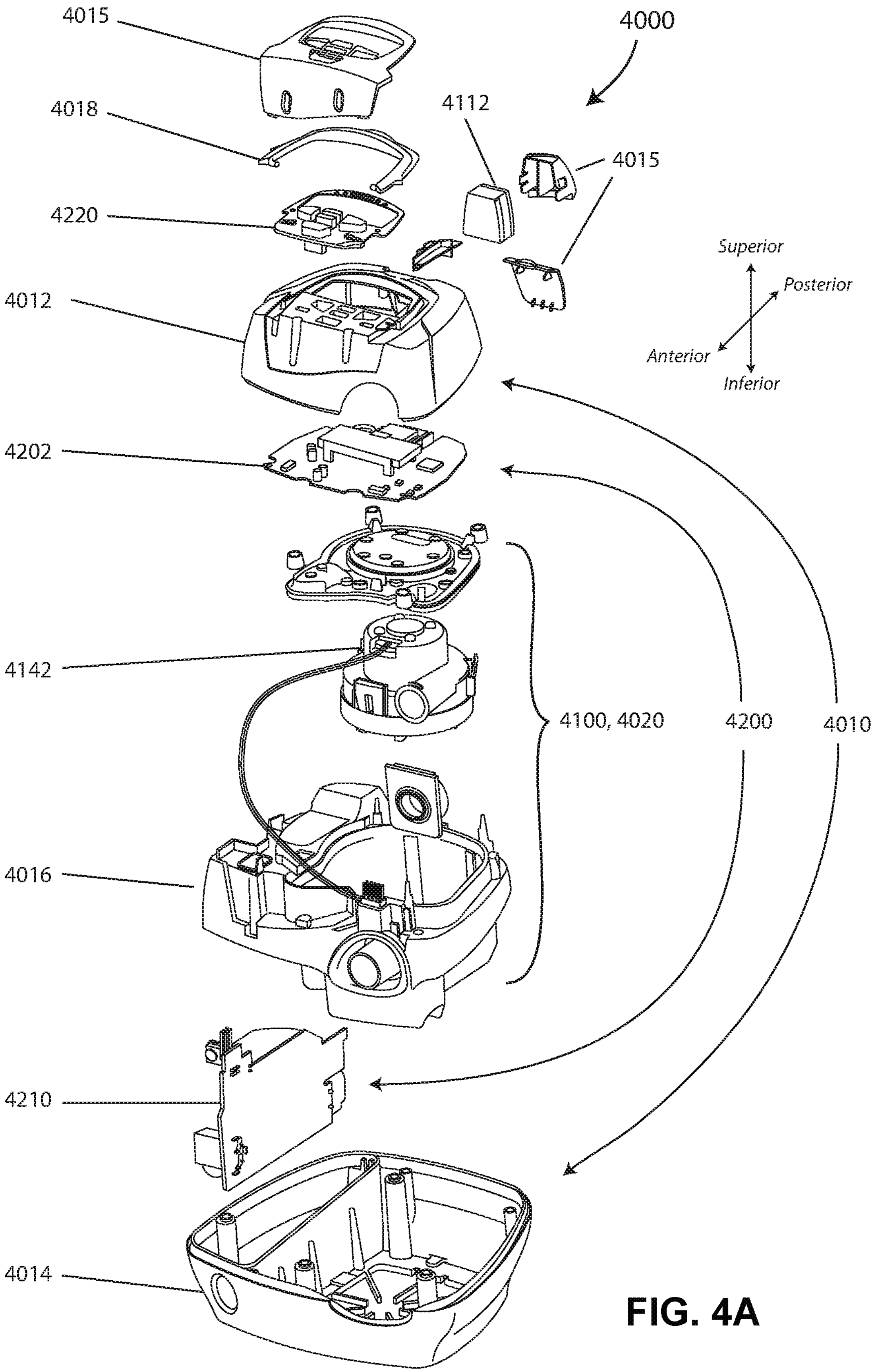

FIG. 4A shows an RPT device in accordance with one form of the present technology.

Figure 4B:
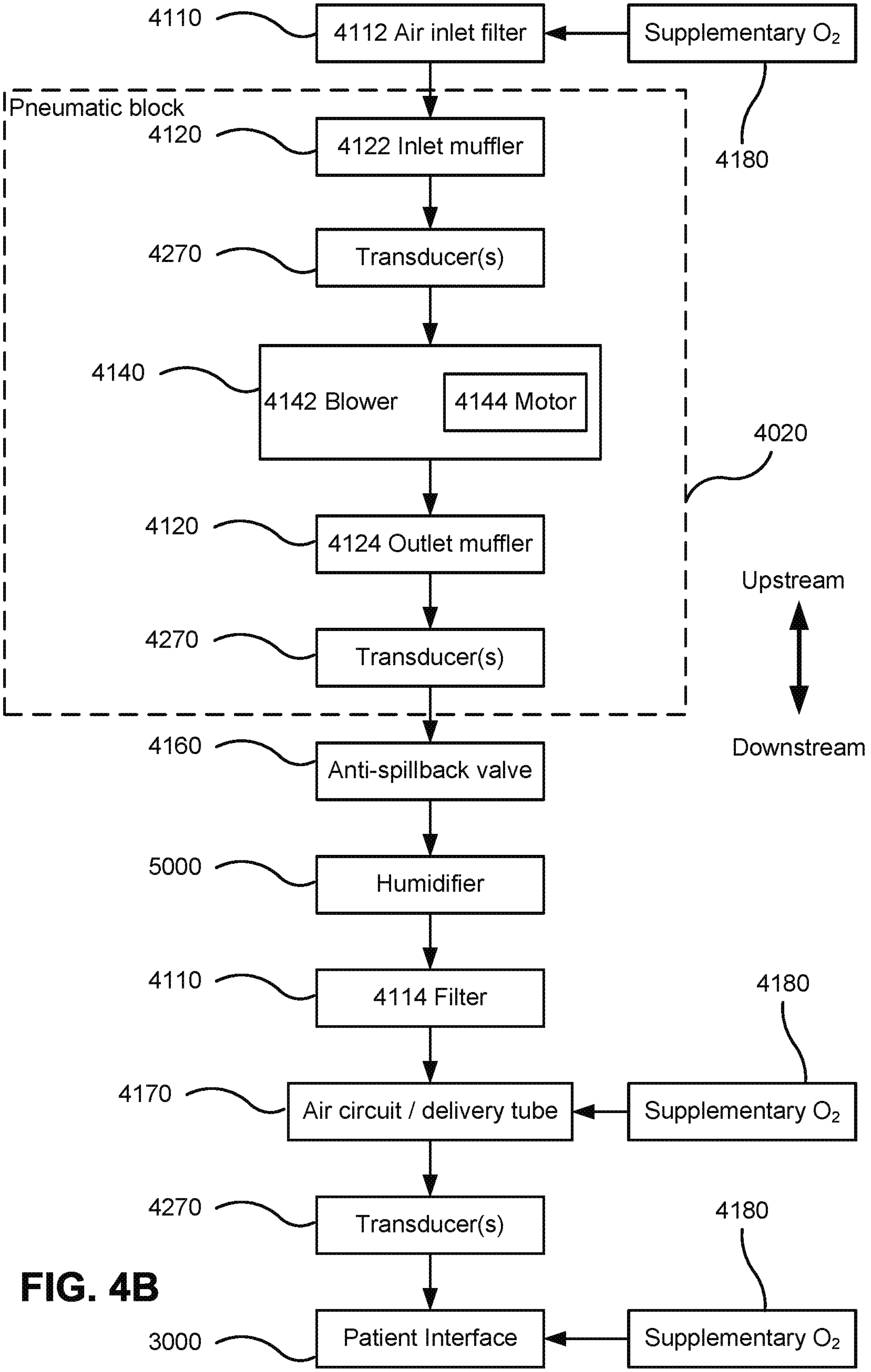

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 4C:
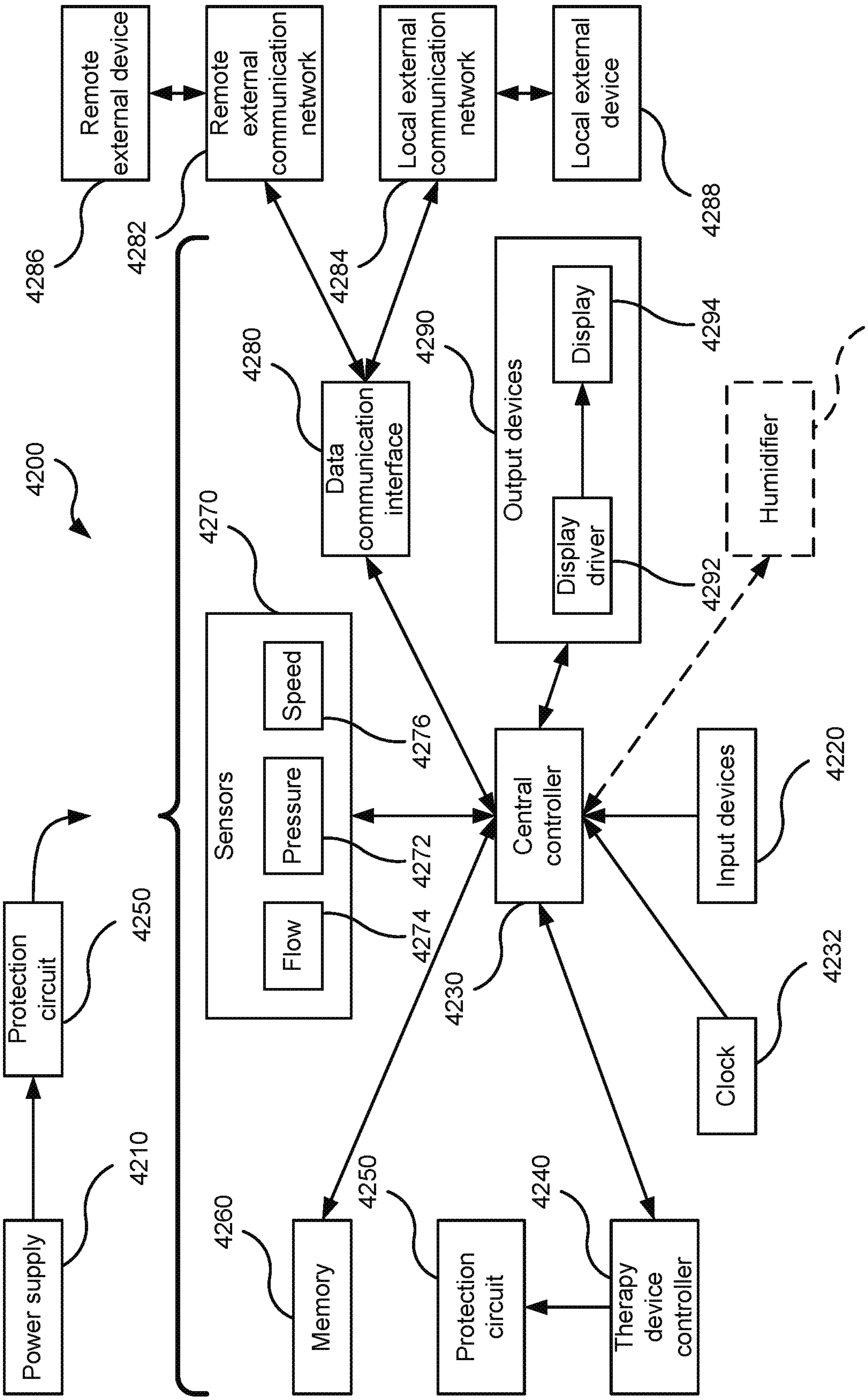

FIG. 4C is a schematic diagram of the electrical components of an RPT device in accordance with one form of the present technology.

4.5 Humidifier

Figure 5A:
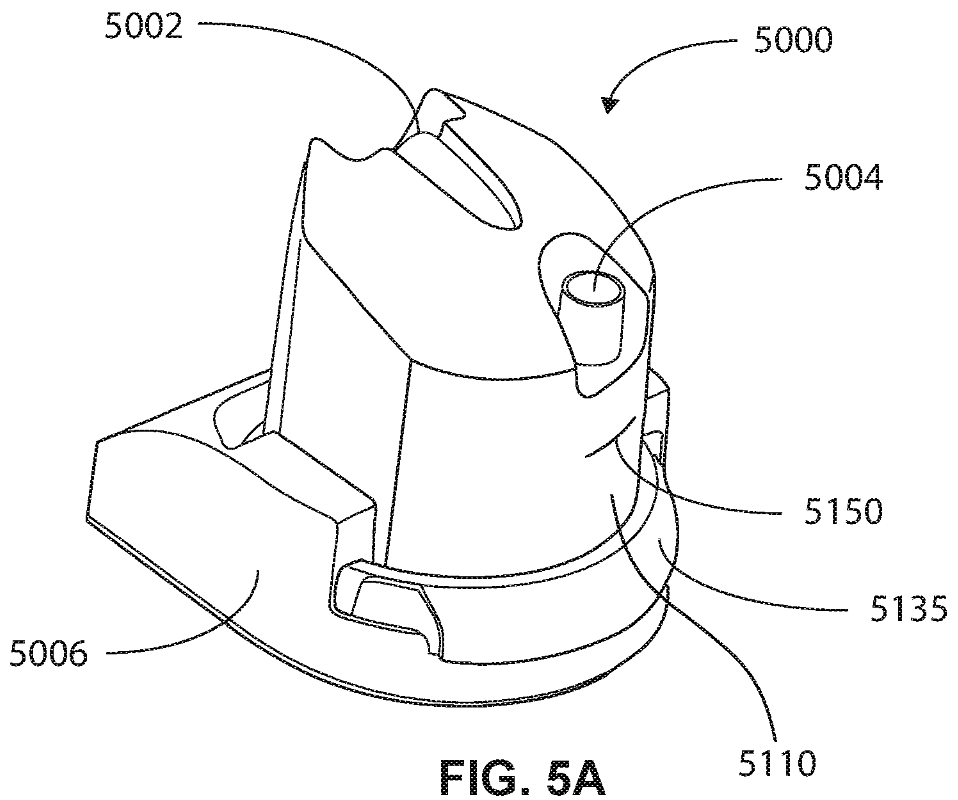

FIG. 5A shows an isometric view of a humidifier in accordance with one form of the present technology.

Figure 5B:
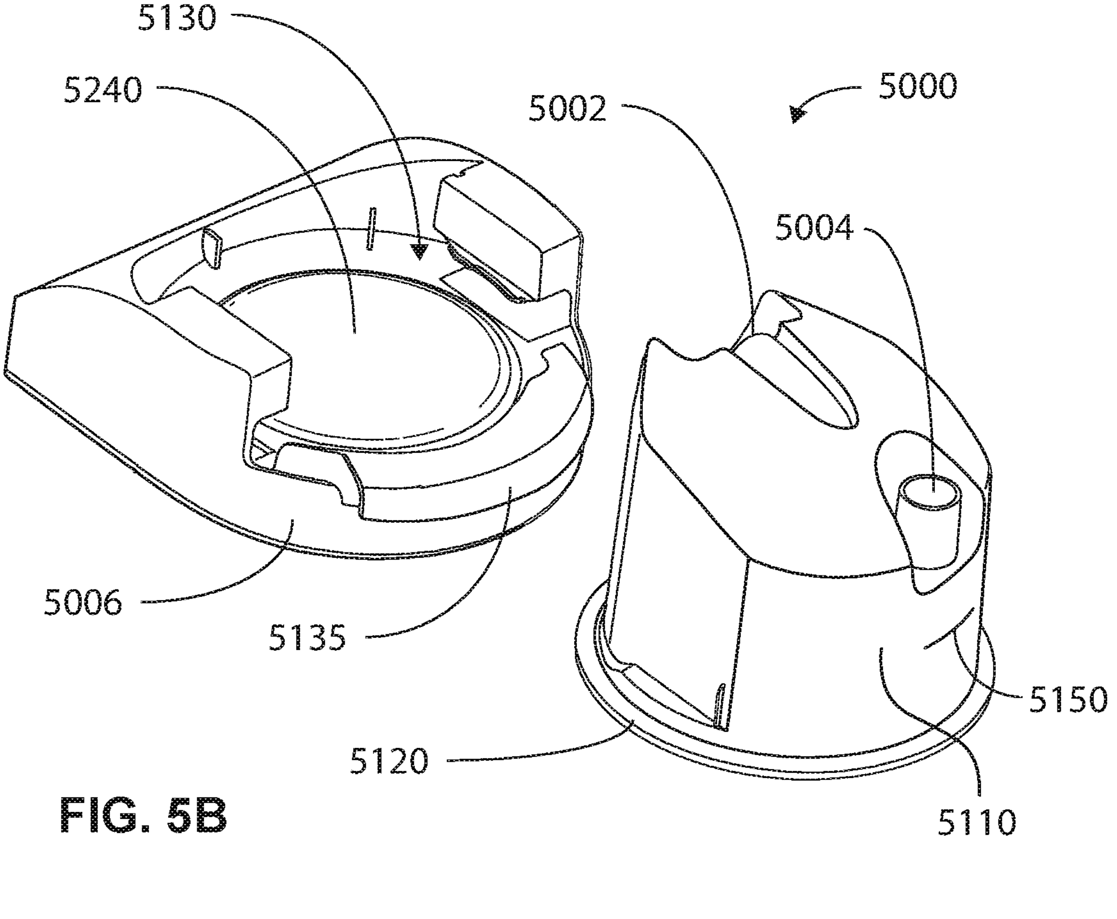

FIG. 5B shows an isometric view of a humidifier in accordance with one form of the present technology, showing a humidifier reservoir 5110 removed from the humidifier reservoir dock 5130.

Figure 5C:
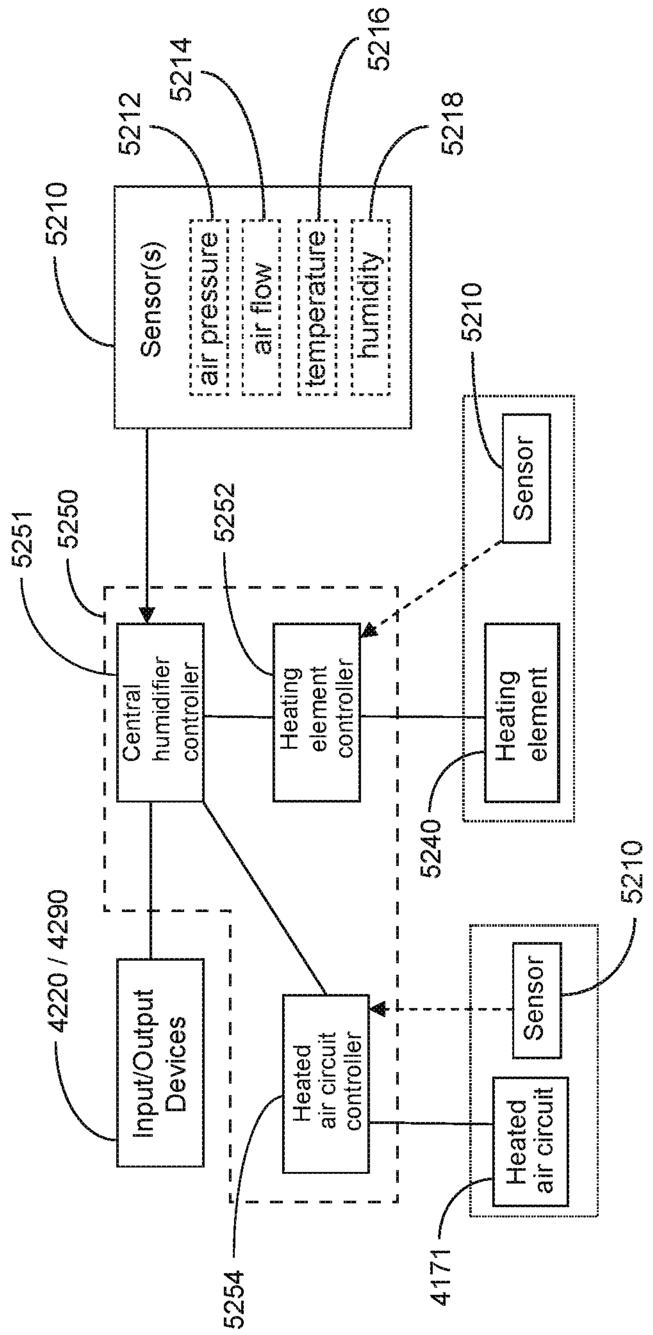

FIG. 5C shows a schematic of a humidifier in accordance with one form of the present technology.

4.6 Breathing Waveforms

Figure 6:
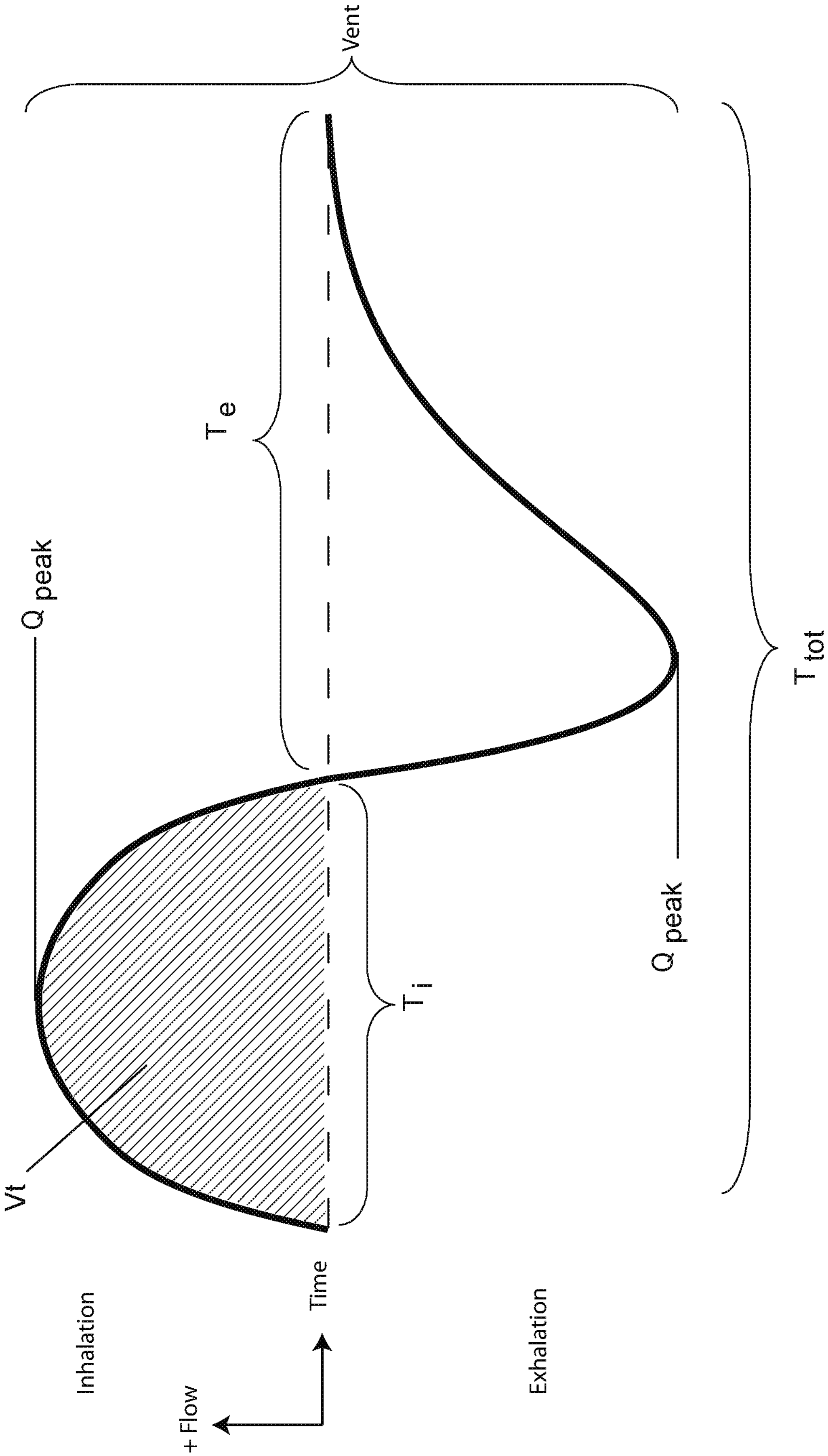

FIG. 6 shows a model typical breath waveform of a person while sleeping.

4.7 Examples of the Present Technology

Figures 1, 7:
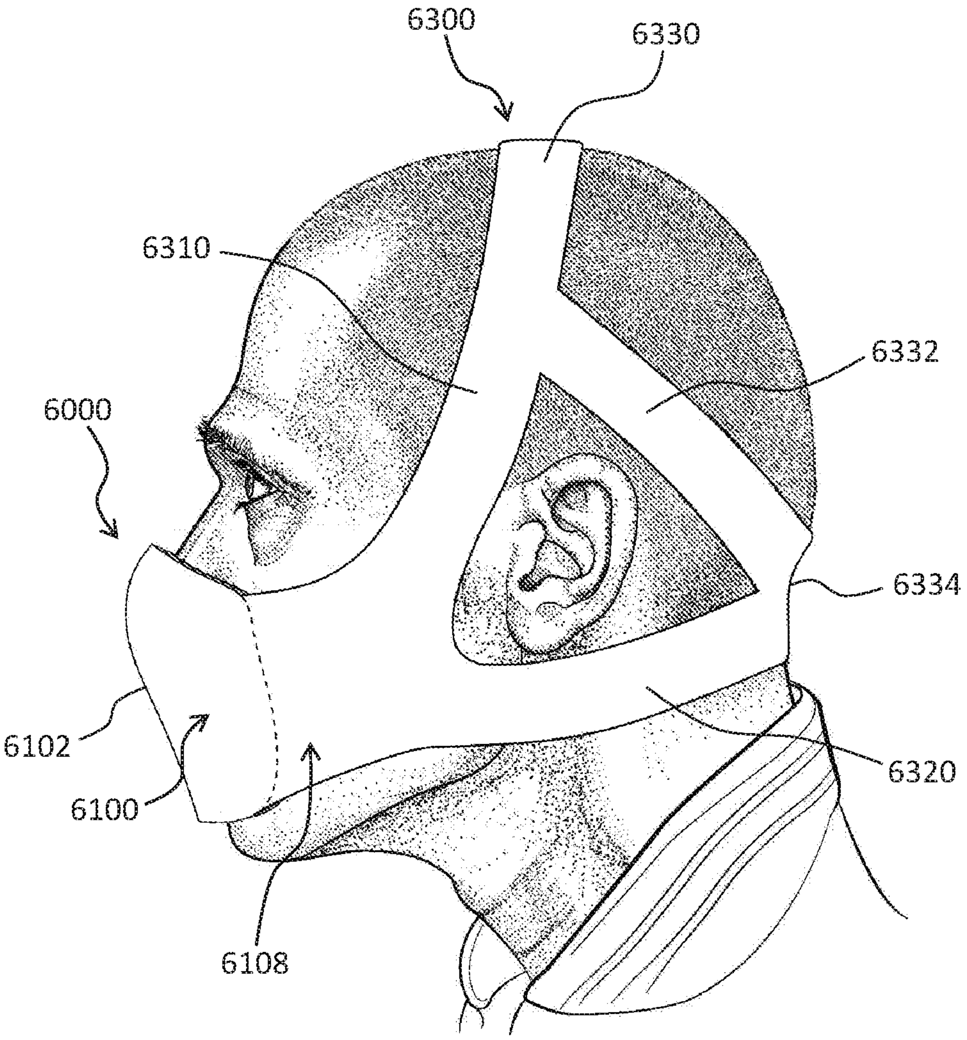

FIG. 7-1 is a side view of a patient interface 6000 according to an example of the present technology.

Figures 2, 7:
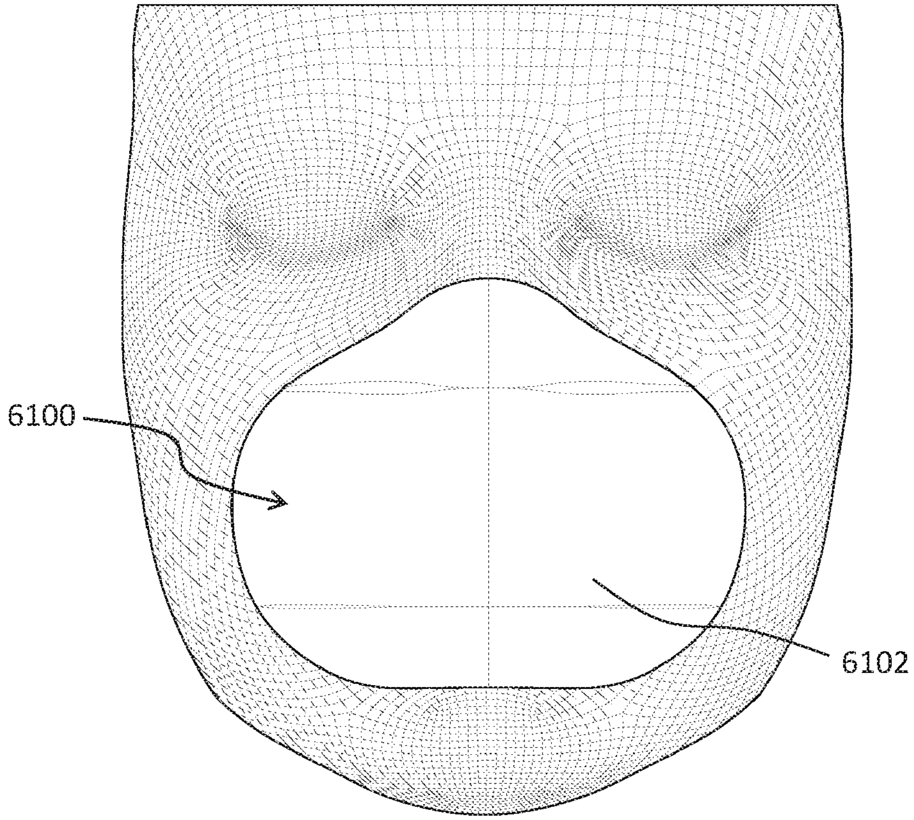

FIG. 7-2 is a front view of the patient interface of FIG. 7-1.

Figures 3, 7:
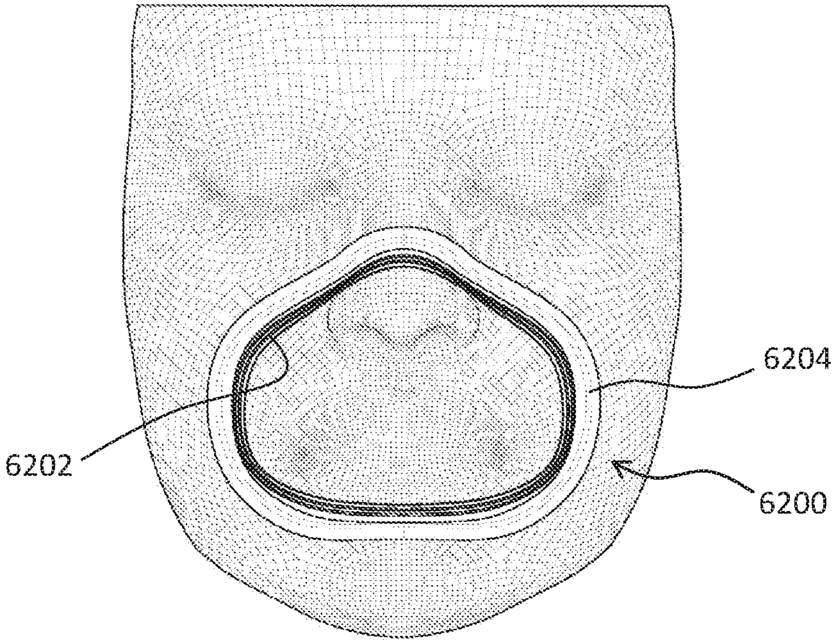

FIG. 7-3 is a front view of a seal-forming structure 6200 of the patient interface of FIG. 7-1 according to an example of the present technology.

Figures 4, 7:
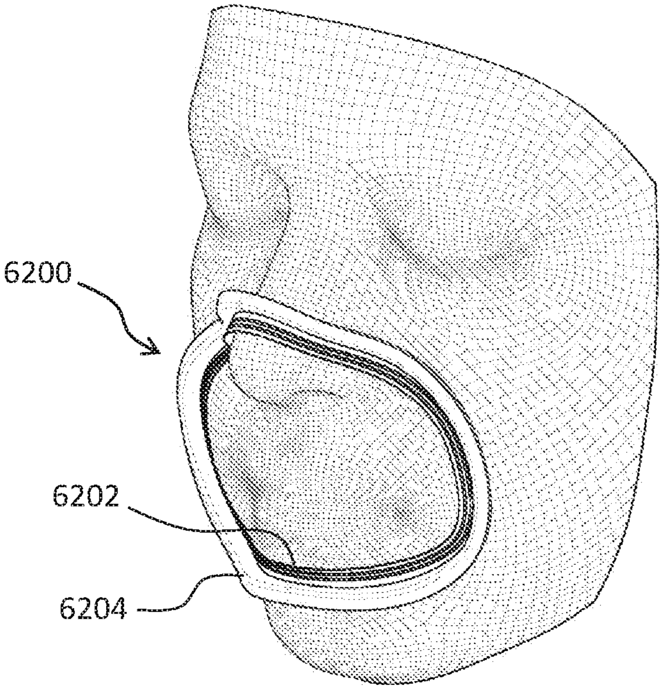

FIG. 7-4 is a perspective view of the seal-forming structure 6200 of the patient interface of FIG. 7-1.

Figures 5, 7:
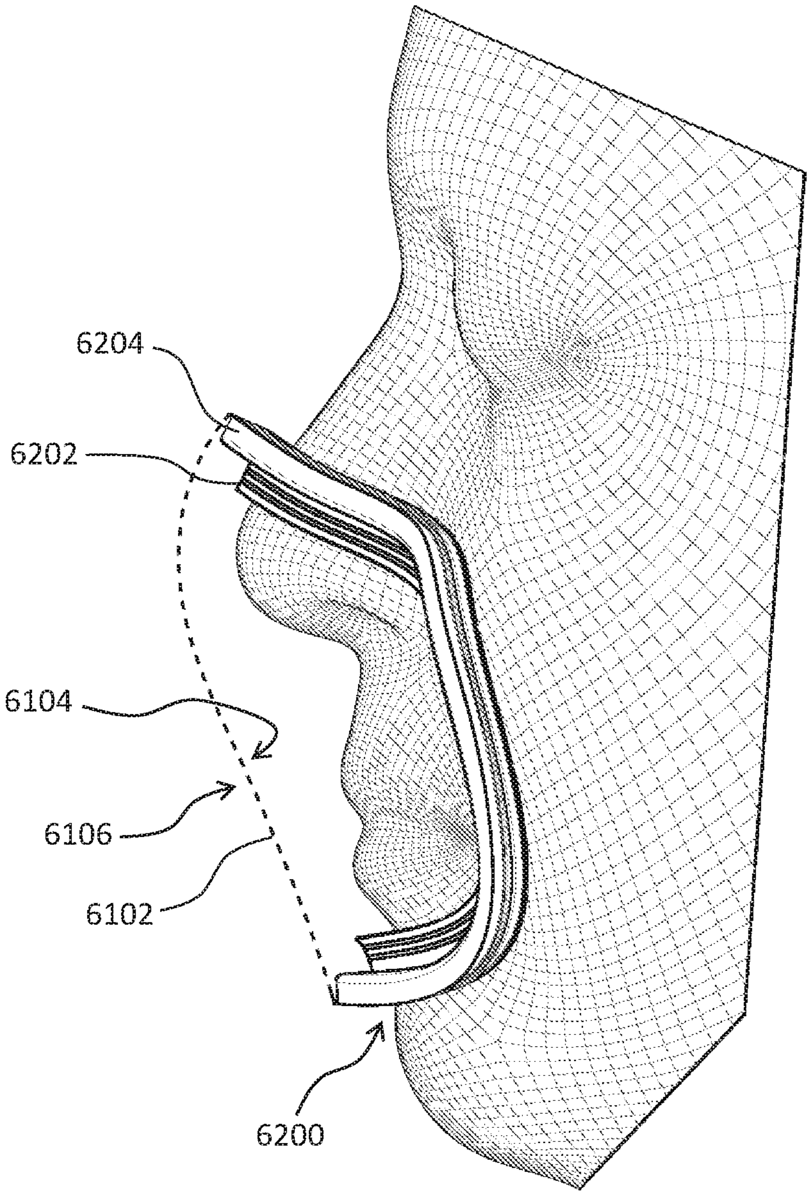

FIG. 7-5 is a side view of the seal-forming structure of the patient interface of FIG. 7-1.

Figures 1, 8:
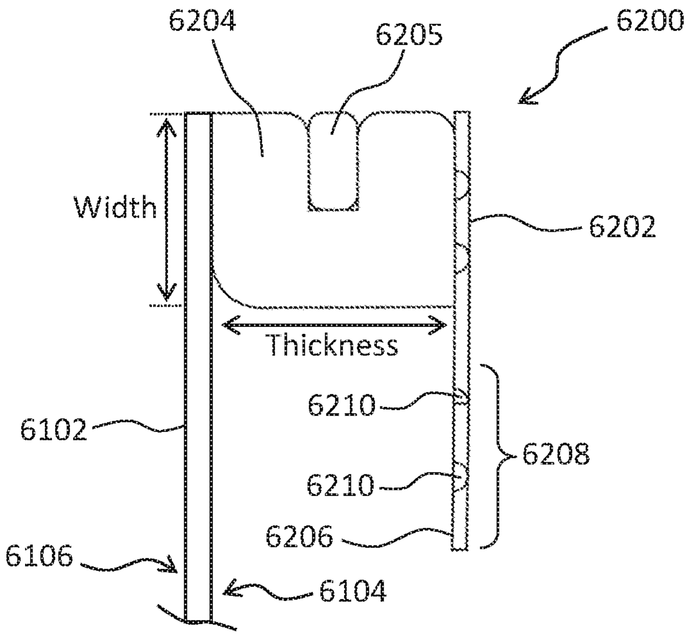
Figures 2, 8:
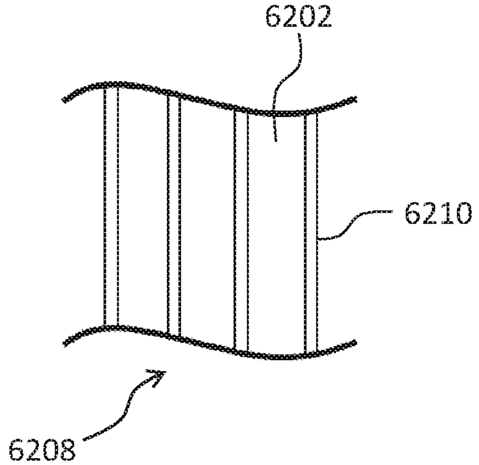
Figures 3, 8:
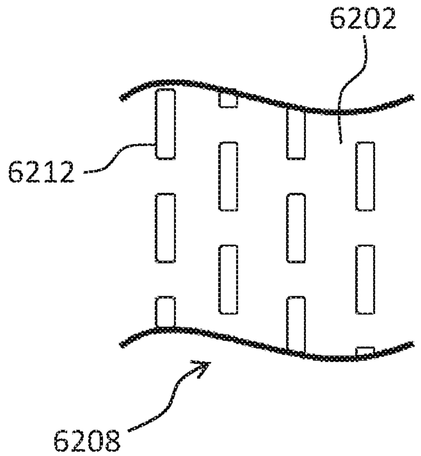

FIG. 8-1 is a cross-sectional view of a seal-forming structure 6200 according to an example of the present technology.

FIG. 8-2 is a view of a section of the seal-forming structure 6200 of FIG. 8-1 according to one example of the present technology.

FIG. 8-3 is a view of a section of the seal-forming structure 6200 of FIG. 8-1 according to another example of the present technology.

Figures 1, 9:
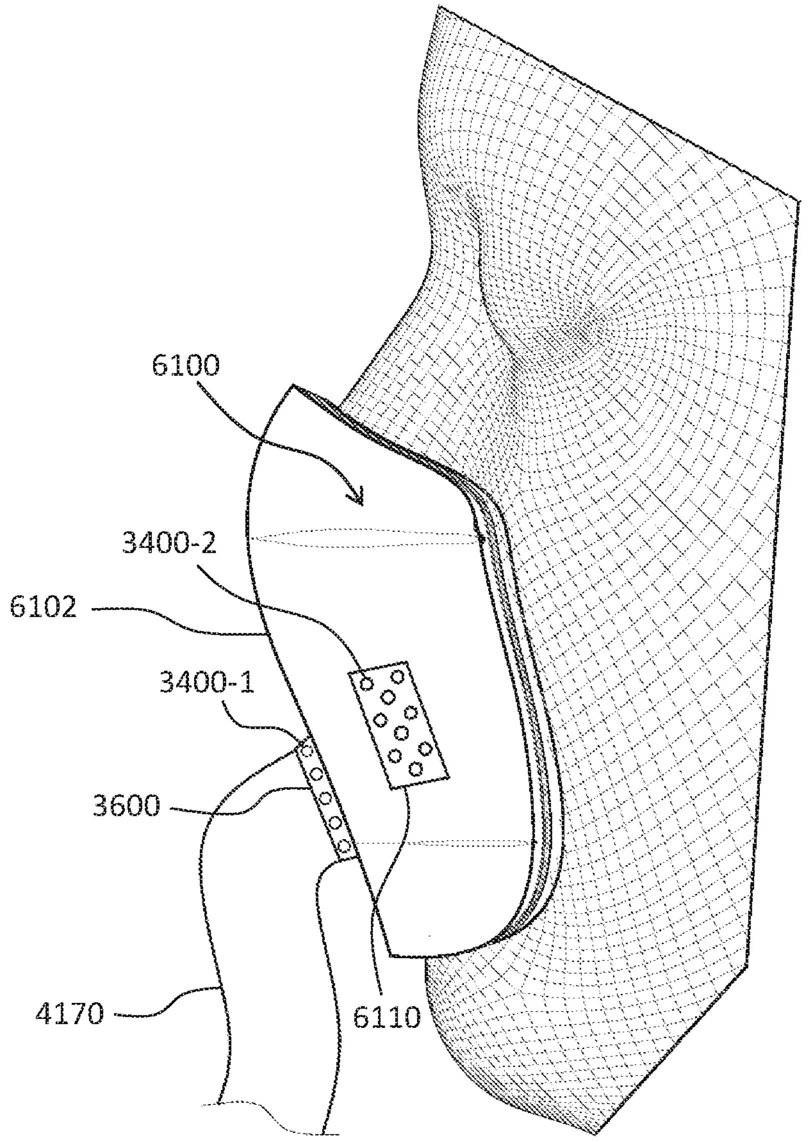
Figures 2, 9:
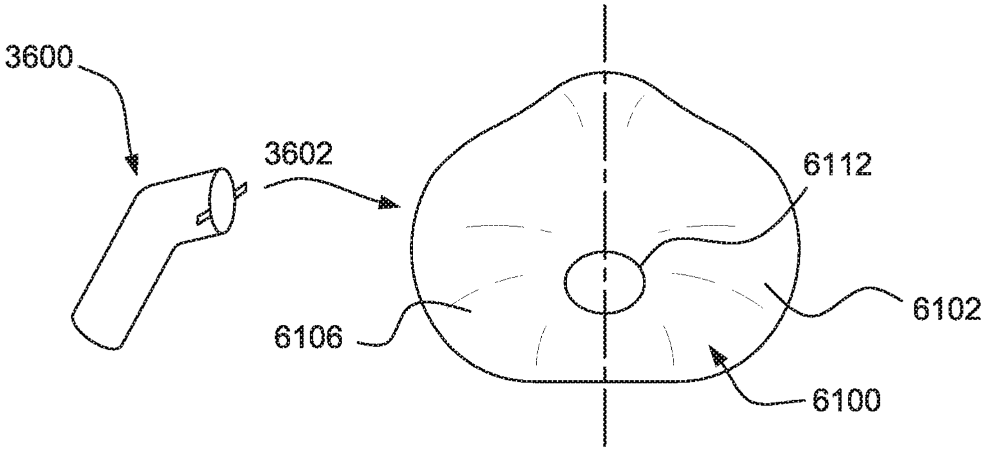
Figures 3, 9:
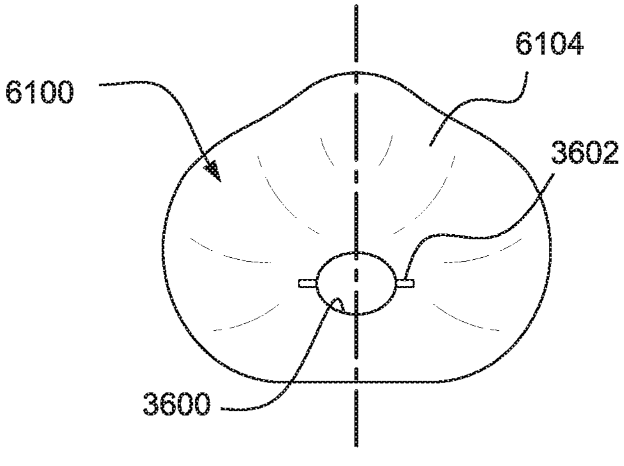

FIG. 9-1 is a side view of a patient interface 6000 according to another example of the present technology.

FIG. 9-2 is a perspective view of the patient interface 6000 of FIG. 9-1, illustrating a connection port being inserted into a frame.

FIG. 9-3 is a rear view of the patient interface 6000 of FIG. 9-1, illustrating projections retaining the connection port to the frame.

Figures 1, 10:
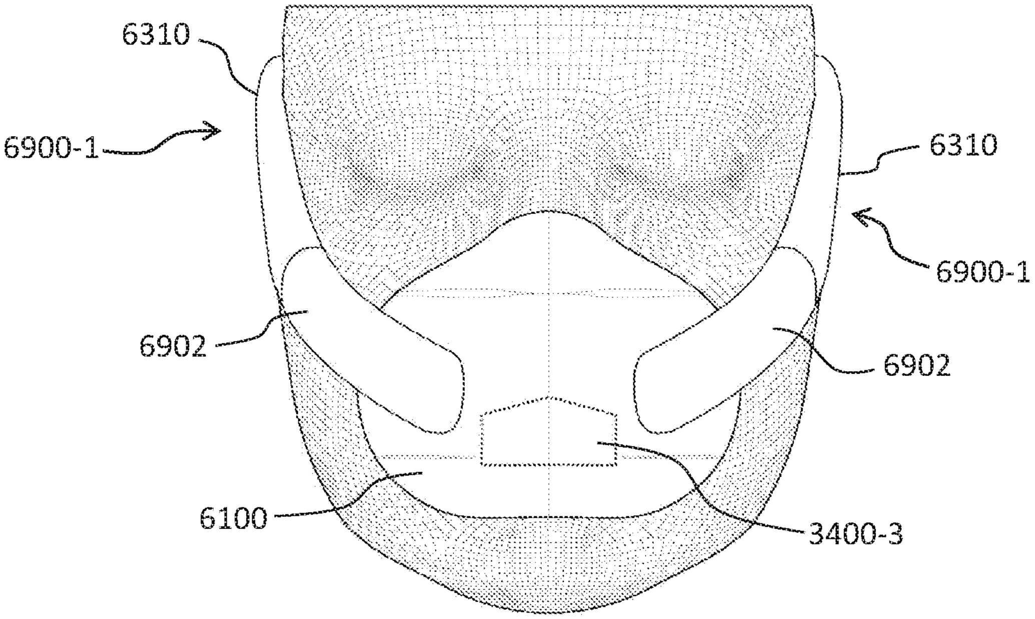
Figures 2, 10:
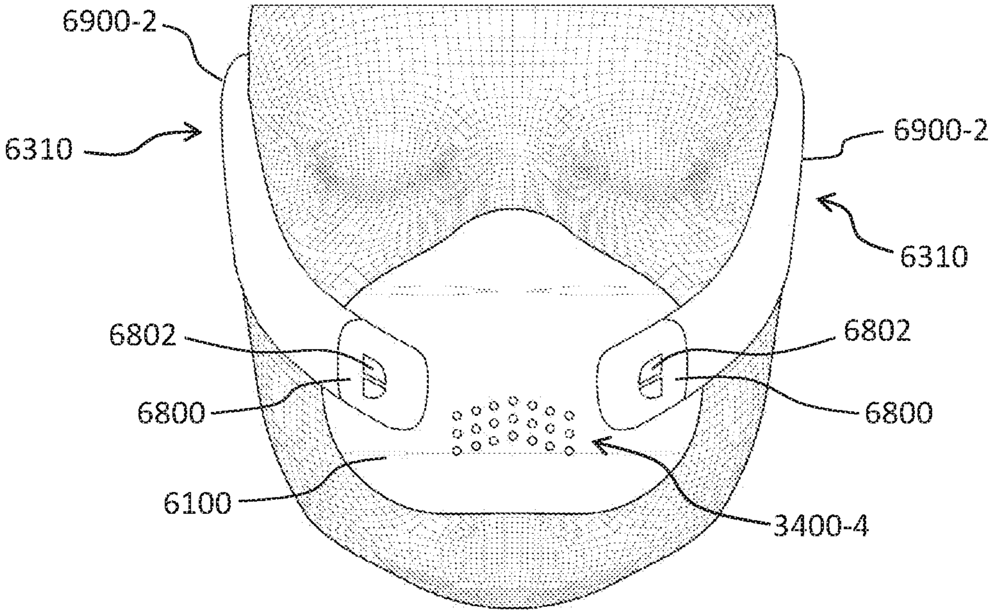

FIG. 10-1 is a front view of a patient interface 6000 according to a further example of the present technology.

FIG. 10-2 is a front view of a patient interface 6000 according to another example of the present technology.

Figure 11:
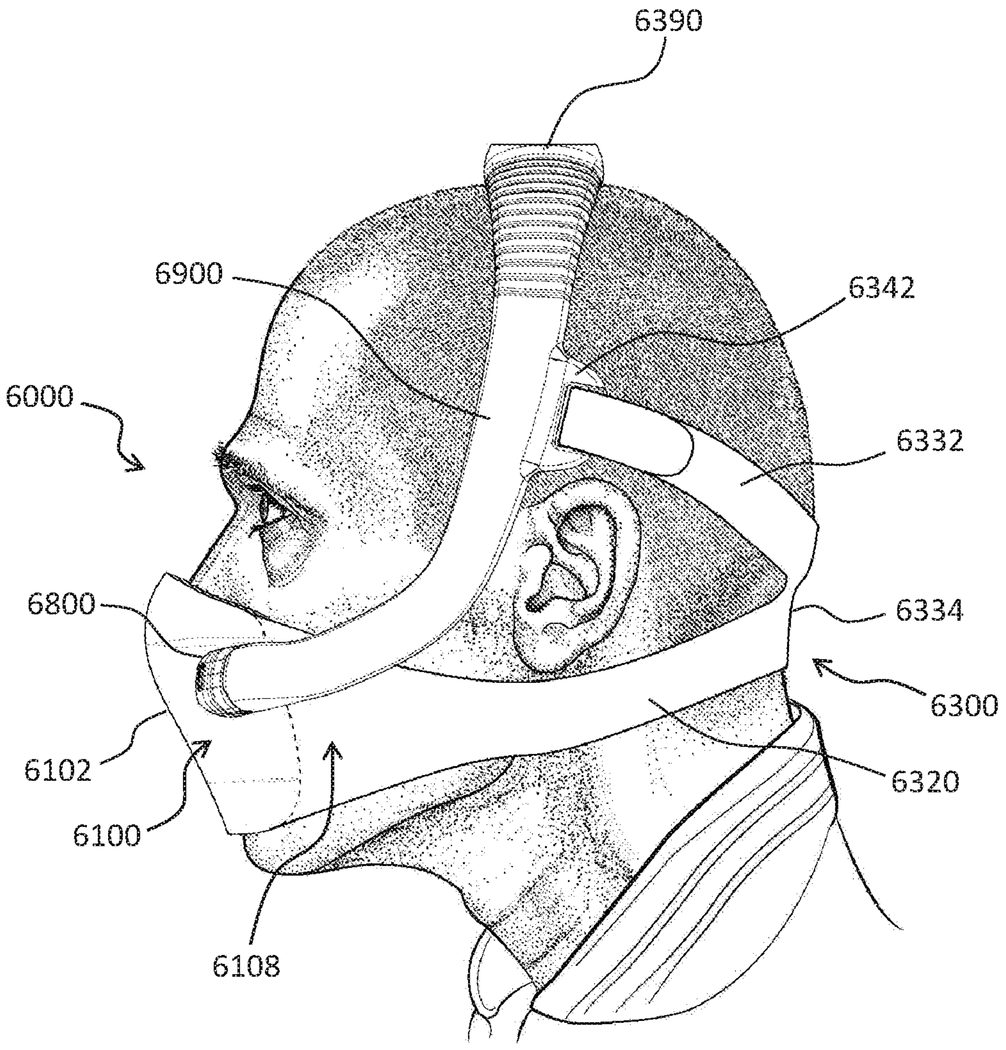

FIG. 11 is a side view of a patient interface 6000 according to an additional example of the present technology.

Figures 1, 12:
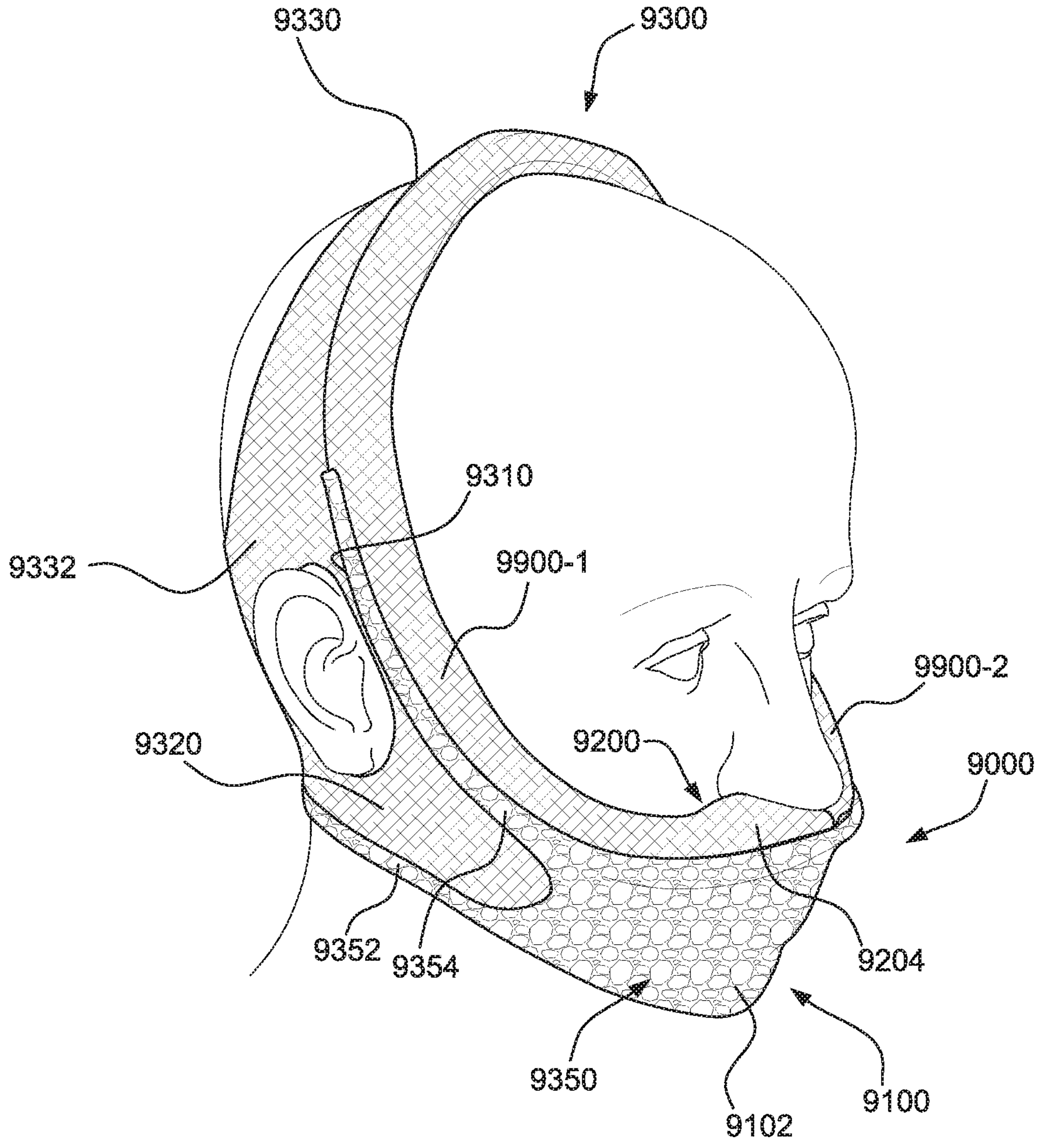
Figures 2, 12:
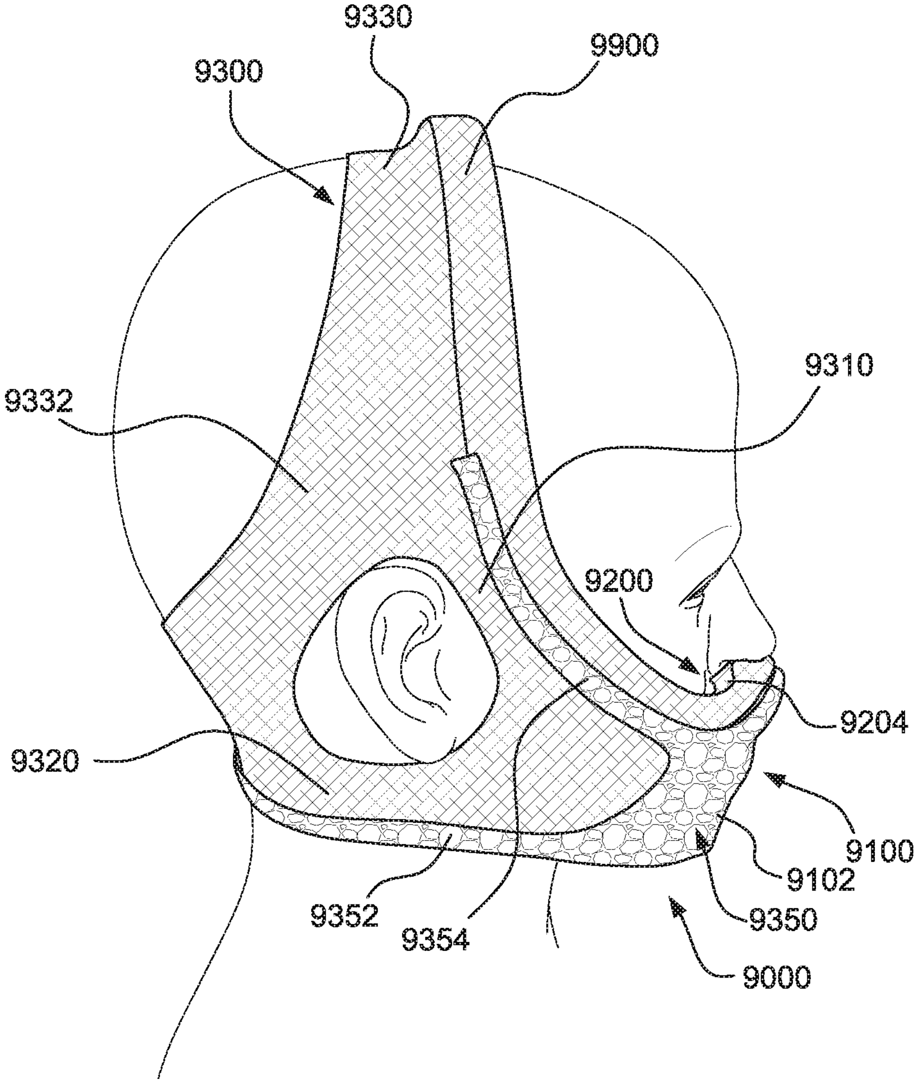
Figures 3, 12:
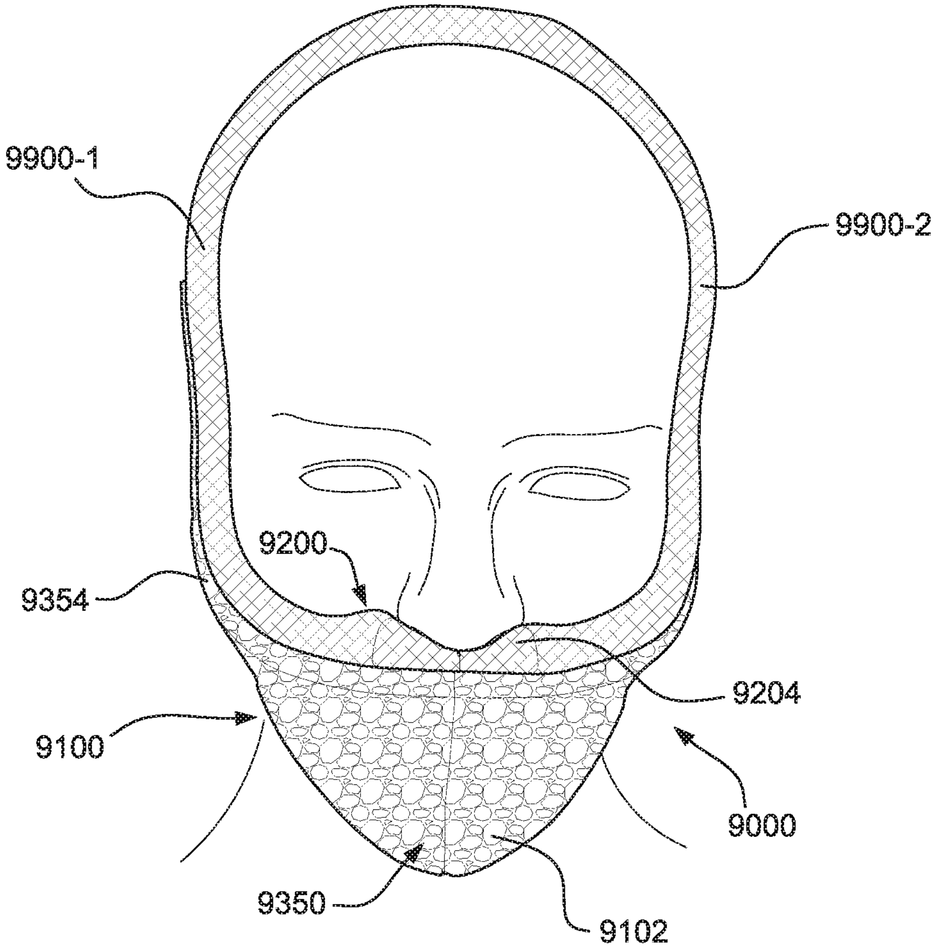
Figures 4, 12:
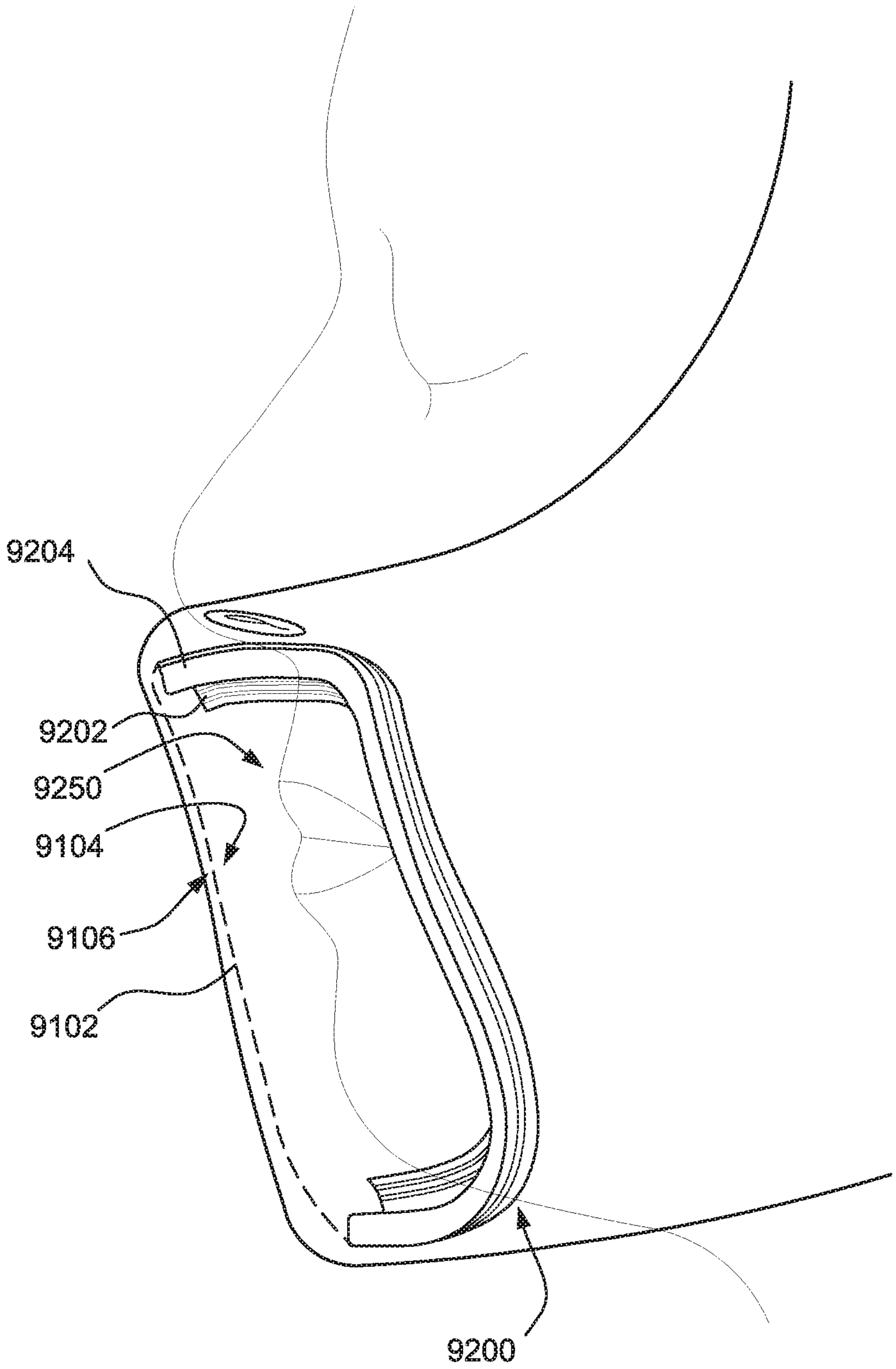
Figures 5, 12:
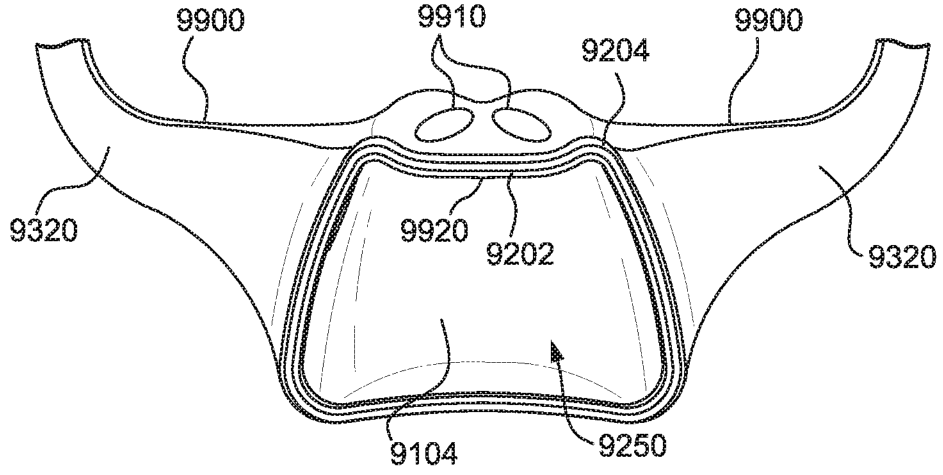

FIG. 12-1 is a perspective view of a patient interface 9000 according to an additional example of the present technology.

FIG. 12-2 is a side view of the patient interface of FIG. 12-1.

FIG. 12-3 is a front view of the patient interface of FIG. 12-2.

FIG. 12-4 is a side view of the seal-forming structure of the patient interface of FIG. 12-1.

FIG. 12-5 is a rear view of the patient interface of FIG. 12-1.

Figure 13:
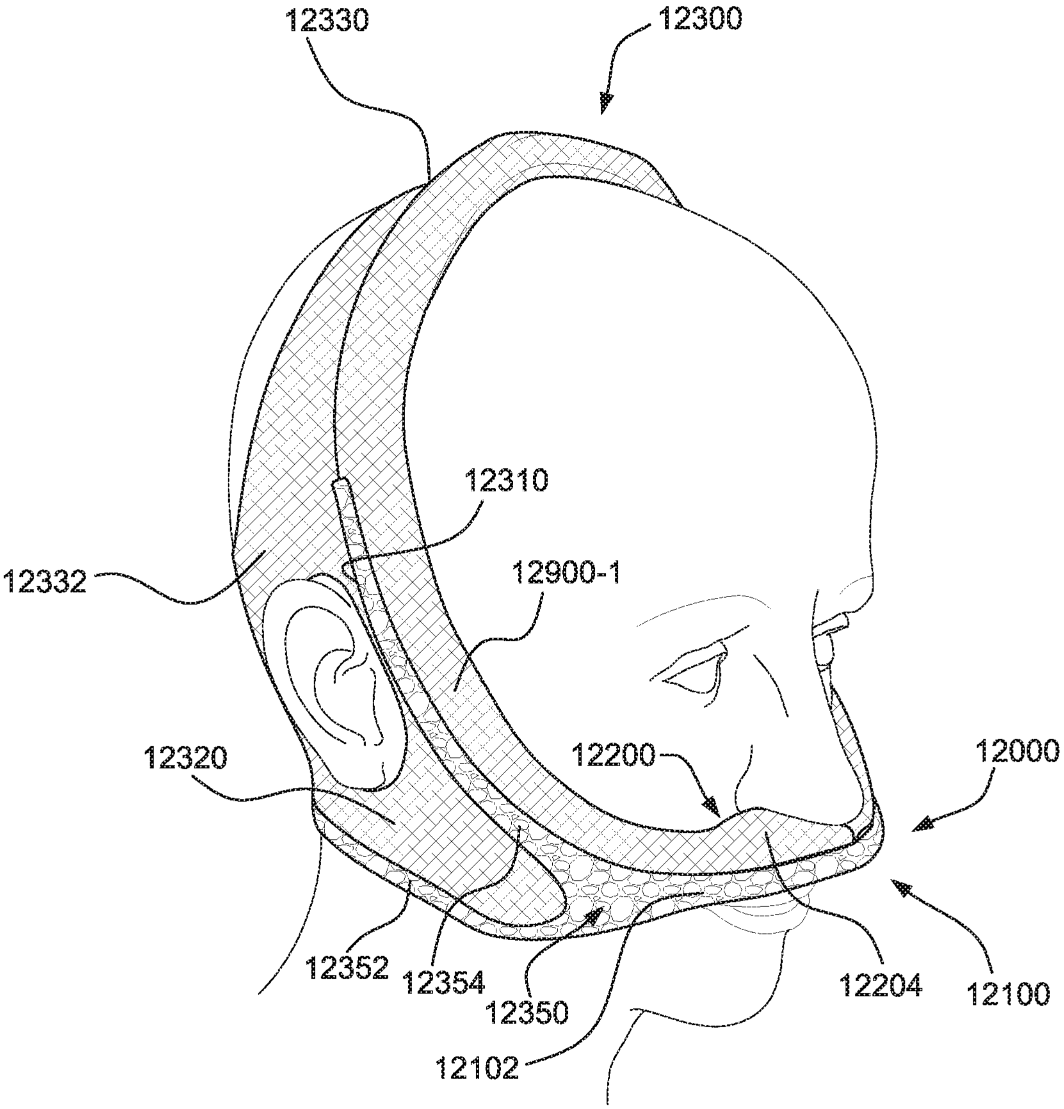

FIG. 13 is a perspective view of a patient interface 12000 according to an additional example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

A patient interface in accordance with one form of the present technology is constructed and arranged to be able to provide a supply of air at a positive pressure of at least 6 $cmH_2O$ with respect to ambient.

A patient interface in accordance with one form of the present technology is constructed and arranged to be able to provide a supply of air at a positive pressure of at least 10 $cmH_2O$ with respect to ambient.

A patient interface in accordance with one form of the present technology is constructed and arranged to be able to provide a supply of air at a positive pressure of at least 20 $cmH_2O$ with respect to ambient.

A patient interface in accordance with one form of the present technology is configured so that no part of the patient interface structure enters the mouth in use.

FIG. 7-1 shows a non-invasive patient interface 6000 according to examples of the present technology comprising a frame 6100 (which may also be referred to as a fascia), a seal-forming structure 6200, and a positioning and stabilising structure (e.g., headgear 6300).

FIG. 12-1 shows a non-invasive patient interface 9000 according to other examples of the present technology comprising a frame 9100 (which may also be referred to as a fascia), a seal-forming structure 9200, and a positioning and stabilising structure (e.g., headgear 9300).

FIG. 13 shows a non-invasive patient interface 12000 according to examples of the present technology comprising a frame 12100 (which may also be referred to as a fascia), a seal-forming structure 12200, and a positioning and stabilising structure (e.g., headgear 12300).

The patient interfaces 9000, 12000 are substantially similar to the patient interface 6000, and description related to the patient interface 6000 is generally applicable to the patient interfaces 9000, 12000 unless otherwise specified. Only some similarities and differences between the patient interfaces 6000, 9000, 12000 are described below. Similar features may have the same reference numbers, plus "3000" or "6000" respectively.

5.3.1 Frame

In one form of the present technology, a frame 6100 of the patient interface 6000 is constructed from a flexible material. It is envisaged that this flexibility may allow the frame to follow and adapt to the curvature of the patient's face. In examples the flexible material may have a relatively thin sheet-like structure. It is envisaged that this may assist with providing a relatively low profile on the patient's face, particularly in the anterior direction.

In certain examples, the flexible frame 6100 may be made from an airtight or impermeable textile material. The use of a textile material may help the patient interface to look and feel more like clothing than medical equipment and therefore may improve the patient's compliance with therapy.

In certain examples, a textile material may be used as a cover for the flexible frame 6100. The textile would also be flexible, and would not impede the flexibility of the frame 6100. The cover would provide a visual that the patient may associate with clothing, as opposed to medical equipment. The textile material in the cover may also contact the patient during use in order to provide the feel of clothing. For example, this may include a softer texture (e.g., as opposed to silicone), moisture wicking abilities, as well as other properties. An additional flexible material (e.g., silicone) may be provided under the textile in order to provide additional impermeability and/or structural support.

In certain examples, the flexible frame 6100 is constructed entirely from a textile material. The textile may be slightly rigidized so that the flexible frame 6100 is sturdy enough to maintain its shape, but not fully rigidized that it is unable to bend or flex. The textile may be rigidized using a coating, a laminate, a rigidized thread sewn into the textile, or any similar means. Constructing the flexible frame 6100 entirely out of the textile material may make the flexible frame lighter as compared to the flexible frame 6100 utilizing the textile cover. A lighter frame 6100 may be beneficial to a patient wearing the patient interface 6000 because the patient may experience less weight on their face.

In certain examples, the flexible frame 6100 may be made from a foam material.

In an example, one or both sides of the material of the flexible frame (i.e., internal and/or external surfaces of the frame) is coated, laminated, sealed, or otherwise provided with an impermeable surface (e.g., impermeable silicone layer or membrane imbedded in textile material) in order to provide an airtight or impermeable structure. Such arrangement provides an impermeable structure.

In certain examples, the flexible frame 6100 may be made from a flexible polymer. Examples of suitable flexible polymers may comprise: silicone, thermoplastic elastomers, or other biocompatible elastomers.

In certain examples, the patient interface 6000 may comprise one or more rigidising elements (i.e. rigidisers). In examples, the flexible frame 6100 may comprise rigidisers having greater stiffness than the flexible material from which the frame 6100 is made. Such rigidisers may be used to provide, for example, one or more of support, shape, form and/or strength to the frame 6100. By way of example, the frame 6100 may be shaped to provide space for the patient's nose, so that the frame 6100 is not in contact with the patient's nose. Such rigidisers may comprise, for example, one or more of: wire, a polymer, a textile, a thickened portion, or a fold. In examples, the rigidisers may be adjustable, for example to adjust the frame 6100 to suit different face shapes. Adjustable rigidizers may be semi-rigid so that they can maintain a selected shape, but are not limited to only a single shape. Adjustments to the rigidizers can be made once or repeatedly depending on the material.

In one form, a flexible frame 6100 constructed entirely from a textile material may require additional support in order to maintain a desired shape of the frame. In other words, the frame 6100 constructed from textile alone may flex or bend under the force of gravity so that the desired shape of the frame 6100 is not achieved. Rigidizers can be added to the flexible frame 6100 in order to provide three-dimensional shape to the textile. The rigidizers may be light weight so as not to add a substantial amount of additional weight onto the flexible frame 6100. In this way, the patient can achieve the same benefits of a light weight frame 6100, while also having the structural support of a more rigid material than textile.

The rigidizers may be semi-rigid. In other words, the rigidizers may be more rigid than the textile material, but not completely rigid. In this way, they are capable of providing structure to the frame 6100, but are flexible so that they are capable of being bent. A patient and/or medical professional may adjust or bend the rigidizers in order to provide tailored support for an individual patient. The rigidizers also may begin semi-rigid, and may become rigid after a period of time. For example, a medical professional may adjust the shape of the rigidizers so that the flexible frame 6100 is suited for an individual patient's face. Then the rigidizers may be treated (e.g., heat treated) so that they are set in their shape.

In certain forms of the present technology, the frame 6100, or a portion thereof, is constructed from a transparent, or at least translucent, material. For example, the frame 6100 may be made of a diaphanous textile, or a transparent polymer. The use of a transparent material can reduce the obtrusiveness of the patient interface, and help improve compliance with therapy. The use of a transparent material can aid a clinician to observe how the patient interface 6000 is located and functioning. The transparent material may also assist in patient compliance because the patient wearing the patient interface 6000 will be able to observe at least a portion of their oro-nasal region in a mirror, which may provide the feel or wearing clothing as opposed to a medical device. A transparent or translucent substance may be added to (e.g., coated with, layered, etc.) the transparent material in order to provide an airtight surface, without compromising the transparency of the textile, or other material. A non-transparent substance may also be added to only a portion of the transparent material, so that a portion of the transparent material remains transparent. Thus, the clinician and/or the patient may still be able to observe how the patient interface 6000 is located.

In certain forms of the present technology, the frame 6100 at least partially forms a plenum chamber of the patient interface 6000. The plenum chamber may be pressurisable to a therapeutic pressure of at least 6 $cmH_2O$ above ambient air pressure. As shown in FIG. 7-4, a seal-forming structure 6200 is constructed and arranged to form a seal with a region of the patient's face surrounding an entrance to the patient's airways. The seal-forming structure 6200 has a hole therein such that the flow of air at said therapeutic pressure is delivered to at least an entrance to the patient's nares. The flow of air may also be delivered to the patient's mouth (i.e., when the hole of the seal-forming structure 6200 also surrounds the patient's mouth). A plenum chamber portion 6102 of the frame 6100 has a posterior facing surface 6104 and an anterior facing surface 6106. The plenum chamber portion 6102 extends over the hole of the seal-forming structure 6200, with the plenum chamber portion 6102 and seal-forming structure 6200 cooperating to form the plenum chamber. While some contact between the face of the patient and plenum chamber portion 6102 of the frame 6100 may occur, the seal-forming structure 6200 is intended to space the frame 6100 away from the patient's face so that contact is limited. The frame 6100 is also shaped so that is assists in limiting contact with the patient's face. The seal is provided by the seal-forming structure 6200.

In certain forms of the present technology, the flexible frame 6100 may extend beyond the seal-forming structure 6200 in a direction away from the hole of the seal-forming structure 6200 (i.e. away from the plenum chamber). More particularly, lateral portions 6108 of the frame 6100 may extend in a posterior direction in use, for connection to headgear 6300. In one form, the flexible frame 6100 and the headgear 6300 may be formed from a single piece of material (e.g., a sheet of textile), so that the frame 6100 and headgear 6300 are connected without a seam, or other connector. The lateral portion 6108 may represent a transition in order to delineate where the frame 6100 ends and the headgear begins 6300. This may be shown by a change in width and/or thickness (e.g., tapering) of the lateral portion 6108 between the frame 6100 and the headgear 6300.

In certain forms of the present technology, the frame 6100—and more particularly the plenum chamber—does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the frame comprises a plenum chamber 3200 in the form of a shell and has a shell inside surface and shell outside surface, wherein the shell inside surface is arranged to be at said therapeutic pressure in use, and said shell outside surface is arranged to be at ambient pressure in use. Patient interfaces according to examples of the present technology are contemplated in which the frame is substantially rigid (e.g. as shown in FIG. 3A), and provided with the seal-forming structure 6200 (e.g. the seal-forming structure 6200 as shown in FIGS. 7-3 to 8-1).

In certain forms of the present technology, the shell is structured to be rigid when subject to an internal pressure of less than about 30 $cmH_2O$ above ambient pressure.

In certain forms of the present technology, the shell is constructed from a hard plastic material, e.g. a polycarbonate. One form of commercially available polycarbonate is Apec 1745 (included in the range of products sold under this trademark), manufactured by Covestro AG.

In certain forms of the present technology, the shell is constructed from a transparent material, e.g. a transparent polycarbonate.

In certain forms of the present technology, the shell inside surface is constructed to include a concave dome-shaped region.

5.3.2 Seal-Forming Structure

In one form of the present technology, a seal-forming structure 6200 provides a target seal-forming region, and may additionally provide a cushioning function. The target seal-forming region is a region on the seal-forming structure where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face. In other words, the actual seal-forming region may be more or less than the target seal-forming region. The patient ideally wants to minimize these factors from creating an actual seal-forming region that is different from the target seal-forming region. Having an actual seal-forming region that is less than the target seal-forming region may reduce effectiveness of the treatment. Having an actual seal-forming region that is greater than the target seal-forming region may cause irritation in the patient because therapeutic pressure is applied to unintended areas of the patient's face.

In one form the target seal-forming region is located on an outside surface of the seal-forming structure 6200.

In certain forms of the present technology, the seal-forming structure 6200 is constructed from biocompatible material. The biocompatible material may be any material that does not negatively react with the patient's skin. For example, the seal-forming structure 6200 may be made from a textile that does not irritate the patient's skin.

In one form, the seal-forming structure 6200 does not extend internally of the patient's airways. In other words, the seal-forming structure 6200 does not extend within the patient's nostrils and/or the patient's mouth.

In one form, the seal-forming structure 6200 does not extend below a mental protuberance region in use. In other words, the seal-forming structure 6200 remains entirely on the patient's face, and does not extend below the patient's chin, to the patient's neck.

In certain forms of the present technology, a system is provided comprising more than one a seal-forming structure 6200, each being configured to correspond to a different size and/or shape range. For example the system may comprise one form of a seal-forming structure 6200 suitable for a large sized head, but not a small sized head and another suitable for a small sized head, but not a large sized head. An RPT device (described later), may assist the patient in identifying which seal-forming structure 6200 is appropriate from them. For example, the RPT device may give the patient an error if it senses that a target seal-forming region for a specific patient in not being achieved with a certain sized seal-forming structure 6200. This would alert the patient that they should change to a different sized seal-forming structure 6200.

In one form, the seal-forming structure 6200 and the frame 6100 may be separate pieces that are coupled together by the patient and/or the clinician. The patient interface 6000 can be constructed modularly in order to tailor the fit to the individual patient. In other words, the frame 6100 may come in a plurality of sizes (e.g., small, medium, large) and the seal-forming structure 6200 may come in a variety of sizes (e.g., small, medium, large). The patient and/or clinician may select one size frame 6100 and one size seal-forming structure 6200, although not necessarily the same sizes. The selected seal-forming structure 6200 may then be connected to the selected frame 6100 using an adhesive, or similar connector, in order to provide a substantially airtight interface between the frame 6100 and the seal-forming structure 6200. In other words, the frame 6100 and the seal-forming structure 6200 are connected in order to prevent or limit leaks through the connection interface.

In one form, the seal-forming structure 6200 and the frame 6100 may be permanently coupled together. Together, the frame 6100 and the seal-forming structure 6200 come in a plurality of sizes (e.g., small, medium, large). In other words, the frame 6100 and the seal-forming structure 6200 are the same size. Although, in some examples, the patient interface 6000 could be custom made so that the frame 6100 was formed at a different size than the seal-forming structure 6200 in order to provide a more exact fit for a given patient. In one example, the seal-forming structure 6200 and the frame 6100 are formed together when the patient interface 6000 is manufactured so that the seal-forming structure 6200 is not separable from the frame 6100, and so that the patient and/or the clinician do not have to assemble the patient interface 6000. The patient would change the entire patient interface 6000 in the event that the selected size was inappropriate.

In one form, the seal-forming structure 6200 and the frame 6100 may be permanently coupled together. The frame 6100 and the seal-forming structure 6200 may come in a single size (e.g., one size fits all or one-size fits most), or may come in combination sizes that fit a wider range of patients (e.g., small-medium, medium-large, etc.). For example, a single size and/or style of patient interface 6000 may effectively seal on patient's faces with multiple sizes and shapes. In other words, a one size fits all and/or one size fits most patient interface 6000 may be used in place of small/medium/large sized patient interfaces 6000, and still seal against the patient's face with substantially the same effectiveness. This may be because a textile is more pliable than other flexible materials used to construct seal-forming structures (e.g., silicone), and therefore permits a single sized seal-forming structure 6200 to conform to a wide variety of patients' faces. Alternatively and/or in addition, combination sizes (e.g., small-medium, medium-large, etc.) may provide a similar benefit of sealing with a wider variety of patients, while being more tailored to patients with difference sized faces. In either example, the smaller number of sizes for a patient interface 6000 may assist in simplifying manufacturing, while also better assuring that patients have the proper patient interface 6000 (e.g., because there are fewer sizes that they may incorrectly select).

In examples in which the frame comprises the plenum chamber 3200 (i.e. a plenum chamber comprising a shell), the plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 6200. The seal-forming structure 6200 may extend in use about the entire perimeter of the plenum chamber 3200.

5.3.2.1 Sealing Mechanisms

In one form of the present technology, the seal-forming structure 6200 comprises a textile seal member 6202 that is positioned against the patient's face in order to sealingly engage with the patient's skin. When the frame 6100 is connected to the seal-forming structure 6200 (e.g., either removably or permanently), the textile seal member 6202 allows the patient interface 6000 to maintain a positive pressure of at least 6 $cmH_2O$.

In one of the illustrated examples, the textile seal member 6202 forms a perimeter that encompasses both the patient's mouth and the patient's nose, although in other examples, only the nose may be encompassed or sealed partially around (see e.g., FIG. 13). When positioned on the patient's face, an uppermost portion of the textile seal member 6202 is positioned against a ridge of the patient's nose. In other words, the textile seal member 6202 contacts the patient's nose adjacent to the septum cartilage, and between the patient's sellion and pronasale. In the illustrated example, the textile seal member 6202 is disposed proximate to the pronasale, and is adjacent to the lateral cartilage and/or the greater alar cartilage in the patient's nose. The uppermost portion of the textile seal member 6202 may also be substantially aligned with the Frankfort Horizontal of the patient's face. Positioning the textile seal member 6202 proximate to the pronasale reduces the total volume that is required for sealing. This is because the upper end of the textile seal member 6202 is positioned closer to the patient's nares, as opposed to proximate to the sellion.

The lowermost portion of the of the textile seal member 6202 is positioned against the supramenton. In other words, the textile seal member 6202 is positioned below the patient's mouth, so that the patient's lip inferior is included within the pressurized volume. The patient's lip inferior may move while the patient is breathing, and this movement may disrupt the textile seal member 6202 (e.g., the movement of the lip inferior may create leaks) if the textile seal member 6202 were positioned on the lip inferior. Positioning the lowermost point of the textile seal member 6202 below the lip inferior limits this occurrence by permitting the lip inferior to move with some freedom, and not affect the quality of the seal. Positioning the lowermost point of the textile seal member 6202 against the supramenton does not significantly increase the pressurized volume that the textile seal member 6202 is required to create. In other examples (not shown), the lowermost point of the textile seal member 6202 may be disposed against the lip inferior.

The textile seal member 6202 extends outside of the patient's nose and mouth, on either side of the patient's face, in order to connect between the uppermost and lowermost points of the textile seal member. The textile seal member 6202 may not extend significantly beyond the patient's mouth width, in order to maintain a substantially small volume of pressurized air (i.e., avoiding including a region of the patient's cheek significantly beyond the patient's nose or mouth). For example, the textile seal member 6202 is disposed proximate the patient's nasolabial sulcus on either side of the patient's face (i.e., right and left sides), because the nasolabial sulcus represents a region not significantly wider than the mouth width. In the illustrated example, the textile seal member 6202 may be positioned outside of each nasolabial sulcus, so that each nasolabial sulcus is within the pressurized volume. Similar to the lip inferior, the nasolabial sulcus may represent a location of movement on the patient's face. In other words, the nasolabial sulcus is a crease caused by movement of the patient's face. This movement may affect the quality of the seal created by the textile seal member 6202. Since the nasolabial sulcus extends proximate to the patient's nose, the textile seal member 6202 is positioned outside of the nasolabial sulcus in order to avoid the movement that the nasolabial sulcus creates. In other examples (not shown), the textile seal member 6202 may contact the nasolabial sulcus.

In other forms (see e.g., FIG. 12-4), the textile seal member 9202 seals around the patient's nares and mouth. For example, the textile seal member 9202 forms a perimeter that encompasses the patient's mouth and at least a portion of the patient's nose (e.g., only a portion of the patient's nose). When positioned on the patient's face, an uppermost portion of the textile seal member 9202 may contact the patient's nose against the columella, and between the patient's subnasale and pronasale. In the illustrated example, an uppermost portion of the patient interface 9000 is disposed inferior to the patient's pronasale, so that the pronasale is exposed while the patient wears the patient interface 9000. The uppermost portion of the textile seal member 9202 may also be substantially aligned with the Frankfort Horizontal of the patient's face. Positioning the textile seal member 9202 inferior to the pronasale further reduces the total volume that is required for sealing (e.g., as compared to the example described above). This is because the upper end of the textile seal member 9202 is positioned even closer to the patient's nares, and does not seal against the ridge of the patient's nose.

The lowermost portion of the of the textile seal member 9202 may be positioned around the mental protuberance. In other words, the textile seal member 9202 is positioned below the patient's chin, so that the patient's lip inferior and supramenton are included within the pressurized volume. The patient's lip inferior may move while the patient is breathing, and this movement may disrupt the textile seal member 9202 (e.g., the movement of the lip inferior may create leaks) if the textile seal member 9202 were positioned on the lip inferior. Positioning the lowermost point of the textile seal member 9202 below the lip inferior limits this occurrence by permitting the lip inferior to move with some freedom, and not affect the quality of the seal. Positioning the lowermost point of the textile seal member 9202 around the mental protuberance does not significantly increase the pressurized volume that the textile seal member 9202 is required to create. However, it may provide an anchor point for the textile seal member 9202 to seal against, and may help to create the seal across a variety of sized patients. In other words, the patients with all sized faces may position the textile seal member 9202 against their chin in order to create substantially the same sealing force across all sized faces (e.g., the textile seal member 9202 may stretch around the mental protuberance, and the tension may assist in properly positioning the textile seal member 9202). In other examples (not shown), the lowermost point of the textile seal member 9202 may be disposed against the lip inferior or the supramenton (e.g., when the patient interface 9000 is a combination size and is slightly more tailored to an individual patient).

The textile seal member 9202 extends outside of the patient's nose and mouth, on either side of the patient's face, in order to connect between the uppermost and lowermost points of the textile seal member 9202. The textile seal member 9202 may not extend significantly beyond the patient's mouth width, in order to maintain a substantially small volume of pressurized air (i.e., avoiding including a region of the patient's cheek significantly beyond the patient's nose or mouth). For example, the textile seal member 9202 is disposed proximate the patient's nasolabial sulcus on either side of the patient's face (i.e., right and left sides), because the nasolabial sulcus represents a region not significantly wider than the mouth width. In the illustrated example, the textile seal member 9202 may be positioned outside of each nasolabial sulcus, so that each nasolabial sulcus is within the pressurized volume. Similar to the lip inferior, the nasolabial sulcus may represent a location of movement on the patient's face. In other words, the nasolabial sulcus is a crease caused by movement of the patient's face. This movement may affect the quality of the seal created by the textile seal member 9202. Since the nasolabial sulcus extends proximate to the patient's nose, the textile seal member 9202 is positioned outside of the nasolabial sulcus in order to avoid the movement that the nasolabial sulcus creates. In other examples (not shown), the textile seal member 9202 may contact the nasolabial sulcus.

The perimeter formed by the textile seal member 6202 may be curved along the path described above. In other words, the textile seal member 6202 may follow a rounded path from the ridge of the nose toward the supramenton (or toward the patient's mental protrusion), as opposed to a purely linear path. Specifically, corners of the textile seal member 6202 may be rounded. This assists with limiting areas of increased pressure concentration, which could lead to failure of the textile seal member 6202 (e.g., the seal ruptures). Providing a rounded perimeter may therefore increase the overall lifespan of the textile seal member 6202.

The textile of the textile seal member 6202 may be the same textile used in the frame 6100, or may be a different textile than what was used to construct the frame 6100. Being textile, this seal member 6202 may have tactile properties providing a soft and comfortable feel against the patient's face. Further, such material may assist with providing a look and feel more like bedclothes than respiratory treatment equipment (e.g., that are constructed from plastic, silicone, etc.), increasing a patient's willingness to wear the patient interface and help improve compliance with therapy An example of textile material for the textile seal member 6202 may comprise a fabric comprising polyether-polyurea copolymer fibres, i.e. spandex or elastane fabric.

In the examples shown in FIGS. 7-3 to 8-3, the textile seal member 6202 has a relatively thin sheet-like structure. A textile material may provide a relatively high degree of elasticity, assisting the textile seal member 6202 with conforming to the shape of the patient's face to form a seal. The textile seal member 6202 may be slightly smaller than a sealing region on the patient's face, so that the textile seal member 6202 expands (e.g., stretches) when positioned in a therapeutically effective position against the patient's face. The high degree of elasticity in the textile seal member 6202 allows the textile seal member 6202 to expand while contacting the patient's face, and relaxing and returning to a rest position when no longer in contact with the patient's face. The width of the seal member 6202 being much greater than its thickness provides a large surface area in contact with the patient's face, which may assist with distributing forces exerted through the seal member 6202 to reduce the likelihood of discomfort.

In certain forms of the present technology, the textile seal member 6202 is air impermeable in order to prevent leaks therethrough. In examples, the textile seal member 6202 may be provided with an air impermeable layer, such as polyurethane (e.g. a thermoplastic polyurethane), or silicone. Such a layer may be provided, for example, by way of laminating a film, or spraying a coating, onto the textile seal member 6202. In other examples, the textile itself used in constructing the textile seal member 6202 may be impermeable, so that an additional impermeable layer does not need to be applied.

In alternative forms of the present technology, the textile seal member 6202 is air permeable in order to allow a controlled leak for the purpose of venting. Portions of the textile seal member 6202 may be impermeable (e.g., coated with an impermeable layer), and other portions may not. This allows portions of the textile seal member 6202 to have a controlled leak, while other portions remain impermeable. The locations of the air permeable sections may be included in positions that do not affect the quality of the seal between the textile seal member 6202 and the patient's skin.

5.3.2.1.1 Compliant Portion of Seal-Forming Structure

In certain forms of the present technology, the seal-forming structure 6200 comprises a compliant portion 6204 provided to the posterior facing surface 6104 of the frame 6100, with the textile seal member 6202 provided to the compliant portion 6204. A compliant structure or component is one in which will deform in response to an applied load in order to take on the shape of the surface against which it is provided, more particularly the shape of the patient's face. This may assist with patient comfort though accommodation of points of the patient's face that might otherwise receive excessive force as the patient interface 6000 is held in place. It may also assist with facilitating achieving a seal through allowing the seal member 6202 freedom to conform to the curvature of the patient's face, particularly around their nose and mouth. The compliant portion 6204 may be coupled to the frame 6100 (e.g., using an adhesive), or the compliant portion 6204 may be permanently formed with the frame 6100 (e.g., via a manufacturing process). With either method, the interface between the compliant portion 6204 and the frame 6100 is substantially impermeable in order to limit pressurized air leaking through the interface. The textile seal member 6202 may be permanently formed with the compliant portion 6204. This helps to create an impermeable interface between the compliant portion 6204 and the textile seal member 6202, in order to substantially limit unintended leaks of pressurized air through the seal-forming structure 6200.

In one example, the compliant portion 6204 may extend generally transverse or orthogonally with respect to the seal member 6202. At least a portion of the frame 6100 extends transversely or orthogonally with respect to the compliant portion 6204 when the two are coupled together. As shown in FIG. 8-1, the plenum chamber 6102 extends transversely or orthogonally with respect to the thickness direction, so that a portion of the plenum chamber 6102 not directly contacting the compliant portion 6204 is generally parallel with respect to the seal member 6202. The plenum chamber 6102 may also extend tangential to the compliant portion 6204. The tangent angle may be small in order to approximate a parallel arrangement with respect to the seal member 6202 (see e.g., FIG. 7-5). These arrangements may assist in maintaining a low profile of the patient interface 6000 because a curvature in a center of the plenum chamber 6102 may curve gradually toward the compliant portion 6204 so that the distance between the patient's face and the plenum camber 6102 does not substantially exceed the thickness. In other words, the compliant portion 6204 may be concave relative to the patient's face, but the curvature of the compliant portion 6204 may approximate the contour of the patient's face so that the distance between the posterior facing surface 6104 and the closest point on the patient's skin in the posterior direction remains substantially constant along the length of the complaint portion 6204. For example, the complaint portion includes a curvature that approximates the curvature of the patient's nose, so that the distance between the posterior facing surface 6104 and the patient's pronasale is substantially the same as the distance between the posterior facing surface 6104 and the supramenton.

In one example (see e.g., FIG. 12-4), the compliant portion 9204 may be substantially straight or have a relatively small curvature (e.g., as compared to the example in FIG. 7-5). The compliant portion 9204 may be able to be positioned closer to the patient's face without a curvature because it does not need to extend around the patient's pronasale. Additionally, the compliant portion 9204 extends around the patient's chin, and therefore must come into close contact with the patient's skin (e.g., to include a low profile). Including a curvature may not be needed since it may create a larger sealing volume. The complaint portion 9204 may be spaced sufficiently away from the patient's mouth (as described with respect to the complaint portion 6204) so the patient may be able to breathe through their mouth with minimal impedance.

The compliant portion 6204 can also provide decoupling of the seal member 6202 from the frame 6100, which may facilitate a stable seal. Allowing the frame 6100 a degree of movement independent of the seal member 6202 means that forces received by the frame 6100 (such as from tube drag, or from a pillow during side sleeping) may not be completely passed on to the seal member 6202, avoiding disruption of the seal provided by the seal member 6202 in use, so that a seal necessary in order to maintain the therapeutic pressure within the plenum chamber is not disrupted while the patient is sleeping. In other words, the flexible nature of the plenum chamber portion 6102 may adsorb at least a portion of a tensile force applied by an air circuit 4170 so that seal member 6202 do not substantially shift on the patient's face. This may be particularly helpful when a connection port 3600 is used to connect the air circuit 4170 to the plenum chamber portion 6102 (see e.g., FIGS. 9-2 and 9-3). Accordingly, patient movement relative to the RPT device 4000 (e.g., rolling over while asleep), may not substantially disrupt the seal member 6202 because of the decoupling between the seal member 6202 from the frame 6100.

The compliant portion 6204 also acts as a spacer between the seal member 6202 and the frame 6100. This spacing may be required to allow space for the patient's nose and lips. In certain forms of the present technology the frame 6100 may be formed or otherwise shaped to allow space for the patient's facial features (for example, being formed to approximate the shape of a patient's face). However, it is envisaged that configuration of the compliant portion 6204 may achieve the requisite spacing while maintaining a low profile. In other words, the compliant portion 6204 shapes the frame 6100 apart from the patient's face at the least possible distance, so that the frame 6100 barely avoids contacting the patient's skin. The positioning of the frame 6100 with respect to the patient's face also creates a small volume within the plenum chamber. Only space that is needed (e.g., to support a volume of the pressurized air) is taken by the plenum chamber, thereby eliminating unnecessary space, and creating the low profile.

The low profile of the patient interface 6000 may also reduce forces received by the frame 6100 (such as from tube drag, or from a pillow during side sleeping) from being completely passed on to the seal member 6202. The low profile shape of the patient interface 6000 may improve dynamic stability (e.g., as compared to a patient interface 6000 that is further spaced from the patient's face). The dynamic stability may specifically be improved by reducing the bulk on the patient's face (e.g., less weight, closer to the patient's face, etc.) in order to reduce the likelihood of the patient interface 6000 being "levered off" of the patient's face during movement (e.g., rolling while sleeping). In other words, the low profile creates a fulcrum that is closer to the patient's face, and so that it is therefore more difficult to cause the textile seal member 6202 to disengage from the patient's face as a result of an applied tensile force (e.g., by the air circuit 4170).

The compliant portion 6204 is not constructed from a textile. In certain forms of the present technology, the compliant portion 6204 may be made of a foam material. Examples of suitable foam material may comprise: a memory foam (for example, ResMed's UltraSoft™ memory foam) that returns to a relaxed position when an applied force is removed, or a silicone foam. In examples, the foam material may be as described in International Patent Application Publication WO 2014/117227, International Patent Application Publication International WO 2016/054692, or Patent Application Publication WO 2017/049359, the entire contents of which are incorporated herein by reference. The patient interface 6000 thus alternates between a textile, a foam, and a textile.

In alternative forms of the present technology, the compliant portion 6204 may have another type of cellular structure providing compliant properties, for example a honeycomb structure made of silicone.

In alternate forms of the present technology, the compliant portion 6204 may have another type of structure providing compliant properties, for example a silicone spring having a C-shaped or S-shaped cross-section.

In certain forms of the present technology, the seal-forming structure 6200 comprises one or more rigidisers. Such rigidisers may be used to provide, for example, one or more of support, shape, form and/or strength to the seal-forming structure 6200 (and by extension the frame 6100). In the example of FIG. 8-1, a rigidiser 6205 is provided in the compliant portion 6204, which may be formed (e.g., molded, sewn, etc.) around the rigidiser 6205. In examples, the rigidiser 6205 may be formed from a semi-rigid material so that it is adjustable, for example to assist with adjustment to suit different face shapes. In some examples, the rigidisers 6205 are repeatedly adjustable (e.g., can be adjusted as needed). This allows the patient and/or clinician to make various adjustments though the life of the patient interface 6000. In other examples, the rigidisers 6205 may be adjustable once before they are set in the selected position. In other words, the rigidisers 6205 may begin as a semi-rigid element, but may become rigid after a treatment (e.g., heat) is applied. The rigidiser 6205 may be tailored to an individual patient and then fixed in the position suited for the individual patient (e.g., in order to provide a good seal on the patient's face). In some examples, the rigidiser 6205 may be exposed (see e.g., FIG. 7-1 along the superior and inferior sides) to the ambient while the frame 6100 is coupled to the seal-forming structure 6100.

The rigidisers 6205 may reduce deformation of the seal-forming structure 6200 when an external force (e.g., a tensile force) is applied to the frame 6100 (e.g., via the positioning and stabilizing structure 6300). Reducing the deformation may assist in maintaining the seal-forming structure 6200 in a therapeutically effective position.

In certain forms of the present technology, the textile seal member 6202 comprises an overlaying portion covering at least a portion of the compliant portion 6204, and an overhanging portion extending from the compliant portion 6204, with an air gap between the overhanging portion and the frame 6100. The overhanging portion of the textile seal member 6202 may be referred to herein as a flange 6206. In examples, the overhang of the textile seal member 6202 is such that the flange 6206 extends in a radially inward direction in a cantilever fashion. This arrangement may allow the seal-forming structure 6200 to utilize a pressure assisted sealing mechanism. In use, the flange 6206 can readily respond to a system positive pressure in the interior of the plenum chamber acting on its underside to urge it into tight sealing engagement with the face. A pressure assisted seal may be less likely to leak and may be more stable than a non-pressure assisted seal. The pressure assisted mechanism may act in conjunction with one or more other factors, for example elastic tension in the headgear 6300, tackiness of the seal member 6202 in contact with the patient's face, and the elasticity of the seal member 6202.

In certain forms of the present technology, the width of the textile seal member 6202—and more particularly the width of the flange 6206—may change along its length. While it may be generally beneficial to provide a larger width and therefore surface area, this may be constrained in certain locations by facial features. Varying the width of the textile seal member 6202 along its length may assist with accommodating for this. In one form, the textile seal member 6202 may come in various sizes (e.g., small, medium, large), each with different widths that may be preselected based on average sizes of human faces. In another form, the width of the textile seal member 6202 may be selected based on the individual patient. For example, the patient's face may be measured, and a piece of textile may be cut based on the measurements.

In certain forms of the present technology, the width of the compliant portion 6204 is greater than the thickness of the compliant portion 6204. Reference to width of the compliant portion 6204 should be understood to mean the dimension of the compliant portion 6204 in the radial direction when the patient interface 6000 is worn by the patient. Reference to thickness of the compliant portion should be understood to mean the dimension of the compliant portion in the anterior-posterior direction when worn by the patient—i.e. the dimension of the compliant portion 6204 in a direction between the frame 6100 and the textile seal member 6202.

A compliant portion 6204 with a thickness that is less than the width may assist with maintaining a low profile, facilitating side sleeping and minimising bulk. Further, a thinner compliant portion 6204 may assist with comfort by allowing less relative movement between the frame 6100 and the textile seal member 6202, meaning the patient interface 6000 may feel comfortably snug rather than loose. A smaller spacing between the frame 6100 and the seal member 6202 may also mean that destabilising forces acting on the frame 6100 (e.g. due to tube drag, or forces from the patient's pillow) have less leverage when received at the seal member 6202. As stated above, this may be because a fulcrum point (e.g., between the air circuit 4170 and the frame 6100) is close to the patient's face, which creates a small lever arm. Since the lever arm length (i.e., radius) is directly related to torque, reducing the lever arm (e.g., by creating a low profile patient interface) reduces the torque (e.g., as compared to a frame 6100 spaced further from the patient's skin), and minimizes tube drag.

In certain forms of the present technology, the thickness and/or width of the compliant portion 6204 may vary between different regions of the seal-forming structure 6200.

In certain forms of the present technology, at least a portion of the textile seal member 6202 may be provided directly to the posterior facing surface 6104 of the plenum chamber portion 6102 of the flexible frame 6100. For example, the compliant portion 6204 may not be present in a nasal or nose bridge region or on a nose-ridge region of the patient's face. In other examples, the compliant portion 9204 may not be present proximate to the mental protuberance. In alternative forms, the compliant portion 6204 may be provided along the entirety of the seal-forming structure 6200.

In some forms, the frame 6100 and the compliant portion 6204 may be formed from a single homogeneous piece of material. For example, where the frame 6100 is made of silicone, and the compliant portion 6204 is a silicone structure having the requisite properties, the frame 6100 and compliant portion 6204 may be manufactured as a single piece. A textile cover could be later added around the frame and compliant portion 6204 in order to give the patient a less clinical look and feel. In embodiments in which these components are manufactured separately and subsequently joined (e.g., when the frame 6100 is constructed from a textile), it is envisaged that use of similar materials may assist with joining of the components—for example using welding or an adhesive. These methods for joining components may also be used when joining the compliant portion 6204 to the textile seal member 6202.

5.3.2.1.2 Surface of Seal-Forming Structure

In one form, the seal-forming structure 6200 comprises a region having a tacky or adhesive surface. This may be a material property of the textile, or it may be added separately to the textile (e.g., via a spray, a coating, a laminate, printing, molding, etc.). In certain forms of the present technology the textile seal member 6202 comprises at least one seal enhancing feature 6208 on a posterior facing surface of the textile seal member (i.e. the target seal-forming region). The seal enhancing feature 6208 may facilitate a good seal between the patient's face and the textile material of the textile seal member 6202 and/or help the textile seal member 6202 to grip the patient's face. In examples, the seal enhancing feature 6208 may increase the tackiness of the textile seal member 6202.

In one form the, seal enhancing feature 6208 may comprise a layer of seal enhancing material. By way of example, the coating may be polyurethane, or silicone.

In another form, the seal enhancing material of the seal enhancing feature 6208 may be a foam material.

In one form the seal enhancing feature 6208 may comprise seal enhancing material 6210 provided in a discontinuous manner, i.e. such that gaps are formed exposing the textile seal member 6202. In such examples, the seal enhancing material 6210 may be provided in a variety of ways, e.g., random, patterns (for example, stripes as shown in FIG. 8-2, dashes as shown in FIG. 8-3, or dots), spiral, winding tracks, or combinations thereof. The textile seal member 6202 may have a heavier concentration of seal enhancing material 6210 in locations that would require more tackiness or in locations where sealing could be improved. These locations could be generalized for the average person, or the locations could be included specifically for each individual patient (e.g., based off of measurements taken from the patient). The different patterns could also provide different advantages and could therefore be selected for a specific patient, as a way to customize the fit and feel for the individual patient.

In one form the seal enhancing feature 6208 may be provided in a select region or regions along the length of the textile seal member 6202. In one form the seal enhancing feature 6208 may be provided to a greater extent in a select region or regions—for example over a larger area or with a greater degree of tackiness. By way of example, regions that in use contact a nasal or nose bridge region or on a nose-ridge region of the patient's face may be provided with greater seal enhancement. In one form the seal enhancing feature 6208 may be provided along the entirety of the length of the textile.

5.3.2.2 Nose Bridge or Nose Ridge Region

In one form, the seal-forming structure forms a seal in use on a nasal or nose bridge region or on a nose-ridge region of the patient's face.

In examples, the seal-forming structure may be provided on the nose-bridge towards the pronasale of the patient. In examples, the seal-forming structure may be provided on the nose-ridge of the patient inferior to the nose-bridge. Generally, it is desirable to reduce forces applied to the regions on the nose which may result in occlusion. However, the lower retention forces required by the seal-forming structure according to examples of the present technology may allow for positioning of the seal-forming structure in this region in order to reduce the obtrusiveness of the patient interface in the vision of the patient.

In other forms, the seal-forming structure may be positioned entirely below the patient's pronasale, so that no seal is formed with the nose bridge or nose ridge region. This may further reduce obtrusiveness of the patient interface in the vision of the patient.

5.3.2.3 Upper Lip Region

In one form, the seal-forming structure forms a seal in use on an upper lip region (that is, the lip superior) of the patient's face.

5.3.2.4 Chin-Region

In one form the seal-forming structure forms a seal in use on a chin-region of the patient's face.

5.3.2.5 Forehead Region

In one form, the seal-forming structure forms a seal in use on a forehead region of the patient's face. In such a form, the plenum chamber or frame may cover the eyes in use.

5.3.2.6 Nasal Pillows

In one form the seal-forming structure comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form the positioning and stabilising structure 3300 provides a retention force of at least (6 (g-f/cm$^2$)×mask footprint area (cm$^2$)) in use.

In one form the positioning and stabilising structure 3300 provides a force of less than (30 (g-f/cm$^2$)×mask footprint area (cm$^2$)) in use.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow. In one form of the present technology, a positioning and stabilising structure 3300 is provided that comprises a rear portion having a thickness of no greater than 2 cm in use.

In one form of the present technology, a positioning and stabilising structure 3300 is provided that is configured so as not to be too large and bulky to prevent the patient from lying in a side sleeping position with a side region of the patient's head on a pillow. In one form of the present technology, a positioning and stabilising structure 3300 is provided that comprises a low profile side portion configured to be positioned under the patient's head while the patient is lying in a side sleeping position.

In one form of the present technology, a positioning and stabilising structure 3300 comprising a tie is provided, a portion of the tie being dimensioned and structured to engage in use a portion of the patient's head in a region of a parietal bone, wherein the positioning and stabilising structure has a non-rigid decoupling portion.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a portion of a positioning and stabilizing structure is constructed to be breathable to allow moisture vapour to escape and/or be transmitted therethrough.

In certain forms of the present technology, a positioning and stabilising structure 3300 comprises a strap constructed to be breathable to allow moisture vapour to be transmitted through the strap.

In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another. suitable for a small sized head, but not a large sized head.

FIG. 7-1 shows a patient interface 6000 according to one example of the present technology having a positioning and stabilising structure 6300 and a frame 6100. The positioning and stabilising structure 6300 in this example includes a plurality of headgear straps connected to lateral portions 6108 the frame 6100 in order to support the frame 6100 in a sealing position against the patient's face.

It will be understood that a single "strap" may be formed by multiple lengths of material(s) that have been cut or formed separately and then joined together at their ends to create a longer length or single "strap" may be a single length of material(s). In examples, the various straps may be selectively adjustable—whether relative to each other and/or the frame 6100. For example, connection points may be provided having an aperture through which a strap may be passed through and looped back onto itself to be secured. For example, a strap may be releasably secured using hook and loop materials configured to releasably bind to each other upon contact, a band, a buckle connection, a clip or the like. In examples, one or more magnetic clips may be used to releasably secure a strap, and advantages and features of a positioning and stabilising structure comprising magnetic clips are described in WO 2014/110622, the entire contents of which are incorporated herein by reference. In examples of the present technology, the ability to independently adjust left and right straps, and/or upper and lower straps may assist with shaping and adjusting the seal-forming structure 6300 to achieve a desired fit.

In the example illustrated in FIG. 7-1 the positioning and stabilising structure 6300 comprises a pair of upper straps 6310. Each upper strap 6310 is configured to pass between a respective eye and ear of the patient. Additionally, the positioning and stabilising structure 6300 comprises a pair of lower straps 6320 configured to lie over the patient's cheeks below the patient's cheekbones.

In this example, the frame 6100 is held in position via a four-point connection to the straps at the lateral portions 6108 of the frame 6100. In examples, the straps may be stitched, bonded or integrally formed with the frame 6100.

In some examples, the each lateral portion 6108 is integrally formed with the pair of lower straps 6320. In other words, the lateral portions 6108 and the lower straps 6320 may be formed from a single piece of material. Each lower strap 6320 may extend to and connect with the frame 6100. The lateral portion 6108 may represent a transition, in order to assist with coupling the pair of lower straps 6320 to the frame 6100. For example, the width of each lateral portion 6108 may be greater than the remainder of the lower straps 6320. A widest portion of the lateral portion 6108 may be coupled to the frame 6100 in order to provide a more secure connection to the frame 6100 (e.g., because there is a greater connection length). In other words, the lateral portion 6108 (via the upper and lower straps 6310, 6320) may provide a force along an entire vertical length of the frame 6100, which may assist in providing a sealing force to the entire perimeter of the frame 6100. The frame 6100 and the lateral portion 6108 may also be constructed from a single piece of material, and the width of the lateral portion 6108 may taper in order to substantially match the shape of the frame 6100 (e.g., in order to form a substantially smooth transition). The changing widths allows the upper and lower straps 6310, 6320 to have relatively small widths along the lateral sides of the patient's head (e.g., in order to minimize discomfort, limit contact with the patient's ears, etc.), and larger widths in the anterior of the patient's head.

In one example, the upper straps 6310 and the lower straps 6320 are each constructed as a single piece, and are connected together at the lateral portion 6108. In other words, the upper strap 6310 and the lower strap 6320 on a respective side of the patient's head converge toward the lateral portion 6108, which includes a width at least as large as the total combined width of the upper and lower straps 6310, 6320. The upper and lower straps 6310, 6320 are each coupled to the frame 6100 via the lateral portion 6108.

In one example (see e.g., FIG. 11), each lateral portion 6108 may extend only from the respective lower strap 6320. In other words, each lower strap 6320 increases its width along the respective lateral portion 6108 toward the frame 6100. The lateral portion 6108 is a transition between each lower strap 6320 and the frame 6100 and may taper in order to substantially match the shape of the frame 6100 (e.g., in order to form a substantially smooth transition).

The positioning and stabilising structure 6300 may also comprise one or more of a top crown strap 6330, a pair of lateral crown straps 6332 and a neck strap 6334. The top crown strap 6330 is configured to pass around the patient's head and lie against superiorly and posteriorly facing surfaces. The top crown strap 6330 may be configured to overlie the parietal bone of the patient's skull. Each end of the top crown strap 6330 connects to a respective one of the upper straps 6310 and also to a respective one of a pair of lateral crown straps 6332. Each one of the lateral crown straps 6332 connects between the upper strap 6310 and the lower strap 6320 on a respective side of the patient's head. The inferior ends of the lateral crown straps 6332 are connected to each other by a neck strap 6334. The neck strap 6334 may be configured to pass across the sagittal plane and lie against inferior and/or posterior facing surfaces of the patient's head or lie against the back of the patient's neck. The neck strap 6334 may overlie, or lie inferior to, the occipital bone of the patient's skull.

In some forms, all of the straps that make up the positioning and stabilising structure 6300 are constructed from a single piece of material. In other words, the individual straps are all connected to one another without the use of fasteners (e.g., sewing, clips, magnets, etc.). This may simplify manufacturing, and provide seamless transitions between the respective straps.

In some forms, at least one strap of the positioning and stabilising structure 6300 is not integrally formed with the other straps. For example, one strap may include an end not formed as a continuous piece of material with an additional strap. The end may be coupled to the additional strap using fasteners (e.g., sewing, welding, etc.) in order to permanently affix the straps together. Alternatively, the straps may be coupled together using removable fasteners (e.g., mechanical latches, magnets, etc.) so that the straps may be selectively coupled together (e.g., to provide length adjustment, assist in removal, etc.).

In examples of the present technology, the positioning and stabilising structure 6300, or at least components thereof, may be made of an elastic material. The positioning and stabilising structure 6300 may stretch sufficiently to allow the patient interface 6000 to be donned and doffed without the need to release or attach one or more of the straps. The flexible nature of the frame 6100 and/or the relatively low retention force required by the seal-forming structure 6200, according to examples of the present technology, may allow the use of a positioning and stabilising structure 6300 which stretches with relative ease in comparison with traditional patient interfaces.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

FIG. 9-1 shows an example of a vent 3400-1 provided on the connection port 3600. FIG. 9-1 also shows another example of a vent 3400-2 formed in an insert 6110 provided to the frame 6100, where the insert 6110 may be made of a more rigid material than the frame. The insert 6110 may be removably positionable in the frame 6100. A patient my selectively remove the insert 6110 for cleaning. The insert 6110 may also be permanently coupled to the frame 6100, so that it cannot be removed without damaging the frame 6100.

FIG. 10-1 shows an example of a vent 3400-3 in the form of a portion of the frame 6100 being made of an air permeable material. In certain examples, vent 3400-3 may be made of a different material to that of the remainder of the frame 6100 (e.g. a mesh, or an air permeable textile material). In certain examples where the frame is made of a textile material in which one or both sides of the textile material is coated, laminated, sealed, or provided with an air impermeable surface, the vent 3400-3 may be provided by excluding a portion of the textile material from being provided with the air impermeable surface. In other words, the vent 3400-3 is not coated, laminated, sealed, or provided with an air impermeable surface, in order to allow air to permeate through that section of the frame. FIG. 10-2 shows an example of a vent 3400-4 formed directly in the frame 6100—i.e. holes are provided in the material of the frame 6100. The entire surface of the frame 6100 (e.g., posterior and anterior surfaces 6104, 6106) may be laminated, sealed, or provided with an air impermeable surface. The holes of the vent 3400-4 extend entirely though the posterior and anterior surfaces 6104, 6106 in order to provide a flow path for fluid (e.g., exhale gasses) to escape to ambient.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

In the example of FIG. 9-1, the connection port 3600 is in the form of a ring member structured and arranged to provide a releasable connection between the frame 6100 and the air circuit 4170. The connection port 3600 may be swivelable relative to the frame 6100 and/or the connection to the air circuit 4170 may also be swivelable. In examples, the connection port 3600 may comprise an elbow assembly configured to connect to the air circuit 4170 (e.g., via a swivel connector) and a ring member configured to connect to the frame 6100. Such an elbow assembly may be repeatedly engageable with and removably disengageable from (i.e., connectable to and disconnectable from) the ring member to facilitate a releasable or separable connection between the frame 6100 and the air circuit 4170.

In one example (see e.g., FIGS. 9-2 and 9-3), the frame 6100 may include an opening 6112 (e.g., a circular opening) that extends through the plenum chamber 6102, and provides fluid communication between a patient wearing the patient interface 6000 and the ambient environment. The connection port 3600 may be similarly shaped with respect to the opening. However, the connection port 3600 may include projections 3602 that extend radially outward (e.g., from the circularly shaped connection port 3600). The connection port 3600 may be made from a flexible, elastically deformable material (e.g., an impermeable textile, silicone, etc.). The patient may compress the connection port 3600, so that the projections 3602 may be radially within the opening 6112 of the plenum chamber 6102. Once the projections 3602 pass through the opening 6112 (e.g., are positioned proximate to the posterior surface 6104), the patient may release the compressive force so that the connection port 3600 returns to its initial position. The projections 3602 may rest against the posterior surface 6104 in order to prevent the removal of the connection port 3600 from the plenum chamber 6102 (until the connection port 3600 is deformed again). The connection port 3600 may also have a taper in order to form a substantially sealed interface between the frame 6100 and the connection port 3600.

Since the frame 6100 of FIGS. 9-2 and 9-3 may also include the low profile shape, tube drag caused by the connection between the connection port 3600 and the frame 6100 may be similarly limited as previously described.

In alternative examples, the air circuit 4170 may be provided directly to the frame 6100.

5.3.7 Forehead Support

In one form, the patient interface 3000 includes a forehead support 3700 (see e.g., FIG. 3A).

Examples of the patient interface of the present technology shown in FIGS. 7-1 to 11 do not include a forehead support. Variations of the patient interface of the present technology may include a forehead support.

5.3.8 Conduits

The patient interface 3000 according to examples of the present technology may include conduits to provide the flow of pressurized from the connection port 3600 to the interior of the plenum chamber 3200.

In examples, as shown in FIG. 9-1, the patient interface 6000 includes a single conduit (indicated as air-circuit 4170 in FIG. 9-1) and associated connection to the frame 6100 via connection port 3600. In the example of FIG. 9-1, the connection port 3600 is provided in a medial and inferior position on the frame 6100.

As shown in the examples of FIGS. 10-1 and 10-2, the patient interface 6000 may comprise conduits 6900 passing along lateral sides of the patient's head between corresponding ones of the patient's eyes and ears. For example, the conduits 6900 may extend across a similar region of the patient's face as the pair of upper straps 6310. The conduits 6900 may be connected to the plenum chamber of the frame 6100 to provide the flow of pressurized air to the patient. The conduits 6900 may be constructed from an impermeable textile (e.g., the same material as the frame), an elastomer (e.g., silicone), or other suitable material. For example, the conduits 6900 may be a thermoformed structure.

In a first example of FIG. 10-1, first conduit 6900-1 is integrated into an upper strap 6310 of the positioning and stabilising structure 6300, with a conduit connection portion 6902 extending from the upper strap 6310 to the plenum chamber of the frame 6100.

The first conduit 6900-1 may provide dual functions of both air delivery and force transfer. In other words, in addition to providing the flow of pressurized air to the patient, the first conduit 6900-1 makes up and portion of the positioning and stabilizing structure 6300, and transfers associated forces to the frame 6100 in order to assist in sealing the textile seal member 6202 against the patient's face.

In the illustrated example, the first conduit 6900-1 connects directly to the frame 6100 (i.e., not to an intermediate lateral portion 6108). Since the lower straps 6320 do not convey the flow of pressurized air and are connected to the frame 6100 outside of the seal-forming structure 6200, the first conduit 6900-1 connects to the frame 6100 in a different location. In this case, the first conduit 6900-1 connects to the frame 6100 in a location proximate to the patient's nares when the patient interface 6000 is worn. In other words, the patient's nose is positioned close to the first conduit 6900-1 so that pressurized breathable gas conveyed by the first conduit 6900-1 is directed toward the patient's nares.

In one example, the first conduit 6900-1 is removably connected to the connection portion 6902. The patient may disconnect the first conduit 6900-1 and the connection portion 6902 in order to assist with cleaning the first conduit and/or in order facilitate the donning and/or doffing of the patient interface 6000 (e.g., by reducing the tension applied by the positioning and stabilising structure 6300. The connection between the first conduit 6900-1 and the connection portion 6902 may be made via a snap or friction fit. The connection portion 6902 may be removably connected to the frame 6100 (e.g., in a similar manner as described with respect to the connection port 3600) in addition to or instead of the first conduit 6900-1 in order to provide similar benefits.

In one example, the first conduit 6900-1 and the connection portion 6902 are permanently coupled together. The connection portion 6902 and the frame 6100 are also permanently coupled together. In other words, the first conduit 6900-1 and the connection portion 6902 are fixed to the frame 6100 (e.g., through sewing, welding, adhesives, etc.) so that a patient may be unable to remove the first conduit 6900-1 from the frame 6100.

An alternative example is also illustrated in FIG. 10-2, in which second conduit 6900-2 is provided over the upper strap 6310 of the positioning and stabilising structure 6300. The inferior end of the conduit 6900-2 connects to a conduit connector 6800 which provides a pneumatic connection to the interior of the frame 6100 to provide the flow of pressurized air to the plenum chamber. The conduit connector 6800 may be permanently or releasably connected (e.g., via a mechanical fastener, a magnet, etc.) to an intermediary connector to the frame 6100, or directly to the frame 6100. The conduit connector 6800 may be structured similarly to the connection port 3600, and may be removable from the frame 6100 in a similar manner. The conduit connector 6800 may also be coupled together in any other suitable manner (e.g., that creates a seal between the conduit connector 6800 and the frame 6100). For example, there may be a press fit or friction fit between the conduit connector 6800 and the frame 6100. There may also be a push button actuatable by the patient in order to the release the connection between the conduit connector 6800 and the frame 6100. The conduit connectors 6800 may provide other functions, as described below, such as venting of the plenum chamber, connection to the positioning and stabilising structure 6300, and asphyxia prevention by inclusion of an anti-asphyxia valve. The conduit connector 6800 may be constructed from an elastomeric material (e.g., silicone), a rigid material (e.g., plastic), and/or a textile material (e.g., the same material as the frame 6100).

The conduits 6900 may also provide stabilize and position the seal-forming structure 6200 on the patient's face. Thus, the conduits 6900 may function similarly to the ties of the positioning and stabilising structure 6300. The conduits 6900 may include features of similar conduits disclosed in International Application Publication No. WO 2017/124155 A1, which is incorporated by reference herein in its entirety. For example, the conduits 6900 of the present technology may include features of the headgear tubes 3350 depicted in FIGS. 3A-3L of this document, as well as the associated written description.

FIG. 11, shows an example of the patient interface 6000 in which the positioning and stabilising structure 6300 in this example comprises a pair of conduits 6900. The pair of conduits 6900 are connected to each other at their superior ends and are each configured to lie against superior and lateral surfaces of the patient's head in use. Each of the conduits 6900 may be configured to lie between and eye and an ear of the patient in use. The inferior end of each conduits 6900 is configured to fluidly connect to the plenum chamber of the frame 6100. In this example, the inferior end of each conduits 6900 connects to a conduit connector 6800. The positioning and stabilising structure 6300 comprises a conduit headgear inlet 6390 at the junction of the conduits 6900. The conduit headgear inlet 6390 is configured to receive a pressurised flow of gas, for example via an elbow comprising a connection port 3600, and allow the flow of gas into hollow interiors of the conduits 6900. The conduits 6900 supply the pressurised flow of gas to the plenum chamber of the frame 6100.

The positioning and stabilising structure 6300 may comprise one or more straps in addition to the conduits 6900. In this example the positioning and stabilising structure 6300 comprises a pair of lateral crown straps 6332 and a pair of lower straps 6320. The posterior ends of the lateral crown straps 6332 and lower straps 6320 are joined together by a neck strap 6334. The junction between the lateral crown strap 6332 and lower strap 6320 is configured to lie against a posterior surface of the patient's head in use, providing an anchor for the lateral crown straps 6332 and lower straps 6320. Anterior ends of the lateral crown straps 6332 connect to the conduits 6900. In this example each conduit 6900 comprises a tab 6342 having an opening through which a respective lateral crown strap 6332 can be passed through and then looped back and secured onto itself to secure the lateral crown strap 6332 to the conduit 6900.

In one form, the patient interface 3000 includes at least one anti-asphyxia valve. In an example depicted in FIG. 10-2, the conduit connector 6800 may include an anti-asphyxia valve 6802. By way of example, the anti-asphyxia valve 6802 may include an anti-asphyxia valve flap that covers an anti-asphyxia valve hole in a closed position, such that the flow of pressurized air entering the anti-asphyxia valve 6802 will be prevented from escaping to atmosphere through the anti-asphyxia valve hole by the anti-asphyxia valve flap and will be directed into the plenum chamber. The anti-asphyxia valve flap may be configured to remain in the closed position during the patient's entire respiratory cycle, i.e., inhalation and exhalation. Thus, the patient receives the flow of pressurized air to their airways to ensure that patient's airways maintain sufficient patency during inhalation and exhalation. If there is a cessation of the flow of pressurized air, the anti-asphyxia valve flap is positioned in an open position in which the anti-asphyxia valve hole is not covered such that the patient can breathe from atmosphere via the anti-asphyxia valve hole.

5.3.8.1 Integrally Constructed Conduit with Full Face Seal

In some forms, as shown in FIGS. 12-1 to 12-5, the patient interface 9000 may be formed as a single piece (e.g., integral, seamless connection), so that the frame 9100, the seal-forming structure 9200, and the positioning and stabilising structure 9300 are formed integrally. Conduits 9900 may also be formed as a single piece with the rest of the patient interface 9000 (i.e., the frame 9100, the seal-forming structure 9200, and/or the positioning and stabilising structure 9300). Although in some examples, at least one of the conduits 9900 may be disconnected from the frame 9100 (e.g., to assist with donning/doffing, cleaning, etc.).

In some forms, the patient interface 9000 may be a full-face seal, or an ultra-compact full-face seal, both which seal around the patient's mouth and the patient's nares, so that air pressurized air may be inhaled though either orifice.

In some forms, the conduits 9900 are separate structures from the positioning and stabilising structure 9300. In other words, the straps and the conduits 9900 are not identical structures. As shown in FIG. 12-1, the conduits 9900 are overlayed onto the upper strap 9310. However, only the upper strap 9310 contacts the patient's head, and the upper strap 9310 extends wider than the conduits 9900.

In certain forms, the conduits 9900 are fixed relative to the upper strap 9310. In other words, the conduits 9900 and the upper strap 9310 may be formed from a single piece, as previously described. For example, the conduits 9900 may be constructed from the same a textile material (e.g., a knitted structure) as the positioning and stabilising structure 9300. Since they are formed as one piece, the conduits 9900 may be unable to laterally translate along the width of the upper strap 9310.

In one form, the upper strap 9310 may be connected to the conduits 9900, and may form a portion of the wall of the conduits 9900. In other words, the each upper strap 9310 is connected to the respective conduit 9900 with a seamless connection (e.g., via a heat seal). A portion of the unassembled conduit 9900 may have a substantially U-shape, so that when the conduit 9900 is coupled to the respective upper strap 9310, the conduit 9900 is enclosed. The upper strap 9310 may be impermeable (e.g., coated with an air impermeable substance) since the upper strap 9310 forms a portion of the inner passageway of the conduit 9900. For example, the upper strap 9310 may only be impermeable on the non-patient contacting side (i.e., the side of the upper strap 9310 within the volume of the respective conduit 9900), so that the patient contacting side still includes the textile properties (e.g., comfort against the patient's skin).

Since each upper strap 9310 and conduit 9900 is formed as a single structure, the conduit 9900 may not move relative to the upper strap 9310. The upper strap 9310 may be configured to remain relatively stationary on the patient's head (e.g., in order to maintain the desired sealing force while the patient is sleeping). Thus, tube drag (or other forces received by the frame 6100) may be reduced and/or eliminated because the conduits 9900 may be unable to pull and provide a force to the frame 6100.

In some forms, the patient interface 9000 may not include a conduit connection portion. Instead of the conduits 9900 of the patient interface 9000 may directly extend into the compliant portion 9204 and/or the textile seal portion 9202. In the illustrated examples, the conduits 9900 extend to a region proximate the patient's subnasale, in order to deliver pressurized air directly to the patient's nares. For example, the conduits 9900 may include openings (e.g., one for each nostril) that seal against the patient's alar rims. The conduits 9900 therefore directly contact at least a portion of the patient's face. This may assist in further reducing the occurrence of tube drag, since the lever arm between the patient's face and each conduit 9900 will be further reduced.

In some forms, as shown in FIG. 12-5, the conduits 9900 of the patient interface 9000 may include three separate openings for conveying pressurized air to the patient's airways. For example, the first two openings 9910 (i.e., nasal openings) are nasal openings, as described above, the textile seal portion 9202 substantially seals around the patient's alar rims in order to deliver pressurized air to the patient's nares. The textile seal portion 9202 also may be positioned in order to substantially limit overlap with the patient's nares (e.g., in order to limit breathing obstructions). The third opening 9920 (i.e., an oral opening) may be directed in substantially the opposite direction as the openings 9910, and direct pressurized air into a cavity 9250 of the plenum chamber 9200. This air may be directed toward the patient's mouth, so that inhalation through a patient's mouth will also introduce pressurized air to the patient's airways.

In certain forms, the opening 9920 does not seal around the patient's mouth, and may simply divert air toward the patient's mouth, as opposed to conveying air directly into the patient's airways (e.g., as the openings 9910 do). In other words, opening 9920 is interior to an outer perimeter of the textile sealing portion 9202. Air flowing through the opening 9920 does not flow directly into the patient's mouth. Instead, the pressurized air flows into the volume pressurized by the textile seal portion 9202, where the patient may then inhale the air. This allows the opening 9920 to be smaller than the size of the patient's mouth, which may improve the quality of the textile seal portion 9202 (e.g., limit occurrences of leaks).

In certain forms, the openings 9910, 9920 are generally positioned proximate a center of the frame 6100. In other words, all of the openings 9910, 9920 are disposed proximate to the patient's columella. The opening 9920 may be substantially aligned with the columella, while the openings 9910 may be outside of the columella, and aligned with the patient's nares. The openings 9910 may at least partially overlap with the opening 9920.

The conduits 9900 may not include impedances that direct the pressurized air into any one of the openings 9910, 9920. In other words, pressurized air may flow through all of the openings 9910, 9920, in order to convey pressurized air to the patient's mouth and to the patient's nose.

In some forms, the patient interface 9000 may include an exterior rigidizing portion 9350, which may assist in maintaining the shape of the patient interface 9000 (e.g., specifically the conduits 9900 and/or the frame 9100).

In some forms, the rigidizing element may be formed from a flexible or semi-rigid material. In other words, the rigidizing portion 9350 may be more rigid than the textile seal portion 9202, but the rigidizing portion 9350 may not be formed from a rigid material (e.g., hard or semi-rigid plastic). This way, the patient interface 9000 may maintain its soft and/or compliant feel, which may promote patient compliance and/or limit foreign bedroom materials (e.g., silicone).

In certain forms, the rigidized element 9350 may be constructed from a textile material. For example, the rigidized element 9350 may be constructed from the same material as the remainder of the patient interface 9000. This may facilitate constructing the patient interface 9000 as one piece, since all of the material is substantially the same. Rigidized threads may be incorporated into the rigidized element 9350 (e.g., either before or after assembly of the patient interface 9000) in order to provide additional rigidity to the rigidized element 9350.

In certain forms, the rigidized element 9350 may be constructed from a material different than the textile material used in other portions of the patient interface 9000. For example, the rigidized element 9350 may be constructed from a foam. The foam may be more rigid than the textiles used in other portions of the patient interface, but may still possess a soft and/or compliant feel. Additionally, the foam may be integrated into the patient interface 9000 so that the textile and foam materials are formed as an integral piece in a one piece construction.

In some forms, the rigidizing portion 9350 may extend over the patient's mouth. As shown in FIG. 12-3, a region of the patient's face from the lip superior to below the mental protuberance may be covered by the rigidizing portion 9350. The rigidizing portion 9350 may cover the frame 9100, although in some examples, the frame 9100 is constructed from the rigidizing portion 9350. The rigidizing portion 9350 may not completely cover the portion of the conduits 9900 that seal around the patient's nares. In other words, an uppermost portion of the frame 9100 and/or seal-forming structure 6200 is not covered by the rigidizing portion 9350. This may allow the nasal region more flexion, so that the flexible material of the conduits 9900 may deform as the patient contacts the nose contacts the patient interface 9000. Specifically, this may promote a one-size fits all or one-size fits most patient interface 9000, because the nasal portion of the patient interface 9000 may be able to deform in order to conform to a wide variety of sizes of patient's noses.

In some forms, the rigidizing element anterior to the patient's face may assist in maintaining the shape of the frame 9100 and/or the cavity 9250. In other words, the pressurized air may apply a force to the frame 9100 as it is introduced into the cavity 9250. Since the frame 9100 may be constructed from textile (or other similar flexible material), the frame 9100 may have a tendency to deform (e.g., blow out) as a result of the force. This deformation may eliminate the low profile of the patient interface 9000, and may also cause a potential lever arm to increase in length (i.e., thereby increasing the potential of tube drag).

The rigidizing portion 9350 therefore helps to maintain the low profile of the patient interface 9000 by maintaining a substantially constant volume within the cavity 9250. Additionally, since the patient may not sleep with their face directly contacting a surface, like a pillow, because breathing would become difficult or impossible, the rigidizing portion 9350 may cause the patient discomfort while they are sleeping.

In some forms, rigidizing portion 9350 may extend along the upper straps 9310 and/or the lower straps 9320. The rigidizing portion 9350 may be a continuous element, so that the rigidizing portion 9350 extends interrupted from one upper strap 9310 to the other upper strap 9310 (and similarly from one lower strap 9320 to the other lower strap 9320).

In some forms, a lower portion 9352 of the rigidizing portion 9350 may not cover the entirety of the lower straps 9320. As shown in FIG. 12-2, the lower portion 9352 may extend along the inferior-most portion of the lower strap 9320, while the remainder of the lower strap 9320 remains uncovered by the lower portion 9352.

In some forms, an upper portion 9354 of the rigidizing portion 9350 may not cover the entirety of the upper straps 9310. As shown in FIG. 12-2, the upper portion 9354 may extend adjacent to the conduit 9900. The upper portion 9354 may be spaced apart from the patient's ear so that the remainder of the upper strap 9310 remains uncovered by the upper portion 9354.

In certain forms, the upper portion 9354 may not extend to the top crown strap 9330 of the patient interface 9000. The upper portion 9354 may stop approximately at a junction between the upper strap 9310, the top crown strap 9330, and the lateral crown strap 9332. This junction may be superior to the helix of the ear.

In certain forms, the lower and upper portions 9352, 9354 of the rigidizing portion 9350 may form a substantial U-shape or V-shape along either side of the patient's head. The lower and upper portions 9352, 9354 may be positioned on either side of the patient's ear, so as to not contact the patient's ear.

In certain forms, as shown in FIG. 12-3, the lower and/or upper portions 9352, 9354 may extend more laterally than the remainder of the patient interface 9000. In other words, the lower and upper portions 9352, 9354 may extend further away from the patient's head (i.e., in the left-right direction) as compared to the rest of the positioning and stabilising structure 9300. For example, the upper portion 9354 extends more laterally than the conduit 9900. This may be beneficial to a patient who sleeps on their side, because the lower and/or upper portions 9352, 9354 may contact the sleeping surface (e.g., bed, pillow, etc.) prior to the conduits 9900, or other portions of the positioning and stabilising structure 9300, contacting the sleeping surface. The lower and/or upper portions 9352, 9354 may act as a spacer between the conduit 9900 and the sleeping surface, so that the patient's weight may be less likely to collapse the conduit 9900 as a result of the patient sleeping on their side. The greater rigidity of the lower and/or upper portions 9352, 9354 may be less likely to compress and/or collapse under the patient's weight. In this way, the force of the patient's head may not be transferred to the conduit 9900.

In one form, the upper portion 9354 and the lower portion 9352 may extend the same lateral distance away from the patient's head. In other words, a plane substantially parallel to the sagittal plane may contact the lower and upper portions 9352, 9354. Thus, the patient's head may be able to rest evenly on the sleeping surface, and not be inclined as a result of one portion 9352, 9354 extending further than the other portion 9354, 9352.

In certain forms, the lower and/or upper portions 9352, 9354 may have a lower stretchability than the remainder of the positioning and stabilising structure 9300 (e.g., constructed from unrigidized textile). Since the rigidizing portion 9350 is coupled to the conduits 9900, a least a portion of the conduits 9900 (e.g., proximate the patient's face) may also have lower stretchability. This may further assist in reducing tube drag, since the conduits 9900 may be limited in the amount they are able to stretch, and therefore the force that they may apply to the frame 9100.

5.3.8.2 Integrally Constructed Conduit with Nasal Seal

In some forms, as shown in FIG. 13, the patient interface 12000 may be formed as a single piece (e.g., integral, seamless connection), so that the frame 12100, the seal-forming structure 12200, and the positioning and stabilising structure 12300 are formed integrally. Conduits 12900 may also be formed as a single piece with the rest of the patient interface 12000.

In some forms, the patient interface 12000 may be a nasal only seal, which seals around only the patient's nares. This may be effective for patients who only breathe through their nose, since pressurized air will not be delivered to the patient's mouth.

As shown in FIG. 13, the patient interface 12000 is substantially similar to the patient interface of FIGS. 12-1 to 12-5. However, the patient interface 12000 of FIG. 13 leaves the mouth exposed (i.e., the mouth is not sealed in a pressurized volume). This may improve patient compliance because a smaller percentage of the patient's face is covered by the patient interface 12000, so the patient may be more comfortable wearing the patient interface 12000 to bed.

Since the patient interface 12000 is only delivering pressurized air to the patient's nares, the patient interface 12000 only needs to seal around the patient's nose. In other words, the perimeter of the textile seal member 12202 may be less than in the patient interface 9000, since the textile seal member 12202 only needs to seal around the patients alar rims.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10$cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 $cmH_2O$ to about 20 $cmH_2O$, or in other forms up to about 30 $cmH_2O$. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier 5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components 5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5C. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor 4272 provided in the RPT device 4000.

5.6.2.5.2 Flow Rate Transducer

One or more flow rate transducers 5214 may be provided to the humidifier 5000 in addition to, or instead of, a flow rate sensor 4274 provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier base 5006 where heat may be provided to the humidifier reservoir 5110 primarily by conduction as shown in FIG. 5B.

5.6.2.7 Humidifier Controller

According to one arrangement of the present technology, a humidifier 5000 may comprise a humidifier controller 5250 as shown in FIG. 5C. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.7 Breathing Waveforms

FIG. 6 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. ‘Flow rate’ is sometimes shortened to simply ‘flow’ or ‘airflow’.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/$cm^2$ and hectopascal. 1 $cmH_2O$ is equal to 1 g-f/$cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

- 'Soft' materials may include silicone or thermo-plastic elastomer (TPE), and may, e.g. readily deform under finger pressure.
- 'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

Tack or tackiness: The tendency of a material to stick to another material, particularly at room temperature, as the result of adhesive and/or cohesive forces between materials in contact 5.8.2 Respiratory Cycle Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.8.4 Anatomy 5.8.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius): A point on the face between the mouth and supramenton, lying in the median sagittal plane.

Lip, upper (labrale superius): A point on the face between the mouth and nose, lying in the median sagittal plane.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.8.4.2 Anatomy of the Skull Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space: (description to be inserted here)

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. In forms a frame may form part of the walls of a mask plenum chamber. In some forms a shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| 5.10 REFERENCE SIGNS LIST | |
|---|---|
| patient | 1000 |
| bed partner | 1100 |
| patient interface | 3000 |
| seal - forming structure | 3100 |
| plenum chamber | 3200 |
| chord | 3210 |
| superior point | 3220 |
| inferior point | 3229 |
| positioning and stabilising structure | 3300 |
| vent | 3400 |
| connection port | 3600 |
| projection | 3602 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |

-continued 5.10 REFERENCE SIGNS LIST

| | |
|---|---|
| motor | 4144 |
| anti - spill back valve | 4160 |
| air circuit | 4170 |
| supplemental oxygen | 4180 |
| electrical components | 4200 |
| printed circuit board assembly (PBCA) | 4202 |
| power supply | 4210 |
| input device | 4220 |
| central controller | 4230 |
| clock | 4232 |
| therapy device controller | 4240 |
| protection circuits | 4250 |
| memory | 4260 |
| transducer | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| humidifier | 5000 |
| humidifier inlet | 5002 |
| humidifier outlet | 5004 |
| humidifier base | 5006 |
| humidifier reservoir | 5110 |
| reservoir | 5110 |
| conductive portion | 5120 |
| humidifier reservoir dock | 5130 |
| locking lever | 5135 |
| water level indicator | 5150 |
| humidifier transducer | 5210 |
| air pressure sensor | 5212 |
| air flow rate transducer | 5214 |
| temperature sensor | 5216 |
| humidity sensor | 5218 |
| heating element | 5240 |
| humidifier controller | 5250 |
| central humidifier controller | 5251 |
| heating element controller | 5252 |
| air circuit controller | 5254 |
| patient interface | 6000 |
| frame | 6100 |
| plenum chamber portion | 6102 |
| posterior facing surface | 6104 |
| anterior facing surface | 6106 |
| lateral portion | 6108 |
| frame insert | 6110 |
| opening | 6112 |
| seal-forming structure | 6200 |
| textile seal member | 6202 |
| compliant portion | 6204 |
| rigidiser | 6205 |
| flange | 6206 |
| seal enhancing feature | 6208 |
| seal enhancing material | 6210 |
| position and stabilising structure | 6300 |
| upper strap | 6310 |
| lower strap | 6320 |
| top crown strap | 6330 |
| lateral crown strap | 6332 |
| neck strap | 6334 |
| tab | 6342 |
| conduit headgear inlet | 6390 |
| conduit connector | 6800 |
| anti-asphyxia valve | 6802 |
| conduit | 6900 |
| conduit connection portion | 6902 |
| patient interface | 9000 |
| frame | 9100 |
| plenum chamber portion | 9102 |
| posterior facing surface | 9104 |
| anterior facing surface | 9106 |
| seal-forming structure | 9200 |
| textile seal member | 9202 |
| compliant portion | 9204 |
| cavity | 9250 |
| position and stabilising structure | 9300 |
| upper strap | 9310 |
| lower strap | 9320 |
| top crown strap | 9330 |
| lateral crown strap | 9332 |
| rigidizing portion | 9350 |
| lower portion | 9352 |
| upper portion | 9354 |
| conduit | 9900 |
| nasal opening | 9910 |
| oral opening | 9920 |
| patient interface | 12000 |
| frame | 12100 |
| plenum chamber portion | 12102 |
| seal-forming structure | 12200 |
| textile seal member | 12202 |
| compliant portion | 12204 |
| position and stabilising structure | 12300 |
| upper strap | 12310 |
| lower strap | 12320 |
| top crown strap | 12330 |
| lateral crown strap | 12332 |
| rigidizing portion | 12350 |
| lower portion | 12352 |
| upper portion | 12354 |
| conduit | 12900 |

The invention claimed is:

1. A patient interface for delivering a flow of air to a patient for treatment of sleep disordered breathing, comprising:

a frame including a posterior facing surface and an anterior facing surface opposite to the posterior facing surface, wherein the frame at least partially forms a cavity pressurisable to a therapeutic pressure of at least 6 $cmH_2O$ above ambient air pressure;

a seal-forming structure constructed and arranged to form a seal with a region of the patient's face surrounding an entrance to the patient's airways, said seal-forming structure having a hole therein such that a flow of air at said therapeutic pressure is delivered to at least an entrance to the patient's nares for treatment of sleep disordered breathing, the seal-forming structure constructed and arranged to maintain said therapeutic pressure in the cavity throughout the patient's respiratory cycle in use; and a connection portion configured to convey pressurized air into the cavity, the connection portion extending through the anterior facing surface and the posterior facing surface;

wherein the seal-forming structure comprises a compliant portion provided to the posterior facing surface of the frame, a rigidizing element provided within the compliant portion, and a seal member adapted to sealingly engage the patient's face in use, wherein a width of the entirety of the compliant portion is greater than a thickness of the entirety of the compliant portion, and wherein the frame and the seal member are at least partially constructed from a textile material, and the compliant portion is constructed from a resilient material that is different than the textile material.

2. The patient interface of claim 1, wherein the frame is made entirely of the textile material.

3. The patient interface of claim 1, wherein the frame comprises a plenum chamber portion, the seal-forming structure is provided to a posterior facing surface of the plenum chamber portion, and the plenum chamber portion extends over a hole of the seal-forming structure through which the flow of air at said therapeutic pressure is delivered to at least an entrance to the patient's nares.

4. The patient interface of claim 3, wherein the frame comprises lateral portions extending beyond the seal-forming structure in a direction away from the hole of the seal-forming structure.

5. The patient interface of claim 1, wherein the rigidizing element is exposed to ambient.

6. The patient interface of claim 1, wherein the textile material of the textile seal member is configured to sealingly engage the patient's face in use, and wherein the textile seal member is configured to surround the entrance to the patient's airways and sealingly engage the patient's face in use.

7. The patient interface of claim 6, wherein a width of the textile seal member changes along its length.

8. The patient interface of claim 1, wherein the width of the compliant portion varies between different regions of the seal-forming structure.

9. The patient interface of claim 1, wherein the thickness of the compliant portion varies between different regions of the seal-forming structure.

10. The patient interface of claim 1, wherein the compliant portion is made of a foam material having compliant properties.

11. The patient interface of claim 1, wherein the seal member comprises an overhanging portion extending from the compliant portion, wherein the overhanging portion of the seal member extends from the compliant portion in a radially inward direction, and wherein the overhanging portion of the seal member provides a pressure assisted seal.

12. The patient interface of claim 1, wherein the seal member comprises at least one seal enhancing feature on a posterior facing surface of the seal member, and wherein the seal enhancing feature increases tackiness of the textile seal.

13. The patient interface of claim 12, wherein the seal enhancing material is one or more of: a polyurethane, and a silicone.

14. The patient interface of claim 12, wherein the seal enhancing feature is provided in a select region or regions along a length of the textile seal.

15. The patient interface of claim 12, wherein the seal enhancing feature is provided to a greater extent in a select region in comparison with one or more other regions, and wherein the select region is configured to contact a nasal or nose bridge region or on a nose-ridge region of the patient's face in use.

16. The patient interface of claim 1, further comprising a positioning and stabilising structure, wherein the positioning and stabilising structure provides a force to hold the seal-forming structure in a therapeutically effective position on the patient's head.

17. The patient interface of claim 16, wherein the positioning and stabilising structure is stitched, bonded or integrally formed with the frame.

18. The patient interface of claim 16, wherein at least a portion of the positioning and stabilising structure is elastic.

19. The patient interface of claim 1, further comprising at least one conduit configured to deliver the flow of air at the therapeutic pressure for breathing by the patient to the cavity.

20. The patient interface of claim 19, wherein the at least one conduit is provided to a medial and inferior position on the frame.

21. The patient interface of claim 19, wherein the at least one conduit comprises a first conduit and a second conduit, each passing along lateral sides of the patient's head between corresponding ones of the patient's eyes and ears, and wherein the first conduit and the second conduit form a portion of a positioning and stabilising structure configured to provide a force to hold the seal-forming structure in a therapeutically effective position on the patient's head.

22. The patient interface of claim 1, further comprising a vent structure to allow a continuous flow of gases exhaled by the patient from the cavity to ambient, said vent structure being sized and shaped to maintain the therapeutic pressure in the cavity in use.

23. The patient interface of claim 22, wherein the vent structure comprises vent holes in flexible material of the frame or in a rigid insert provided to the frame.

24. The patient interface of claim 22, wherein the vent structure comprises an air permeable portion of the frame and/or the vent structure is provided in a connection port provided to the frame.

25. The patient interface of claim 1, wherein the seal member contacts the ridge of the patient's nose and the patient's supramenton, in use, wherein the seal member is disposed proximate to the patient's pronasale and configured to be disposed adjacent to the patient's lateral and/or greater alar cartilage, in use, and wherein an uppermost point of the seal member is configured to be substantially aligned with the patient's Frankfort Horizontal, in use.

26. The patient interface of claim 1, wherein the seal member forms a perimeter, and the patient's nasolabial sulcus are configured to be disposed within the perimeter, in use.

27. The patient interface of claim 1, wherein the rigidizing element is arranged to not be exposed to therapeutic gas in the cavity during use.

28. The patient interface of claim 1, wherein the compliant portion is molded around the rigidizing element.

29. The patient interface of claim 1, wherein the compliant portion is formed in one-piece.

* * * * *